US010945703B2

(12) United States Patent
Dykes et al.

(10) Patent No.: US 10,945,703 B2
(45) Date of Patent: *Mar. 16, 2021

(54) IMAGE GUIDED CATHETERS AND METHOD OF USE

(71) Applicant: PERCEPTIVE NAVIGATION LLC, Baltimore, MD (US)

(72) Inventors: Christopher Allen Dykes, Punta Borda, FL (US); Michael J. Zipparo, Elkton, MD (US); Theodore P. Abraham, San Francisco, CA (US)

(73) Assignee: PERCEPTIVE NAVIGATION LLC, Baltimore, MD (US)

( * ) Notice: Subject to any disclaimer, the term of this patent is extended or adjusted under 35 U.S.C. 154(b) by 188 days.

This patent is subject to a terminal disclaimer.

(21) Appl. No.: 16/247,046

(22) Filed: Jan. 14, 2019

(65) Prior Publication Data

US 2019/0142371 A1 May 16, 2019

Related U.S. Application Data

(63) Continuation of application No. 15/845,756, filed on Dec. 18, 2017, now Pat. No. 10,772,600, which is a
(Continued)

(51) Int. Cl.
*A61B 8/00* (2006.01)
*A61B 8/12* (2006.01)
(Continued)

(52) U.S. Cl.
CPC ............. *A61B 8/12* (2013.01); *A61B 8/4483* (2013.01); *A61B 10/04* (2013.01); *A61B 8/0808* (2013.01);
(Continued)

(58) Field of Classification Search
None
See application file for complete search history.

(56) References Cited

U.S. PATENT DOCUMENTS 3,556,079 A 1/1971 Omizo
3,612,050 A 10/1971 Sheridan
(Continued)

FOREIGN PATENT DOCUMENTS

CA 2376103 3/2001
CA 2376103 A1 3/2001
(Continued)

*Primary Examiner* — Joel F Brutus
(74) *Attorney, Agent, or Firm* — Brown Rudnick LLP; Adam M. Schoen

(57) ABSTRACT

An interventional medical device is provided that incorporates a forward-directed ultrasound or optical coherence tomography imaging system that is replaceable depending on how close the device is to the target site for a given medical procedure, the device and system integrated into a single minimally invasive device comprising a first probe housing, needle guide assembly and sheath, a sleeve lock for closing a normally open needle channel of a needle guide of the first distal assembly and a second probe and cable housing assembly locked to the first distal probe housing, needle guide assembly and sheath by a locking tab. The probe and cable housing assembly may comprise a linear phased ultrasound array and an accelerometer for orienting an image produced by the device with the gravitational field of the earth. The medical device can be in the form of an image guided catheter or probe, used in a body orifice, externally on skin tissue or subcutaneously. The device comprises a replaceable and reusable ultrasound imaging assembly (and or OCT assembly) and replaceable interventional devices such as a removable introducer needle, hollow biopsy needle, syringe or other medical instrument. The imaging system may comprise one or more small ultrasound
(Continued)

or OCT imaging systems that can be replaceably integrated into the device by replacing the reusable second probe and cable housing assembly.

19 Claims, 33 Drawing Sheets

Related U.S. Application Data continuation-in-part of application No. 14/865,151, filed on Sep. 25, 2015, now Pat. No. 9,855,021, which is a continuation-in-part of application No. 13/973,476, filed on Aug. 22, 2013, now abandoned, which is a continuation of application No. 13/847,902, filed on Mar. 20, 2013, now Pat. No. 9,149,257, which is a continuation of application No. 11/871,282, filed on Oct. 12, 2007, now Pat. No. 8,403,859, and a continuation-in-part of application No. 11/782,991, filed on Jul. 25, 2007, now Pat. No. 8,403,858, said application No. 14/865,151 is a continuation-in-part of application No. 13/847,902, filed on Mar. 20, 2013, now Pat. No. 9,149,257.

(60) Provisional application No. 62/590,464, filed on Nov. 24, 2017, provisional application No. 62/527,865, filed on Jun. 30, 2017, provisional application No. 62/527,905, filed on Jun. 30, 2017, provisional application No. 62/526,170, filed on Jun. 28, 2017, provisional application No. 60/851,451, filed on Oct. 12, 2006, provisional application No. 61/692,443, filed on Aug. 23, 2012.

(51) Int. Cl.
*A61B 10/04* (2006.01)
*A61M 25/00* (2006.01)
*A61B 8/08* (2006.01)
*A61B 17/34* (2006.01)

(52) U.S. Cl.
CPC .............. *A61B 8/0841* (2013.01); *A61B 8/445* (2013.01); *A61B 8/565* (2013.01); *A61B 2017/3413* (2013.01); *A61M 25/0026* (2013.01)

(56) References Cited

U.S. PATENT DOCUMENTS

| | | | |
|---|---|---|---|
| 4,092,867 A | 6/1978 | Matzuk | |
| 4,327,709 A | 5/1982 | Hanson et al. | |
| 4,540,411 A | 9/1985 | Bodicky | |
| 4,581,025 A * | 4/1986 | Timmermans | A61M 25/0668 604/264 |
| 4,840,613 A | 6/1989 | Balbierz | |
| 4,849,613 A * | 7/1989 | Eisele | G06Q 20/40975 235/379 |
| 4,869,258 A | 9/1989 | Hetz | |
| 5,011,469 A | 4/1991 | Buckberg et al. | |
| 5,068,638 A | 11/1991 | Bickely et al. | |
| 5,106,368 A | 4/1992 | Uldall et al. | |
| 5,159,931 A | 11/1992 | Pini | |
| 5,181,514 A | 1/1993 | Solomon et al. | |
| 5,437,283 A * | 8/1995 | Ranalletta | A61B 8/12 600/463 |
| 5,454,373 A | 10/1995 | Koger et al. | |
| 5,505,088 A | 4/1996 | Chandraratna et al. | |
| 5,509,909 A | 4/1996 | Moy | |
| 5,701,901 A | 12/1997 | Lum et al. | |
| 5,704,361 A | 1/1998 | Seward et al. | |
| 5,762,066 A | 6/1998 | Law et al. | |
| 5,967,984 A | 10/1999 | Chu et al. | |
| 5,997,497 A | 12/1999 | Nita et al. | |
| 6,110,121 A | 8/2000 | Lenker | |
| 6,149,598 A | 11/2000 | Tanaka | |
| 6,162,179 A | 12/2000 | Moore | |
| 6,190,353 B1 | 2/2001 | Makower et al. | |
| 6,238,336 B1 | 5/2001 | Ouchi | |
| 6,248,081 B1 | 6/2001 | Nishtalas et al. | |
| 6,254,573 B1 | 7/2001 | Haim et al. | |
| 6,261,234 B1 | 7/2001 | Lin | |
| 6,306,097 B1 | 10/2001 | Park et al. | |
| 6,368,280 B1 | 4/2002 | Cermak et al. | |
| 6,376,319 B2 | 4/2002 | Ang et al. | |
| 6,505,088 B1 | 1/2003 | Simkin et al. | |
| 6,572,551 B1 | 6/2003 | Smith et al. | |
| 6,582,390 B1 | 6/2003 | Sanderson | |
| 6,592,526 B1 | 7/2003 | Lenker | |
| 6,592,559 B1 | 7/2003 | Pakter et al. | |
| 6,685,648 B2 | 2/2004 | Flaherty et al. | |
| 6,689,062 B1 | 2/2004 | Mesallum | |
| 6,726,677 B1 | 4/2004 | Flaherty et al. | |
| 6,855,115 B2 | 2/2005 | Fonseca et al. | |
| 7,100,614 B2 | 9/2006 | Stevens et al. | |
| 7,191,015 B2 | 3/2007 | Lamson et al. | |
| 7,211,054 B1 | 5/2007 | Francis et al. | |
| 7,241,267 B2 | 7/2007 | Furia | |
| 7,270,634 B2 | 9/2007 | Scampini et al. | |
| 7,316,655 B2 | 1/2008 | Garibotto et al. | |
| 7,318,806 B2 | 1/2008 | Kohno | |
| 7,488,289 B2 | 2/2009 | Suorsa et al. | |
| 7,662,089 B2 | 2/2010 | Okada et al. | |
| 7,713,190 B2 | 5/2010 | Brock et al. | |
| 7,860,555 B2 | 12/2010 | Saadat | |
| 7,860,556 B2 | 12/2010 | Saadat | |
| 8,199,685 B2 | 6/2012 | Hwang | |
| 9,149,251 B2 | 10/2015 | Steffen | |
| 2001/0023323 A1 | 9/2001 | Nishtala et al. | |
| 2002/0077568 A1 | 6/2002 | Haddock | |
| 2002/0123698 A1 | 9/2002 | Garibotto et al. | |
| 2003/0139677 A1 | 7/2003 | Fonseca et al. | |
| 2003/0199767 A1 | 10/2003 | Cespedes et al. | |
| 2003/0229286 A1 | 12/2003 | Lenker | |
| 2004/0015193 A1 | 1/2004 | Lamson et al. | |
| 2004/0102804 A1 | 5/2004 | Chin | |
| 2005/0090709 A1 | 4/2005 | Okada et al. | |
| 2005/0096642 A1 | 5/2005 | Appling et al. | |
| 2005/0143664 A1 | 6/2005 | Chen et al. | |
| 2006/0106315 A1 | 5/2006 | Edens | |
| 2007/0293724 A1 | 12/2007 | Saadat et al. | |

FOREIGN PATENT DOCUMENTS

| | | |
|---|---|---|
| DE | 19939791 | 2/2001 |
| DE | 19939791 A1 | 2/2001 |

* cited by examiner

Acoustic Specifications
Center frequency = 15 MHz
Number of elements = 23
Element pitch = 0.10 mm
Total azimuth aperture = 2.3 mm
Active elevation = 2.3 mm
Radius of curvature = none

IMAGE GUIDED CATHETERS AND METHOD OF USE

CROSS-REFERENCES

This application is a continuation of U.S. patent application Ser. No. 15/845,756, which is a continuation-in-part of U.S. patent application Ser. No. 14/865,151, filed Sep. 25, 2015, (now U.S. Pat. No. 9,855,021), which is a continuation-in-part of U.S. patent application Ser. No. 13/847,902, filed Mar. 20, 2013 (now U.S. Pat. No. 9,149,257), and a continuation-in-part of U.S. patent application Ser. No. 13/973,476, filed Aug. 22, 2013; U.S. patent application Ser. No. 13/847,902 is a continuation of U.S. patent application Ser. No. 11/871,282, filed Oct. 12, 2007 (now U.S. Pat. No. 8,403,859) and a continuation-in-part of U.S. patent application Ser. No. 11/782,991 filed Jul. 25, 2007 (now U.S. Pat. No. 8,403,858), both of which claim the benefit of the right of priority to U.S. provisional patent application Ser. No. 60/851,451 filed Oct. 12, 2006; U.S. patent application Ser. No. 13/973,476 claims the benefit of the right of priority to U.S. provisional patent application Ser. No. 61/692,443, filed Aug. 23, 2012; and this application claims the benefit of the right of priority to U.S. provisional patent application Ser. No. 62/526,170, filed Jun. 28, 2017; to U.S. provisional patent application Ser. No. 62/527,865, filed Jun. 30, 2017; to U.S. provisional patent application Ser. No. 62/527,905, filed Jun. 30, 2017; and to U.S. provisional patent application Ser. No. 62/590,464, filed Nov. 24, 2017, the disclosures of all priority applications being hereby incorporated by reference into the present application in their entirety.

TECHNICAL FIELD

Embodiments of the illustrated and disclosed aspects and features relate to minimally invasive interventional medical devices having removable and/or reusable components of an ultrasound imaging system and associated channel for introduction of a removeable needle and tools for performing the minimally invasive procedures, and, more particularly, to an ultrasound image guided catheter and methods of use, the catheter elongated housing having a dome-shaped, flat or tapered ultrasound transducer assembly tip at a distal (patient) end, a removable and reusable ultrasound transducer assembly component and a removable and replaceable needle, sheath or tool assembly component. The transducer sensor assembly slidably enters a probe and needle guide housing body and is clasped into a locked position. The ultrasound transducer assembly comprises, for example, a linear phased array at a center frequency of approximately fifteen megahertz (range on ten to forty megahertz) and a pitch between elements of approximately one wavelength (or lambda) (range between 0.85 and 1.15λ or wavelength of center frequency. A conventional pitch of one half lambda or a pitch in the range of 0.5 and 0.6λ or wavelength of the center frequency may be used. The ultrasound transducer assembly is preferably replaceable and reusable with optical coherence tomography or with other assemblies with ultrasound transducers having higher or lower center frequency ranges. The needle or tool assembly may be inserted vertically into a parallel channel of a needle guide, the needle/tool assembly being replaceable with instruments/tools for use at a target site for a medical procedure. The plane of the ultrasound image is mechanically aligned with the needle guide delivery port to ensure that the needle/syringe/tool is visible in the image without the physician needing to make any adjustments to either the imaging array or sheath orientation. In one embodiment, the tool/instrument channel or channels and imaging channel or channels are mounted side-by-side (the needle guide preferably located on top). A patient body region of interest may be visible by the ultrasound transducer assembly from external skin tissue, via a body orifice or subcutaneously. In an embodiment, the needle/tool guide may be mounted above the image guided catheter. Moreover, in other embodiments the needle/tool channel or lumen may extend beyond a transducer window at the distal (patient) end or the transducer window may not extend beyond the needle/tool channel/lumen or lumens.

BACKGROUND

Ultrasound operates by creating an image from sound in three steps—producing a sound wave, receiving echoes, and interpreting those echoes to create an image.

Ultrasound has many uses in medical applications. For example, ultrasound is routinely used during pregnancy to provide images of the fetus in the womb. Generally, a water-based gel is applied to the patient's skin, and a hand-held probe, called an ultrasound transducer, is placed directly on and moved over the patient. The probe typically contains one or a plurality of piezoelectric elements that vibrates and generates a sound wave when a current is applied. In ultrasound devices, the sound wave is typically produced by creating short, strong vibrational pulses using the piezoelectric transducer element. The sound wave is reflected (echoes) from tissues and structures and returns an echo, which vibrates the transducer elements and turns the vibration into electrical pulses. The electrical pulses are then sent to a processor and then to an ultrasound scanner having a display where they are transformed into a viewable analog or digital image on the display. Ultrasound contrast agents (which may be introduced into the blood) are known for enhancing visibility of blood vessels so that smooth needles, sheaths or tools may avoid inadvertent puncture of a vessel. Surrounding human tissue of blood vessels of interest in a particular medical procedure or blood flow may be seen in an ultrasound image. Also, methods for improving the surface echogenicity of tools are known which permit, for example, improved reflection of sound waves back to the ultrasound transducer assembly.

While general-purpose ultrasound machines may be used for most imaging purposes, certain procedures require specialized apparatus. For example, in a pelvic ultrasound, organs of the pelvic region can be imaged using either external or internal ultrasound devices used together or in combination with ultrasound image guided catheters of the present invention (implanted or inserted, for example, via the rectal opening, the mouth, a vein or other useable openings to a human body). In contrast, echocardiography, which is used in cardiac procedures, can require specialized machines to take into account the dynamic nature of the heart.

Ultrasound has advantages over other imaging methods such as magnetic resonance imaging (MRI) and computed tomography (CT) or optical coherence tomography (OCT), but these, along with known X-ray imaging can be used together to gather displayed images of a patient's region of interest. Ultrasound produces a sequence of images in real time and so, for example, a mother may see the ultrasound image of her baby and see the baby's heartbeat. Also, ultrasound is relatively inexpensive compared to techniques such as MRI and CT. Ultrasound also is capable of imaging muscle and soft tissue very well, can delineate interfaces between solid and fluid filled spaces (for example, for cardiocentesis procedures with a pericardial sac), and may show the structure of organs and their internal components (such as a heart valve). Ultrasound renders live images in real time in sequence and can be used, for example, to view blood vessels in relation to the operation of organs in real time (with or without contrast). Ultrasound has no known long-term side effects and generally causes little to no discomfort to a patient. Further, ultrasound equipment is widely available, flexible and portable.

However, ultrasound does have some drawbacks. When used on obese patients, image quality is compromised as the overlying adipose tissue scatters the sound and the sound waves are required to travel greater depths, resulting in signal weakening (attenuation) on transmission and reflection back to the ultrasound transducer (especially a surface-mounted ultrasound system). Even in non-obese patients, depth penetration is limited, thereby making it difficult to obtain images of structures located deep within the body. Further, ultrasound has trouble penetrating bone and, thus, for example, ultrasound imaging of the brain within skull bone is limited from external to animal bone. Ultrasound also does not perform well when there is gas present (as in the gastrointestinal tract and lungs). Still further, a highly skilled and experienced ultrasound operator is necessary to obtain quality images. These drawbacks do not, however, limit the usefulness of ultrasound as a medical diagnostic and treatment tool.

The use of ultrasonic apparatus for imaging areas of the human body, either alone or in combination with other instruments, is known, for example, for guiding therapeutic instruments through a catheter to a field of view within a human body. For example, ultrasound devices have been combined with catheters for insertion into a body, usually through a vein or artery, to reach a part of the human body for examination or treatment. Such devices are commonly known in the art as "imaging catheters."

For example, U.S. Pat. No. 5,704,361 to Seward et al. discloses a volumetric image ultrasound transducer under-fluid catheter system. For example, FIGS. 2-9 and 11-12 of Seward et al. and their attendant description suggest specific methods of intervention for imaging purposes in the vicinity of a human heart. To reach such an area of interest within a human body, an ultrasound imaging and hemodynamic catheter may be advanced via the superior vena cava to a tricuspid valve annulus. A distal end of a cylindrical body includes a guide wire access port and a guide wire provides a means of assuring that the catheter reaches a target for imaging. A surgical tool may be fed through the catheter to the area imaged.

U.S. Pat. No. 6,572,551 to Smith et al. provides another example of an imaging catheter. Tools such as a suction device, guide wire, or an ablation electrode, may be incorporated in an exemplary catheter according to Smith et al.

U.S. Pat. No. 5,967,984 to Chu et al. describes an ultrasound imaging catheter with a cutting element which may be an electrode wire or a laser fiber. FIGS. 1 and 2 of Chu et al. also describe a balloon 14 and a means to inflate the balloon. The balloon, for example, may be utilized to dilate a vessel having strictures imaged via the imaging catheter.

Other imaging catheters are known. For example, U.S. Pat. No. 6,162,179 to Moore teaches bending (using a pull wire) an acoustic window into a known and repeatable arc for improved three-dimensional imaging. U.S. Pat. No. 6,306,097 to Park et al. discloses an intravascular ultrasound imaging catheter whereby a first lumen provides access for an ultrasound imaging catheter and a second lumen provides a working port for a tool. U.S. Pat. No. 5,505,088 to Chandraratna et al. teaches using a 200 MHz transducer in an ultrasonic microscope combined with a catheter as a delivery means for the microscope to provide imaging of myocardial tissue. According to Chandraratna et al., lower frequency ultrasound transducers can provide deeper penetration in the tissue but do not provide the image quality provided by higher frequencies.

Optical coherence tomography (OCT) operates in a similar manner to ultrasound in producing an image having high resolution but the transmitted light signal reaches only so far into human tissue. White light diodes covering the visible spectrum may be used to transmit light through, for example, a transparent window to the human tissue, and the echo is received and passed to a display which may create a three-dimensional image. Near infrared and other radio frequencies, visible and invisible, may be applied to create an image of human tissue at, for example, a site of a medical procedure.

Needle guides are known for probes and catheters. Typically, a needle guide may be located at the top of the probe or catheter and provide a channel having a diameter for a specific needle size. The needle may be inserted subcutaneously with or without imaging by sliding the needle from the surgeon end through the needle channel. Also, the needle guide is in one piece and incapable of being opened to release the needle from the probe or catheter. The needle is removed by pulling the needle through the needle channel toward the surgeon end, and the needle may capture debris or fluid such as blood at the needle channel tip as the needle is pulled out of the needle channel.

All the above-cited references are incorporated by reference as to any description which may be deemed essential to an understanding of illustrated and discussed aspects and embodiments of devices and methods herein and as summarized below.

SUMMARY OF THE EMBODIMENTS

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

In an image-guided catheter such as represented by U.S. Pat. No. 9,149,257 entitled "Image Guided Catheters and Methods of Use" issued Oct. 6, 2015 (the '257 patent) by the same inventor, per FIG. 3A, an ultrasound beam generated by a transducer element 210 of an ultrasound imaging channel 214 provides a cone-shaped imaging zone 301 which can display a needle 208 directed parallel to the ultrasound beam and located within a sheath or lumen or plurality of lumens. (The '257 patent should be deemed to be incorporated by reference as to its entire contents). One the other hand, the needle 208, (sheath or tool) being parallel to the cone-shaped ultrasonic beam, may be difficult to see in the imaging zone 301 because the needle, sheath or lumen is very thin in diameter, may comprise a smooth surface, and may extend in the same direction as the ultrasound beam is projected (parallel to the sonic beam) from the thin, minimally invasive image-guided catheter so that the sonic beam will tend to follow the angles of impingement and reflection and are intended to project from the needle, sheath or tool in a direction deeper into, for example, a human body in which the image guided catheter of FIG. 3A is inserted. Also, it is desirable to visualize the needle, sheath or tool itself to determine the direction of its movement within the human body from the point of entry of the human body to an area of interest such as the human heart, the liver or other organ of interest. In one embodiment, the needle or sheath may be hollow (in another, solid) and may be removed once the catheter is located at a site of interest and replaced in real time with a tool. In another embodiment, the tool may be used simultaneously (in its own lumen) with the needle or sheath to bend or guide the needle or sheath to the region of interest from a patient's skin surface.

The following additional U.S. patents and published applications of Dr. Theodore Abraham should be deemed to be incorporated by reference as to their entire subject matter and refer to similar image guided catheters, implanted ultrasound devices, wired or wireless ultrasound devices and the like which may receive signals from echogenic needles, sheaths or tools and surrounding tissue or blood: U.S. Pat. No. 8,038,622 issued Oct. 18, 2011; U.S. Pat. Nos. 8,147,413 and 8,147,414, issued Apr. 13, 2012; U.S. Pat. Nos. 8,403,858 and 8,403,859 issued Mar. 26, 2013, and U.S. 2016/008,1658 published Mar. 24, 2016.

A device in accordance with one or more aspects described herein may include ultrasound imaging using a conventional piezoelectric linear or phased array transducer or a more recently developed photo-acoustic transducer (light transmit, sound receive) providing high resolution imaging or optical imaging through the use of fiber optics, i.e. using optical coherence imaging, through an additional channel or lumen than a single ultrasound channel and a single needle/instrument channel, or a combination of these, to provide a wide range of imaging capabilities coupled with one or more diagnostic, therapeutic, or interventional capabilities. In one or more embodiments, according to aspects herein, an interventional ultrasound device preferably may include an expendable housing (useful for one minimally invasive medical procedure) while the ultrasound assembly may be reusable. An optional handle for the use of a surgeon may help the surgeon guide the progress of the device as its distal end progresses into a human body subcutaneously or into a body orifice (as necessary). The image guided catheter device may have a proximal end (the surgeon end) and a distal end, a first lumen, also referred to as an imaging lumen or channel, for holding a replaceable imaging ultrasound transducer assembly of varying center frequency (for example between ten and forty megahertz) and a second lumen which may extend to a distal end or short of the distal end of the expendable housing, also referred to as a needle/instrument lumen, for, for example, a needle guide and for replacing a removable needle or sheath with another interventional device such as a cutting and grasping instrument, sheath or syringe (referred to generally herein as a tool). The imaging transducer assembly may be adapted to removably fit into the imaging lumen at the distal (patient) end of the housing. The transducer assembly may be removed, reused, and/or replaced with imaging transducer assemblies having ultrasound transducers of higher or lower frequency ranges or OCT assemblies and adapted to be used for different purposes in real time, for example, during a medical procedure or comprise additional lumen, for example, for optical coherence tomography imaging or with other ultrasound devices which may be surface-mounted or implanted.

Illustrative aspects described herein include a minimally invasive interventional medical device that can provide ultrasound imaging coupled together with one or more interventional capabilities. The ultrasound frequencies present in a sound wave output by such a device can range between twenty kilohertz and several hundred megahertz or ultrasound frequencies in the gigahertz range. Frequencies in the lower range, for example, below one megahertz, and particularly in the 100-200 kilohertz range, can be used, for example, to provide heat therapy or to treat conditions such as blood clots and provide low resolution, long range imaging. Frequencies above one megahertz can be used to provide higher resolution imaging at shorter range. For example, ultrasound frequencies in the 25 to 30 megahertz range can be used to image organs such as the eye or can be used to provide imaging of small animals. Higher frequencies, for example, ultrasound frequencies in the one hundred to several hundred megahertz range, can be used to provide even higher-resolution imaging, sometimes known as high-frequency ultrasound microscopy, at a target site within a body undergoing a medical procedure. A feature of the imaging channel of an embodiment of the present invention is that the ultrasound transducer may be replaceable during a medical procedure to provide imaging for any of these purposes during the procedure via replacement of a replaceable and reusable ultrasound transducer and cabling module, for example, with one of higher center frequency and greater resolution including optical coherence tomography imaging or the use of a plurality of optical fibers. Center frequencies for ultrasound imaging via a linear phased array may vary from ten to forty megahertz and have a sufficiently small diameter for subcutaneous or body orifice use (ear canal, nasal cavity, throat or rectum). In embodiments not shown, more than one imaging lumen/channel may be used at a time during a medical procedure if provided in an embodiment of an image guided catheter.

An embodiment of a device in accordance with one or more aspects and features described herein can include a reusable, removable ultrasonic imaging device assembly or module having one or more forward-directed ultrasound transducers, for example, comprising a linear phased array or comprise optical fibers or optical coherence tomography that can be inserted into a distal (patient) end of an expendable catheter housing by way of a lengthwise slot in the proximal end of the housing so as to provide access to the distal end (lumen) of the housing from which, when the ultrasonic or other imaging device assembly is moved forward into the distal end and operated, a direct forward view forming an imaging zone of the tissue being accessed comprising a pie-shaped cross section may be obtained from the ultrasonic or other imaging device assembly and displayed on a display. The imaging zone of the ultrasound transducer may be seen through a dome or window (which may be transparent) of a probe housing assembly having an openable needle guide. An introducer needle may be used during introduction of the device subcutaneously or the probe end be simply used external to the human body or in an orifice of the human body followed by its replacement with an interventional device or instrument introduced via a needle guide, for example, to cut and remove unwanted tissue, a biopsy needle to gather a tissue sample, a syringe to remove unwanted liquid or a sheath to permit a repair or replacement of a heart valve.

An embodiment of a device in accordance with one or more aspects and features described herein may comprise a minimally invasive image guided catheter device having a removable, replaceable introducer needle, sheath or instrument (tool) assembly in the needle/instrument lumen and then the one or more replaceable forward-directed ultrasound transducer or optical assemblies that can be inserted and moved forward into the imaging lumen of the single expendable housing via the lengthwise slot at the proximate end so that the introducer needle, sheath or instrument and the imaging catheter (expendable) housing along with the replaceable transducer assembly can be introduced into a body substantially simultaneously via one or more proximate channels. The introducer needle, sheath (or instruments replacing the needle or sheath), the distal tip of the housing and the path taken by the needle or sheath can be viewed within the imaging zone of the replaceable transducer assembly as the entire assembly comprising transducer assembly, housing and instrument/syringe/needle/sheath/tool assembly components may travel through an animal/human body subcutaneously to a target site for a medical procedure or be simply used at skin surface or inserted via a body orifice. A solid or hollow needle, syringe, sheath or other tool may be replaced in the needle channel with medical instruments or carriers of replacement body parts such as heart valves when the operating site via the sheath is reached.

An alternative embodiment of a device (shown in priority patent applications and issued patents and published applications of the inventor introduced above) in accordance with aspects described herein can have one or more ultrasonic transducers located along one or more sides of the image guided transducer assembly and housing to obtain peripheral views of the body tissue under medical procedure. The replaceable imaging transducer assembly and removable introducer needle or sheath assembly may comprise a forward-directed ultrasound transducer imaging assembly operating within, for example, a first and second, sonic or optical predetermined range of ultrasound/optical frequencies to enter the human body, then guide the entire image guided catheter to the target site of a medical procedure and provide high resolution (high frequency or optical coherence or both) imaging at the target site of a medical procedure. A tool such as a clasper or microelectromechanical motor system may be introduced to help guide the sheath or needle upwards or downwards to reach the site of interest or may replace the needle or sheath when located at the site of interest, for example, to repair or replace a heart valve.

The ultrasound features of the device can serve to guide and facilitate surgical procedures performed with the image guided catheter device. For example, a medical professional such as a surgeon can receive direct high-resolution vision of a targeted area in real time. The lumen for example, for receiving a syringe or surgical instrument and introducer needle assembly may have inserted and locked into place therein, a hollow syringe needle for withdrawing unwanted fluids or tissue specimens or a tapered solid needle for, for example, skin penetration and internal body wall puncture may be used when needed via the tool replacement feature and multiple usage of a single instrument lumen or channel or used together with a tool in a second parallel lumen and visioned by ultrasound or OCT or other imaging channel.

A wide variety of other interventional elements also can be incorporated into such a device. Examples of replacements for a syringe/needle assembly in the needle or sheath lumen may include a syringe for removing fluids, an instrument having a biopsy needle for extracting tissue specimens, an instrument including a biopsy blade, an instrument carrying a micro-motive electronic manipulator (MEMS) device, an instrument comprising a clasper for cutting and clasping tissue for removal and other instruments as described in priority patent applications and issued patents. A syringe needle may be hollow or solid and may be used as an introducer needle or larger diameter sheath for another device and for delivering medication or for removing unwanted fluid (for example, unwanted fluid in the pericardial sac or space).

For example, in some embodiments of a device in accordance with one or more aspects and features described herein, an ultrasound imaging transducer assembly can be combined with an interventional catheter having an introducer needle so that the catheter distal end can be inserted under ultrasound imaging guidance directly into the target site (the proximal end being held by a handle and used by medical personnel to grasp the assembled image guided catheter device with one hand while replaceable needles, tools, transducers of different frequencies, optical fibers and the like are inserted in the two or more channels to the distal end). For example, the image guided catheter can be inserted directly through the chest wall, guided to a heart and then into the heart using the introducer needle without having to make entry through another means such as through a blood vessel in a human leg or other vein or by using a guide wire as is taught with prior art devices. If necessary, an ultrasound transducer assembly having a longer range and lower resolution may be replaced in real time during the movement of the image guided catheter assembly with a higher resolution and shortrange transducer assembly as the target site is reached or used with a high resolution short range optical coherence tomography or plurality of optical fibers or other known vision device. Once at the target location for a medical procedure, the removable needle or sheath may be removed and replaced with another instrument such as a biopsy needle, MEMS device, tissue clasper or biopsy blade among other instruments (tools).

In another embodiment in accordance with one or more aspects herein, a medical device is provided that can comprise one or more ultrasound transducers coupled or associated with a syringe element for delivery of medication or withdrawal of unwanted fluids at a treatment site. An exemplary syringe that may be used to replace an introducer needle assembly once the device is at the target site is a needle assembly such as is described in U.S. Pat. No. 6,592,559 to Pakter et al., which may deliver multiple needles to multiple sites within the body at the target site.

A MEMS device may be deployed via the distal end to help guide upwards or downwards the needle, syringe or sheath as the catheter is surgically moved towards a site of interest. Furthermore, a tool may replace a solid or hollow needle, syringe or sheath once a site of interest is reached using the needle guide.

According to other aspects, at the proximal end of such a device, an anchoring portion may be provided for anchoring the device to a human body once the device is image-guided to the diagnosis or treatment site or alternatively the device may be manipulated by a handle grasped in one hand by the surgeon. The proximal end may also include locking mechanisms for securing the removable, replaceable imaging transducer assembly and/or a replaceable syringe with another medical device or instrument of the expendable housing component while the image catheter device is in use during a medical procedure.

According to aspects herein, the housing of such a device may be formed from one or more of a variety of materials such as silicone. Teflon, polyurethane, PVC, TPX, and/or elastomeric hydrogel. According to some aspects, the housing may be cylindrical in shape and may include, for example, a catheter or vascular sheath. As will be shown herein, the needle/instrument channel and an ultrasound transducer channel may be mounted side by side one another or one on top of the other. The expendable housing may be tapered at the distal (patient) end or have a dome or a window that may be flat and transparent for the ultrasound transducer, optical coherence tomography or plurality of optical fibers, once inserted in the imaging transducer channel/lumen or in its own lumen. According to some aspects, the ultrasonic probe housing may have a lengthwise slot opening at the proximal cross-sectional side allowing its user to freely remove and replace the replaceable imaging transducer assembly while the image guided catheter device is being used during a minimally invasive medical procedure.

According to aspects herein, the imaging transducer assembly may comprise a forward viewing linear phased array probe with a variable field of view depending on the specific array and choice of center frequency and frequency range. The imaging transducer assembly may comprise a plurality of ultrasound transducers at the distal end with variable frequency, variable cross-sectional diameter, and a variable number of transducer elements located in a steel or rigid plastic cylinder with a varying outer diameter, for example, wherein the expendable housing may have two or three different outer diameters during its length from a large outer diameter surgeon grasp and optional handle at the proximal end of the expendable housing to a very small outer diameter at the distal end, typically referred to herein as the barrel having a small diameter for just the imaging and instrument channels/lumens.

According to aspects herein, the syringe/needle assembly/instrument lumen may fit a removable variable gauge solid introducer needle, a hollow syringe needle, a sheath or other interventional instruments as discussed above once the operating target site is reached. The needle, sheath or tool may be echogenic and comprise a variegated surface by sanding, engraving, etching or wrapping wire of non-allergic material round the catheter needle or sheath or tool.

These and other aspects of embodiments of an image guided catheter assembly will be discussed with reference to the drawings, a brief description of which follows.

In the brief description of the drawings, for drawings FIG. 1A through FIG. 12I, similar reference numerals are used to denote similar elements and the first numeral of a reference numeral such a 1XX denotes the figure in which the element first appears, in this case, FIG. 1. Also, the XX portion of a reference numeral is intended to refer to a similar component in each figure.

BRIEF DESCRIPTION OF THE DRAWINGS

The drawings are exemplary and are not intended to limit the dimensions of the depicted elements to those shown in the drawings. All dimensions may vary with the particular application of the image guided catheter or probe depicted in the several drawings.

FIG. 1A through FIG. 6B depict a disposable assembly comprising a needle guide, and a tab which may be moved circularly round the elongate probe housing to close one half of the needle guide onto the other half so that a needle (or syringe or other tool) may be placed vertically into the open needle guide, the needle guide closed about the tool and the tool removed therefrom, for example, vertically, a probe barrel containing an ultrasound transducer section and a disposable sheath section which has a locking tab. A second assembly, not introduced until

FIG. 1A depicts a view of a patient or distal end of an image guided catheter device assembly in accordance with one or more aspects described herein. FIG. 1A showing a replaceable introducer needle/syringe/instrument channel 103 above a transducer sensor tip channel 105, the needle/tool guide 103 having a tapered distal tip 104. When a needle protrudes from this distal tip 104, the needle is visible in an imaging zone (not shown) of the removable, replaceable transducer element or array within the probe distal end 105 replaceable, for example, as higher resolution is needed when the access instrument reaches the operating site. A tab 106 is shown for use by a surgeon to open or close the needle guide 103 for insertion of a needle/syringe or other tool. Body or sheath 102 may comprise additional lumen or channels and may comprise a sensor channel or lumen 105 for additional needles/tools (not shown) and may contain leads to the transducer array behind tip 105 that form a cable to a processor and display (not shown). A locking tab 101 is provided for permitting insertion of a probe, transducer and cable assembly which may comprise a linear phased array transducer assembly having a collection of leads to each piezoelectric element which form a cable (not shown) but exiting at the rear of sensor channel 102 to a section first shown in FIG. 9A. Button tabs 107 and 108, when needle guide 103 is in an open position, serve to push up on a needle, syringe or tool in the needle guide 103 so as to release it (for example, if the needle comes in contact with a sticky substance such as coagulated blood). Tab 106 will be seen to be used to lock two halves of needle guide 103 together.

FIG. 2B shows additional button tabs 209, 210 which may be used or not used in a given embodiment to further serve to support a needle/syringe/tool in needle channel tabs (FIGS. 1B and 1C). Needle channel tip 204 is tapered and may receive and permit a tapered tip hollow needle (possibly of a syringe) to exit the needle guide at tip 204. Sensor channel tip 205 may indicate the location of an ultrasound sensor not seen which may be directed forward and provide forward-imaging of a needle/syringe/tool in the needle channel 203. In either figure, a rear tab 101, 201 may lock a sensor and cable section assembly in place within the body 202 comprising a sensor channel (transducer assembly and cabling). Needle 1010 and sensor and cable assembly 1006 are first seen in FIG. 10 locked in place by locking tab 1001.

In FIG. 3A, the needle channel tip 304A is shown closed.

FIG. 4A represents a closed needle channel and FIG. 4B represents and open needle channel, for example, where partial circular sections connected to tab 106 comprise line 420 along which the needle channel opens. FIG. 4A comprises closed needle channel tip 404A, the first part 421A of the closed needle channel, the second part 422A of the closed needle channel, and the sensor channel tip 405 of the ultrasound sensor channel. Referring to FIG. 4B, sensor channel tip 405 is in the center. Surrounding this center 405 are open needle channel tip 404B, open second part 422B of the needle channel and open first part 421B of the needle channel. Section C-C is taken just of the probe housing as seen in FIG. 1A.

FIGS. 6A through 12I show an embodiment similar to the previously discussed embodiment whereby a sleeve lock is used to lock two halves of a needle channel of a needle guide together around an inserted tool: for example, a needle, syringe or other tool.

FIGS. 6A and 6B depict front perspective views of the line 620 along which the needle channel 603 opens along with a portion of the sensor housing or body 602. Referring to FIG. 6A needle channel 603A is in a closed position, the first part of the needle channel 621A is closed as is the second part (for example, half) of the needle channel 622A. Referring now to FIG. 6B, the needle guide is in an open position 603B and the first and second parts 621B and 622B (for example, halves) of the needle channel are opened.

Thus far, we have discussed how a tab 106 may open and close a needle channel. In FIGS. 7A through 8H and in FIG. 9A an alternative to a tab closure is shown that comprises a sliding groove 724 moved by a surgeon via a circular or partially circular tab or sleeve lock 723 with unnumbered finger grips seen as rounded gripping ridges on the sides of the sleeve lock 723.

FIG. 7A shows sensor housing channel 702 and the needle channel 703 in a closed position where the circular tab or sleeve lock 723 and groove 725A have been slid forward to clasp the two halves of a needle guide 703 together. The groove may have parallel sides shown or have V-shaped clasping sides. The parallel sides 721 and 722 (FIG. 7B) of groove 724 may have a corresponding quarter-circular portion 725A which gathers the two sides 721, 722 of the needle guide together, and the groove 724 holds the needle guide together. A retaining spring tab 712 retains the sleeve lock so as to close the needle channel 703 of the needle guide.

FIG. 8H provides a rear expanded perspective view of the closure of needle guide 803 (Detail C) having halves 821 and 822 within a groove 824 of sleeve lock 823 having a quarter-circular section 825A for matching with needle guide quarter-circular section 825 along closure line 820.

FIGS. 9A through 9I provide views of a combination assembly of the sensor housing and needle guide section with the sensor and cabling section using the groove needle guide locking mechanism or sleeve lock 923 as discussed above. Alignment of the imaging plane 919 (or zone of reflected imaging) with the needle delivery port of the needle guide 903 permits ultrasound visibility of the needle/syringe/tool or other device within the imaging plane when these are introduced subcutaneously into a patient.

FIG. 9A provides a top view of the combination assembly comprising from left to right sensor channel tip 905 with a needle guide tip directly above but not easily discernable. Sensor channel 902 holds, for example, a probe comprising a linear phased array with each element connected to leads of a cable (not seen) until the cable exits at right as cable 906A. An imaging plane or zone is seen surrounding the linear phased array within a range around the center frequency. Alignment of the imaging plane with the needle delivery port portion of the sheath permits ultrasound display of an emerging needle/biopsy needle/syringe/other tool of needle guide 903. Needle guide 903 is shown closed within a groove of circle B. Gripping tab 923 that may slide back is shown closed and retained by retaining tab 912 so that a groove closes needle guide 903. Next to the right is disposable sheath 909 and a cable joining section 906B of a probe, probe housing and cable assembly.

FIG. 9B is a cross-section along line A-A of FIG. 9A so as to see the internal components of the combination assembly. A right-side cross-section of the assembly comprises from right, cable 906A which merges with cable joining section 906B and the individual piezoelectric element leads (from each element may be combine to form a cable) may pass through sections 906B and 906C (a probe section) to, for example, a linear phased array of elements facing forward at sensor tip 905. Tab 901 locks needle guide section 902, 903, 904, 907, 908, along with cable section disposable housing 909 to the internal cable and sensor sections 906A, 906B and 906C.

FIG. 9C is a further exploded top view (Detail B) of the needle guide locking mechanism comprising along closing line 920 a first quarter-circular groove section 925A and an opposite quarter-circular grove section 925B of groove 904 of sleeve lock 923 which close around needle guide halves 921 and 922 to close the needle guide 903.

FIG. 9D is a complete assembly side view comprising from left to right a sensor tip 905, a sensor housing 902, needle guide button tabs 907 and 908 and needle guide 903. The sleeve lock 923 is seen in a closed position so that needle guide 903 would be closed. Disposable plastic sheath 909 is seen next with tab 901 holding sensor and cable assembly 906A and 906B in place, mostly internally within the housings 902 and 909.

FIG. 9E provides a front perspective view of the entire assembly. Starting from left is seen the sensor housing tip 905, the probe housing 902, needle guide button tabs 907, 908, the needle channel 903 with sleeve lock 923 having quarter-circular section 925A for locking the needle guide 903 in a groove of sleeve lock 923 in a closed position (Circle D discussed in FIG. 9F) held by retaining tab 912, disposable plastic sheath section 909 (covering cable) and ultrasound sensor and cable sections 906B and cable 906A may be seen. When sleeve lock 923 is moved to the rear opening the needle channel 903 via the sleeve lock 923, the sleeve lock 923 is retained by a retaining tab on the bottom of sheath 909. A forward-directed linear phased array would be located just behind sensor tip 905, and the array provides an imaging plane which may be aligned with the needle guide delivery port portion of the sheath of the needle guide 903 for displaying in real time a position of a needle/syringe/tool emerging from the needle guide and used subcutaneously. An approximately two-dimensional ultrasound imaging plane 919 is shown to be oriented perpendicular to the face of the ultrasound array to the center of the needle port delivery port portion of the sheath; (see also FIG. 9I). This ensures that during a procedure the needle or other tool emerging from the needle guide 903 at its distal port is automatically visible in the ultrasound image without the physician needing to adjust the relative orientation of a sheath or ultrasound probe.

FIG. 9F provides a front perspective view of the needle guide locking mechanism in a closed position along line 920 (Detail D). Sleeve lock 923 locks needle guide halves 921 and 922 together in a groove 924 having a quarter-circular section 925A and a rear groove face 926A and is retained in closed position by retaining tab 912 (FIG. 9E).

FIG. 9G provides a rear perspective view of the combination assembly from left to right comprising the sensor housing tip 905, the probe housing 902, needle guide button tabs 907, 908, the needle channel 903 with sleeve lock 923 having quarter-circular section 925A for locking the needle guide 903 (in circle C) in a groove of sleeve lock 923, disposable plastic sheath section 909 (covering cable) and ultrasound sensor and cable sections 906B and cable 906A may be seen along with tab 901 for holding the outer housing together with the probe and cable assembly. A forward-directed linear phased array would be located just behind sensor tip 905 and the array provides an imaging plane 919 which may be aligned with the needle guide delivery port portion of the sheath of the needle guide 903 for displaying in real time a position of a needle/syringe/tool emerging from the needle guide and used subcutaneously.

FIG. 9H is an exploded view of Detail C where needle guide halves 921, 922 of needle guide 903 are held together by a groove 924 of sleeve lock 923.

FIG. 9I is very similar to FIG. 8I and shows a cross-section of the disposable plastic sheath portion 909, the needle channel tip and the sensor channel tip 905, the needle channel tip being the end portion of the needle guide 903. The exact orientation of the ultrasound image plane 919 is shown to intersect the center of the imaging array and needle delivery port, thereby ensuring that the needle or other tool being delivered will be visible in a processed ultrasound image (not shown) without the physician having to adjust the relative position of the sheath or ultrasound probe.

FIG. 10A shows section A-A seen in FIG. 10B. FIG. 10A from left to right includes but is not limited to showing needle tip 1011, closed needle guide 1003, sleeve lock 1023, needle handle 1010, circle B for explaining the locking mechanism, disposable plastic sheath section 1009; letter A where the clasp 1001 would be located on the underside and is not visible, cable narrowing section 1006B and cable section 1006A. Needle handle 1010 may comprise a syringe.

FIG. 10B shows section A-A comprising from left to right a needle tip 1011, button tabs 1007 and 1008 which assist in lifting needle 1011 (or other tool) vertically out of the needle channel 1003, sensor tip 1005, probe 1006C, piezoelectric element signal leads 1002 (from array elements to form a cable), needle handle 1010, locking tab 1001 in the vicinity of A of FIG. 10A, cable narrowing section 1006B and cable section 1006A from which a cable exits a proximal end toward a processor and display (not shown).

FIG. 10C provides an expanded view of detail B (circle B of FIG. 10A) showing the needle channel halves 1021, 1022 in a locked position in groove 1024 having been guided into groove 1024 by quarter-circular edges 1025A. 1025B of the distal end of groove 1024. FIG. 10C also shows needle handle 1010 and a top viewable portion of locking sleeve 1023.

FIG. 10D is a side view of a complete assembly including both a probe and cable housing portion 1005, 1002, 1009, a locking sleeve 1023 held in a closed position by retaining tab 1012, a needle 1011 and handle 1010 held in needle channel 1003 by button tabs 1007, 1008 and a disposable sheath 1009 having a retaining tab 1001 for securing a cable and probe section 1006A, 1006B. Retaining tab 1013 stops sleeve lock 1023 from moving rearwards along sheath 1009.

FIG. 10E provides a front perspective view of a complete assembly as seen in FIG. 10D comprising four components, a needle 1011 and needle handle 1010, the needle residing in a needle channel 1003 of a needle guide, the needle 1011 supported by button tabs 1007 and 1008 of the needle guide portion of a probe and cable housing comprising the needle guide, a distal probe tip window 1005, a probe housing 1002 and a disposable sheath 1009 having a locking tab 1001 for locking, for example, a probe containing a linear phased transducer array located behind the window 1005, and element leads to a cable exiting the sheath 1009 via cable narrowing section 1006B while cable 1006A leads to a processor and display (not shown) and the sleeve lock 1023 which is slid down sheath 1009 and over retaining tab 1012 to close needle channel 1003 over needle 1011. Circle D will be discussed with reference to FIG. 10F.

FIG. 10F provides an expanded view of detail D (circle D of FIG. 10E) showing the needle channel halves 1021, 1022 in a locked position in groove 1024 having been guided into groove 1024 by quarter-circular edges 1025A, 1025B (not visible) of the distal end of groove 1024 joining the two halves 1021, 1022 of needle channel 1003. FIG. 10F also shows needle handle 1010 and a top viewable portion of locking sleeve 1023.

FIG. 10G provides a rear perspective view of a complete assembly as seen in FIG. 10D comprising four components, a needle 1011 and needle handle 1010; the needle 1011 residing in a needle channel 1003 of a needle guide, the needle 1011 supported by button tabs 1007 and 1008 of the needle guide portion of a probe and cable housing comprising the needle guide, a distal probe tip window 1005, a probe housing 1002 and a disposable sheath 1009 having a locking tab 1001 for locking, for example, a probe containing a linear phased transducer array (not shown) located behind the window 1005, and element leads to a cable exiting the sheath 1009 via cable narrowing section 1006B while cable 1006A leads to a processor and display (not shown) and the sleeve lock 1023 which is slid down sheath 1009 during assembly and over retaining tab 1012 to close needle channel 1003 over needle 1011. Circle C will be discussed with reference to FIG. 10H.

FIG. 10H provides an expanded view of detail C (circle C of FIG. 10G) showing the needle channel halves 1021, 1022 in a locked, closed position in groove 1024 having been guided into groove 1024 by quarter-circular edges 1025A, 1025B (not visible) of the distal end of groove 1024 joining the two halves 1021, 1022 of needle channel 1003. FIG. 10H also shows needle handle 1010 and a top viewable portion of locking sleeve 1023.

FIG. 10I is very similar to FIGS. 8I and 9I but differs in showing needle tip 1011 emerging from needle guide 1003 and shows a cross-section of the disposable sheath portion 1009, the needle channel tip 1004 and the sensor channel tip 1005 with the end portion of the needle guide 1003.

FIG. 11C also shows needle handle 1111 and a top viewable portion of locking sleeve 1123.

FIG. 11C also shows needle handle 1110 and a top viewable portion of locking sleeve 1123.

FIG. 11H also shows needle handle 1110 and a top viewable portion of locking sleeve 1123.

FIG. 11I further shows cross-section 1109 of disposable sheath 1109 and the probe window or distal probe housing end 1105.

FIGS. 12A through 12I are identical to FIGS. 11A through 11I but for the movement of needle 1211 (or other tool) and handle 1210 (or syringe portion) vertically out of the needle channel 1203 and will not be described in any detail to avoid redundancy. However, FIG. 12I will be briefly explained as it shows the needle 1111 removed from the channel vertically.

FIG. 12I shows needle handle 1210 and needle 1211 removed vertically and outside the open needle channel comprising open needle channel halves 1221 and 1222. Probe distal end 1205 is seen as is the sheath section 1209 in cross-section.

FIGS. 13 through 17B provide an overview of the insertable probe, cable and linear phased array transducer assembly 1006A, 1006B, 1106C, that is locked by locking tab 101, 201, 501, 801, 901, 1001, for example, inside disposable sheath 102, 202, 502, 909, 1009, for example.

FIG. 13 present provides a side view at its center of a plurality ultrasonic elements (not visible) of a transducer probe according to the present invention which may have a protective sheath (not shown) disposed between the probe 1361 located toward the distal tip 1360. All distances if any are shown are approximate and may be changed for different applications such as reaching the heart pericardial sac (also known as the pericardial space) versus reaching a melanoma close to the skin or a kidney with an anterior approach with optimized resolution and are shown in millimeters. A convention used in the brief and detailed description is that a reference numeral YXX may be used wherein the Y provides the Figure number where the element first appears and the XX (which may be any two-digit number) may represent the reference numeral of the element (used consistently for a similar component), for example, transducer array 1362 comprises Y for FIG. 13 and XX for numeral 62 which represents the transducer array while element 1310A represents the cylindrical housing 1310A shown in FIG. 12 held within disposable sheath, for example, 1109 by a surgeon (not shown in this figure series). To the left of FIG. 13, is seen a cross-section of a plane of housing 1310A including both the probe 1361 and the cylindrical housing 1310A. At the right of FIG. 13 is shown a cross-section 1340 intended to show the radially placed elements of the outer cylindrical housing 1310A, cable transition portion 1206B, the strain relief feature and the cable 1206A including, for example, the twenty-three leads to the transducer linear phased array, shown by way of example, which in turn leads to a display processor and display. Views 1361, 1362, 1316 are shown enlarged as FIGS. 14A (end view) and 14B (cross-sectional top view) of exemplary linear phased array elements 1462-1 through 1462-23.

FIG. 16 provides either a top-down view or a bottom-up view of the image guided probe at the center of FIG. 13 (without showing details of any sheath for protecting the probe so that the probe housing is reusable). The view shows the probe 1350's distal end 1360 where would be located the linear phased transducer array 1462 of the present invention. The center section is the cylindrical housing 1310A that is covered by a disposable sheath that may be grasped and utilized by a surgeon. The section transition feature 1315 provides a side view of an example transition between the probe's cylindrical cable housing 1310A and the cable strain relief feature 1306B which provides the exit of cable 1306A from the imaging probe for image processing and display.

FIG. 17A is a left front perspective view of an image guided probe comprising distal probe end 1360, probe shaft 1350, cylindrical housing 1310A, transition feature 1315, flexible cable section 1306B and cable 1306A from left to right.

FIG. 17B is a right rear perspective view of an image guided probe showing the same components in the same order as is seen in FIG. 17A from upper left to lower right.

Figure 1A:
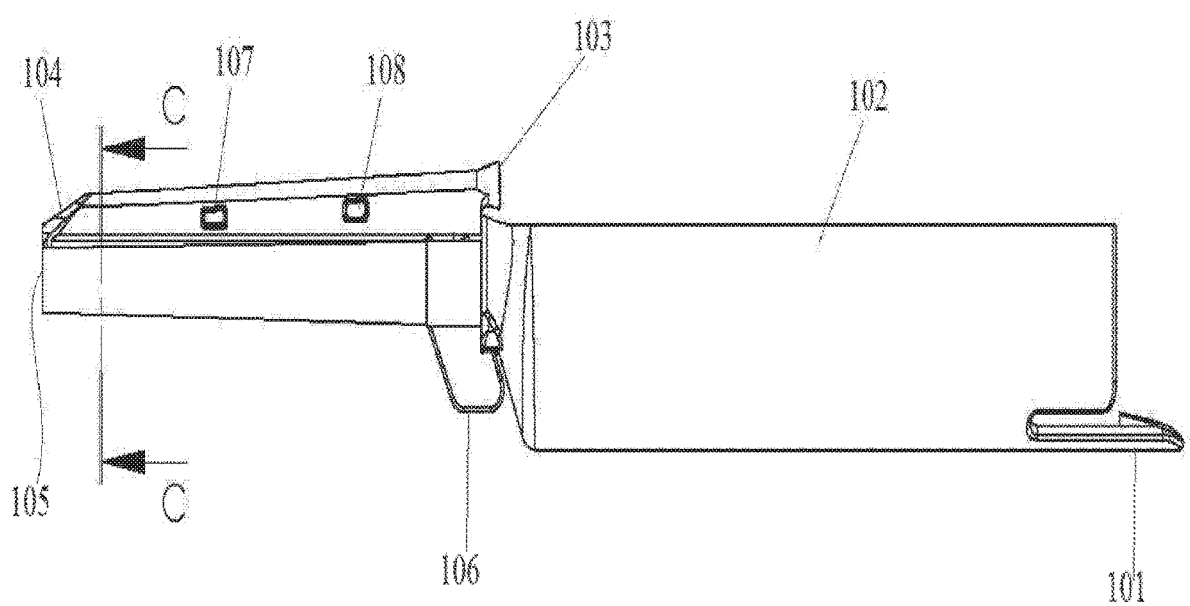

These and other echogenic shapes of needles, sheaths and tools for imaging in parallel via a parallel ultrasound transducer are described in U.S. provisional patent application Ser. No. 62/526,170 filed Jun. 28, 2017, incorporated by reference as to its entire contents. Imaging may also be improved using a known contrast agent during a procedure if the needle, syringe, sheath or tool penetrates the skin tissue so that blood vessels may preserved from puncture as a tool is guided toward a region of interest.

Thus, there will be described in the following detailed description a plurality of embodiments and features of an image guided catheter or probe of the present invention with removable, replaceable and reusable imaging assemblies and removable, replaceable instruments for performing minimally invasive medical procedures as will be explained further herein.

DETAILED DESCRIPTION

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

Minimally invasive procedures provide physicians with access to internal organs and structures via a small number of incisions in the patient's body. Minimally invasive procedures are generally preferable over open procedures because they require only small incisions, thus reducing trauma to the body, lessening recovery time, and reducing costs. The medical instruments used in performing such procedures are generally similar to those used in open surgical procedures except that they include an extension such as a tubular extension of small outer diameter between the patient end of the instrument entering the surgical field (i.e., the operable end of the tool, instrument or device) and the proximal end portion having a large outer diameter gripped by the surgeon, the tubular extension at the distal or patient end being tapered or having a viewing dome and containing an imaging assembly lumen and at least one other lumen, for example, for an introducer needle having a solid pointed tip, a biopsy or other needle, sheath, syringe or other tool or instrument of various types once the operating site is reached.

Typically, minimally invasive procedures may involve up to five incisions up to one inch in length. The treatment area is then accessed by inserting one or more cannulas or sleeves through the incisions to provide entry ports through which instruments are passed. Alternatively, access to the treatment area can sometimes be obtained using a natural body opening such as the throat, nose, ear canal or rectum or via a vein. In procedures using this approach, a cannula or sleeve may be inserted into the bodily opening and surgical instruments are passed to the treatment site, either through the cannula/sleeve or directly through the body opening or vein.

While minimally invasive procedures provide numerous advantages over open procedures, they generally do not provide a physician with a direct view of the targeted sites. Further, many parts of the anatomy are rather complex and/or small and thus require particular precision and delicate handling. It is therefore desirable to provide precise imaging techniques for use during minimally invasive procedures.

In general, the illustrated embodiments and aspects provide an image guided catheter/probe device that couples an imaging system within an imaging lumen and an instrument delivery system and/or minimally invasive interventional device within a further lumen or channel (such as the needle channel 103 of FIG. 1) open from the proximal end to the tapered or flat distal end. The instrument delivery system can include, for example, delivery of materials to or from a target site or delivery of instruments and devices to a target site, depending on the application.

In accordance with aspects described herein, an ultrasound imaging device of this invention can comprise one or more small ultrasound transducers integrated into an imaging transducer assembly exemplified by a linear phased transducer array, either as forward-directed transducers for direct, head-on imaging or combined with one or more side-directed transducers (as taught in priority patent applications and issued patents of inventor Dr. Abraham) which can provide additional imaging or other ultrasound applications such as delivery of heat to a target site within the patient. In addition, such ultrasound imaging can also be combined with all-optical high-resolution transducer imaging such as optical coherence tomography imaging and/or provide optional optical imaging through the use of one or more fiber optic bundles disposed though the imaging transducer probe and cable assembly in additional imaging lumens (not shown) but discussed in priority applications and patents.

For example, a first low resolution, long range ultrasound imaging transducer assembly may be used with an introducer needle to subcutaneously enter a patient. This assembly may be replaced with a higher resolution, short range imaging transducer assembly as the target site is reached in real time. Once the site is reached, a further high resolution, short range assembly may be introduced through the imaging lumen or channel which may comprise an optical coherence tomography device which operates on an echo principle similar to that employed by ultrasound. One or more minimally invasive medical procedure applications will be discussed herein.

An imaging system in accordance with aspects and features described herein can guide and facilitate many different procedures, thereby significantly assisting in the access of and performance of procedures on organs, structures and cavities within the body, particularly during minimally invasive procedures. The described devices and methods are compatible with all surgical and diagnostic devices and will allow bedside emergency procedures. Ultrasound provides particular benefits because it is biologically safe and uses non-radiating energy to provide detailed anatomic and, in some cases, functional images. The images generated by devices described herein can provide a user with direct vision within the body in real time. Further, both ultrasound and optical coherence tomography provide a user with visualization of structures as well as within and beyond nearby structures (such as the pericardium) to perform procedures such as a cardiocentesis.

In certain embodiments, the device may comprise an ultrasound imaging catheter/probe that incorporates one or more variable frequency ultrasound transducer assemblies that replace an original transducer assembly operating at one or more frequency ranges within the frequency range of from twenty kilohertz to, for example, several hundred megahertz; (however, the wavelength of such a low frequency may require the probe housing to have a large diameter unsuitable for subcutaneous probe insertion). Optical coherence tomography may provide further imaging at radio frequencies, for example, in the infrared. In one preferred embodiment, one selected frequency range of one replaceable transducer assembly of a center frequency may be from ten to forty megahertz (fifteen megahertz center frequency shown). However, various frequency ranges of the replaceable ultrasound transducer assembly can be used for different purposes and provide different beneficial results. Frequencies in the lower range, for example, below one megahertz, and particularly in the 100 to 200 kilohertz range, can be used, for example, to provide heat therapy or to treat conditions such as blood clots and provide low resolution, long range imaging. Frequencies above one megahertz can be used to provide higher resolution, short range imaging. For example, frequencies in the 25 to 30 megahertz, range can be used to image organs such as the eye or can be used to provide imaging of small animals. Even higher frequency ranges, for example, ultrasound frequency ranges in the one hundred to several hundred megahertz frequency range, can be used to provide very high-resolution imaging, sometimes known as high-frequency ultrasound microscopy. This and optical coherence tomography may achieve sub-micrometer resolution for use in very close target sites such as at a heart valve with minimally invasive surgery replacing prior art open heart surgery. A further operation for placing, for example, for placing a heart pacemaker may now employ the present invention to place the pacemaker directly on the pericardium rather than utilize a wire and hook device to deliver an electric pulse to the heart as is now commonly used. Now the image catheter devices will be further discussed with respect to potential applications.

Devices and methods such as are described herein are suitable for use in a variety of medical procedures. In certain embodiments, the image guided catheter device may comprise conventional catheter applications including, for example, biopsy catheters, ablation catheters, and mapping catheters, in combination with the novel imaging aspects of replaceable imaging frequencies and instruments imaged by the imaging components described herein. In other embodiments, the device can comprise one or more interventional devices (e.g. syringe, forceps, biopsy instruments, clamps, MEMS manipulators, retractors, etc.) that may be compatible with an imaging catheter/probe such as a biopsy catheter, ablation catheter, mapping catheter, or other form of sheath having larger diameter lumens. In some embodiments, the device can also be compatible with instruments such as video-scopes, external wired or wireless ultrasound imaging and delivery needles such as those used for stem cell therapy or implanted ultrasound devices which may utilize wireless transmission of ultrasound data for supplemental viewing of a surgical site. In still other embodiments, the devices may be compatible with fiber optics such as those used for vision therapy as well as optical coherence tomography. U.S. patent application Ser. No. 11/871,219 filed Oct. 12, 2007 (now U.S. Pat. No. 8,147,413 issued Apr. 12, 2012, Ser. No. 12/182,247 filed Jul. 30, 2008 (now U.S. Pat. No. 8,038,622 issued Oct. 18, 2011), Ser. No. 12/283,779 filed Oct. 14, 2008 (now U.S. Pat. No. 8,147,414 issued Apr. 3, 2012), Ser. No. 12/700,066 filed Feb. 4, 2010 (now U.S. Pat. No. 8,235,903 issued Aug. 7, 2012), Ser. No. 13/847,902 filed Aug. 22, 2013 (now U.S. Pat. No. 9,149,257 issued Oct. 6, 2016) and Ser. No. 13/973,476 filed Aug. 22, 2013 (pending) all by Theodore P. Abraham are incorporated by reference as to their entire contents, and all medical devices and applications described therein may be adapted for use with the present invention and, for example, adapted to fit through the needle/instrument lumen or channel or other additional lumen (not shown) of the present invention's expendable housing part (for example, per FIG. 1A). Furthermore, all other features and functionalities described in all these patent applications may be incorporated into and may be combined with embodiments of the present invention.

The devices and methods of various embodiments of an imaging catheter such as those illustrated in FIGS. 1A-17B and described herein can be used in various minimally invasive surgical procedures and in other diagnostic and therapeutic applications. One skilled in the art will appreciate that the aspects and embodiments of an imaging catheter/probe as described herein, although advantageously suited for such procedures on humans, can have other uses, such as for veterinary procedures and open medical techniques as well as minimally invasive procedures in humans or used externally or in body orifices. Further, while the devices of the present invention are described with particular reference to catheters/probes, this shall not be construed as limiting the devices to these embodiments, as it is contemplated and thus within the scope of the illustrated devices to adapt the devices described herein so as to be in the form of any type of minimally invasive or non-invasive device and sized for use for a medical procedure involving any body organ or structure (e.g. using syringes, sheaths, wires, forceps, biopsy instruments, clamps, retractors, micro-electronic motors (MEMS), etc.).

Further, while certain devices, systems and methods are described herein with particular reference to pericardial access devices, systems, and methods, this shall not be construed as limiting, as it is contemplated to adapt the devices, systems and methods described herein so as to be used in any of a number of procedures, including, but not limited to: various cardiovascular procedures; general micro-surgery; biopsy, drug and device delivery; vascular procedures; urology; thoracic procedures; otorhinolaryngology (ear, nose and throat); orthopedic procedures: neurosurgery; gynecologic procedures; gastroenterologic and general procedures; colon and rectal procedures; pericardiocentesis; thoracentesis; ascites tap; ventricular lead placements; and electrical and electro-mechanical mapping of the heart. As such, it is contemplated that the specific design parameters. (such as length of the distal end having parallel imaging and needle/instrument channels) and other characteristics set forth hereinafter, and methods in relation thereto can be modified to provide appropriate dimensions and geometries as required to perform such other techniques. For example, the length and diameter of the device as herein described is adapted to suit the particular conditions for a given procedure. Thus, the disclosure to follow should be considered illustrative only and should not be construed as limiting in any configuration of a device as described herein.

The device may be used to provide a three-dimensional mapping system solely using an incorporated ultrasound system or in connection with other imaging modalities such as optical coherence tomography, computed tomography, magnetic resonance, or videoscopy. When the device is in the form of a catheter, probe or sheath, this will allow stereotactic and remote/robotic operation of devices inserted and manipulated through the device. In such a system, an imaging modality (ultrasound, OCT, CT or MRI) can be used to generate a three-dimensional image on one of a plurality of two-dimensional screens. The device can interactively use the generated images to be directed either manually or through an automated or semi-automated process for deployment to a target area displayed in composite three-dimensional images from various views. The device can be used in connection with an ultrasound or OCT display system (B mode image or 3D image) that interfaces with the device to produce and display the images.

Figure 10A:
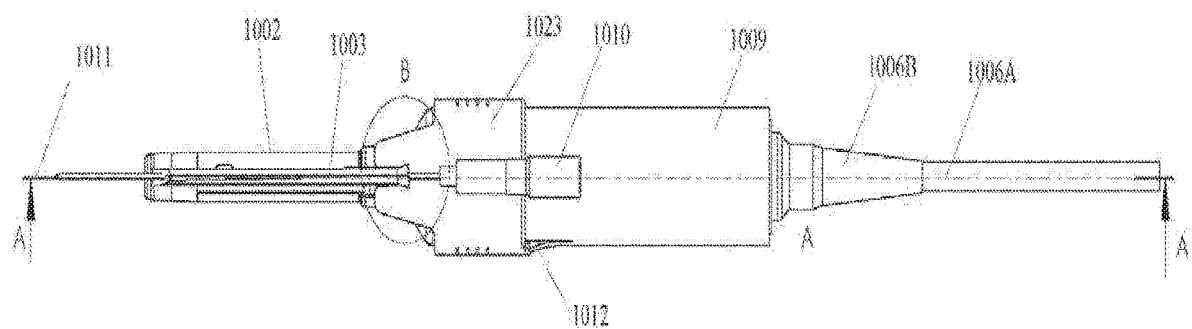
FIGS. 10A through 10I depict several views of the above-described needle guide embodiment and probe and cable assembly also including an exemplary needle having a handle 1010 and a tip 1011. The needle 1011 and handle 1010 are shown in the needle channel 1003. The needle 1010, 1011 may be a biopsy needle and be hollow for collecting tissue at a site of interest located by forward-imaging of a transducer array located behind sensor tip 1005. Retainer tab 1012 retained sleeve lock 1023 in a closed position.

By way of introduction, a fully assembled imaging device 1000 of the present invention is depicted in FIG. 10A-10I, (needle or syringe handle 1010 and needle 1011 first shown in FIG. 10A). The present invention includes new embodiments of the imaging catheter of U.S. Ser. Nos. 14/865,151 filed Mar. 24, 2015 (now allowed) and U.S. Ser. No. 13/847,902 filed Mar. 20, 2013 (now U.S. Pat. No. 9,149,257) with several new features and alternative embodiments in its design. In the present invention, the transducer element may be placed close to but separate from the introducer needle (or a syringe) so that either the one or the other may be removed and replaced at any time with another element/instrument according to the needs of the surgeon. The imaging assembly lumen or channel contained within probe section 1002 (FIG. 10B) and the needle/instrument lumen or channel 1003 located above an ultrasonic probe housing 1002 are placed in the center and top of the distal end of the device respectively. The ability to change imaging assemblies at will in real time during a procedure enables higher fidelity imaging as the operating site within a body is approached during a procedure by a needle, syringe tool or sheath within, for example, needle channel 1003. In one embodiment of the present invention as shown in FIG. 1A, the image quality may be improved by placing a vertical window 105 at the end of the imaging lumen or channel instead of an angled (or tapered) window or a dome which may be used in the alternative and may expand the imaging zone to hemispheric proportions. Another important new feature is a reusable imaging transducer comprising a linear phased array (FIG. 14A) contained in a separate imaging transducer assembly probe section insertable into a probe housing and top-mounted needle guide (for example, FIG. 1A or FIG. 8A or 8B that opens from the top, each transducer assembly operating at a desired ultrasound or optical coherence frequency range. The image guided catheter/probe device of the present invention comprises an expendable housing 102, 202, 502, 809, 909, 1009, 1109 with a proximal cable end 1006A proximal to the healthcare professional using the device, a distal tip 104, 204, 904, 1004 having an introducer needle, syringe or tool 1010, 1011 for insertion of the device into a patient's body or just the needle/syringe which is replaceable with other instruments, an imaging lumen or needle channel 103 that may open to release the needle/tool/instrument. In other words, the present device may be used subcutaneously, in a body orifice or external with just a needle puncture to introduce, for example, a biopsy needle or syringe.

In the image guided catheter/probe device (for example, FIG. 10A of the present invention), the distal housing, syringe and needle guide may be disposable and the imaging transducer assembly (more expensive) replaceably introduced through an imaging lumen channel in sheath 1009 and probe housing 1002 and may be removed and reused, separated from the device and cleaned if necessary. To reuse an imaging transducer assembly, for example, the front-end assembly seen in FIG. 14A, may be covered by window (for example, distal tip window 105 of FIG. 1A being disposable, removable and plastic or uncovered but protected within the distal probe housing while in use and sterilized between uses. The present invention is designed such that the imaging transducer assembly may have a curved cable shape that fits into a lengthwise slot on, for example, the left (or right) side, top or bottom, of the housing barrel, allowing the transducer assembly to slide into the imaging channel or probe housing 1460. The present invention may also include locking mechanisms or tabs (such as locking tab 101) to temporarily secure the imaging transducer assembly. The syringe/needle assembly has a needle channel that is opened either via a tab 106 (FIG. 1A) or via a sleeve lock 823 (FIG. 8A) to the proximal cable end 1306A of the reusable housing 1006A, 1006B, 1006C (FIG. 10C) which may reside in disposable sheath 1009.

The reusable imaging ultrasound transducer assembly section 1006A, 1006B, 1006C assembly may also be freely removed and replaced at any time during a procedure. For example, a lower-frequency transducer assembly 1462 adapted to produce images at a lower resolution but greater depth into the body may be used to find a target site in a patient's internal target organ. Once the target site is found, the user can remove a lower-frequency range transducer assembly and replace it with a higher-frequency range transducer assembly 1462 such as an OCT assembly to produce a higher-resolution image at the target site (with three dimensions) allowing the user to obtain an improved quality image or sequential series of images while performing a procedure.

The expendable housing, for example, housing 102, 809, 909, 1009 may be a variable outer diameter rigid plastic sheath with a diameter in the range of 1-20 French, with current preferred embodiments in the 10 to 14 French range (3.3667 to 4.6667 mm diameter) for tight work or much larger diameter such as 20 millimeters for larger work or to carry more imaging capability. The imaging channel 1465 (FIG. 14B) may have a larger outer diameter than that of the syringe/needle channel, for example channel or guide 103 or 903. The probe barrel which may enter a patient subcutaneously may be any length depending on the approximate distance of travel from a skin insertion to a target site. The imaging ultrasound transducer assembly 1362 (FIG. 13) may comprise a forward viewing phased array probe with a variable field of view depending on the specific array. The imaging transducer assembly 1362 may comprise an ultrasound or OCT transducer at the distal end (as seen in FIG. 14B) with variable frequency, variable cross-sectional diameter, and a variable number of transducer elements or optical fibers located in a steel or rigid plastic cylinder inside the expendable housing for the reusable housing with a variable outer diameter at the proximal end and narrow diameter at the distal end. Examples of possible arrangements of transducer elements at the tip of the transducer are depicted in U.S. application Ser. No. 13/847,902, FIGS. 5A 5B, and 5C. The present invention encompasses transducer assemblies 704 with center frequency ranges in the ten to forty megahertz range (fifteen megahertz center frequency shown), with a current preferred range of ten to twenty-five megahertz for use in traveling from external skin tissue (or the exterior of the eye) to one to five centimeters beneath the skin. Wide band OCT imaging may be performed as white light imaging as well as a narrower band near infrared imaging. However, the frequency ranges may vary depending on the particular application for which the imaging device is used.

The length dimensions of the probe barrel of the device are not particularly limited and can vary depending on the ultimate use of the device, the insertion point, the obesity of the patient and the distance to the target area from the insertion point (if insertion is required). The length of the device may vary depending on the application, but a preferred range is between one to four inches to be used, for example, for vascular applications, ranging up to twenty inches (ten inches for the proximal or surgeon end and ten inches for the distal end) to be used, for example, to perform procedures on the liver. The diameter and length of the tapered, flat or domed end near, for example, the distal tip 105 of the housing 102 can be affected by the size of an anatomical structure in which it is to be inserted. For example, the tapered, flat or domed distal end 105 can be of greater radius, longer or more slender for deep abdominal structures such as the kidneys or pelvic structures such as the ovaries or uterus, or can be shorter and wider for delivery of devices into more shallow structures such as a joint, muscle, the liver, or the heart. The diameter of the distal end can also be affected by the desired size of the incision through which device 1000 is inserted and which must subsequently be closed. The diameter of the distal end 105 of the probe housing can also be affected by the purpose for which the device is used. For example, the diameter of the distal end can be smaller for aspiration of fluids from a target site or larger if additional ports or device/medication delivery are desired.

For example, when device 1000 is in the form of a vascular sheath (not shown), the outer diameter can vary depending on the targeted blood vessel through which the distal tip 105 is inserted. In an embodiment, device 1000 can be in the form of vascular sheaths (not shown but exemplified in priority applications and patents) used during cardiac procedures and can be inserted through a blood vessel in the upper thigh or, alternatively, can be inserted through a blood vessel in the arm. In another embodiment, alternative devices 1000 can be inserted by anesthetizing an area of the patient's upper thigh and inserting the distal end 105 (if of sufficiently narrow diameter) through a blood vessel in the upper thigh and towards the heart. In this embodiment, the distal end 105 can have a length sufficient to traverse this pathway, a diameter small enough and material flexible enough to be inserted into a blood vessel and advanced through the blood vessel to a target site. In an additional embodiment, the front end of the imaging transducer assembly 1362 may be housed in a flexible material that would allow the front end of the ultrasound transducer to advance longer distances through a blood vessel along with a flexible distal end of the image guided catheter device 1000. In a further embodiment, device 1000 can have an introducer needle 1011 integrated (not shown) therein (without using a syringe), which can enable device 700 to penetrate directly into the chest wall of a patient for direct access to the heart without the need for access through the vascular system. A cardiocentesis may be performed in this way using an introducer needle 1011 followed by a syringe 1011 once the heart is reached and the introducer needle replaced with the syringe to alleviate some excess body fluid in the pericardial space.

Device 1000 can also be in the form of a sheath (not shown) used, for example, during a laparoscopic procedure, and in such a case, the distal (patient) end 105 can generally have an outer diameter in accordance with conventional laparoscopic sheaths and will have a length that provides access to the target site.

Further, the device can be used as a minimally invasive conduit from the skin surface to the target site to allow passages of catheters, guide wires (not used in the depicted embodiment 1000), and other instruments through distal tip 104 of the depicted needle guide, and the distal tip 104 can be sized to allow these various instruments to be passed therethrough. The user of the device may change the imaging transducer assembly 1462-1 through 1462-23 as needed during a procedure to obtain a better image, and the user may also change the instrument contained in the needle channel 103, 1003 as needed to perform the procedure.

In an exemplary embodiment described in more detail herein, device 1000 can be in the form of an image guided catheter 1000 that can be introduced through the chest, side or back to access various internal structures using minimally invasive techniques. As such, the distal end 104, 105 can have an outer diameter ranging from about 1 F to 15 F (wherein 1 F=0.33 mm) up to about six millimeters and a length ranging from about 1" to 20". Specific lengths and diameters can be provided based on the insertion site of the catheter/probe, the distance to the desired target site(s), the obesity of the patient and the space required for insertion of one or more interventional devices through the distal (patient end) tip 104.

In other embodiments, device 1000 can be in the form of any interventional device that can be, for example, inserted through a sheath (not shown) or catheter to access various internal structures using minimally invasive techniques. As such, the distal tip 104, 105 can have an outer diameter sized so as to fit within conventional sheaths or catheters, and a length suitable to access the desired target site(s) through the sheaths or catheters.

FIG. 1A depicts a view of a patient or distal end of an image guided catheter device assembly which may be referred to herein as a barrel (as distinct from a larger diameter proximal end, not shown) in accordance with one or more aspects described herein, FIG. 1A showing a replaceable introducer needle/syringe/instrument channel/lumen having a distal tip 104 visible in an imaging zone of a replaceable transducer element 1362 (FIG. 13) replaceable as higher resolution is needed when the access instrument reaches the operating site if used subcutaneously. As shown in FIG. 1A, the ultrasound or OCT transducer or other known vision element being the distal tip 105 of the device 1000 at the patient end has an imaging zone desirably encompassing the tip of the introducer needle 1011 (typically pointed) or biopsy needle or syringe (typically hollow) as it emerges from guide or channel 103. FIG. 1A shows an introducer needle lumen or channel 103 of a needle guide mounted above an ultrasound or OCT imaging lumen or channel ending at tip 105 that is captured by a imaging plane of an ultrasound transducer array; (see FIGS. 9E, 9I). The removable, replaceable imaging transducer assembly 1362 (not shown) may be inserted into the imaging probe barrel as will be discussed herein in real time during a medical procedure. To reduce ultrasound deflection during use of the device, as seen in FIG. 1A, the imaging system can be provided with matching layers disposed, for example, adjacent the front face of transducer elements. Matching layers can facilitate the matching of an impedance differential that may exist between the high impedance transducer elements and a low impedance patient. The structure of matching layers can generally be in accordance with conventional matching layers and generally can include a matching layer front face and a matching layer rear face, and can optionally include a pocket with matching material that can reduce ultrasound deflection. Suitable matching layer materials can include, for example, plastic materials such as polysulfone or REXOLITE® (a thermoset material produced by cross-linking polystyrene with divinyl benzene, available from C-LEC Plastics, Inc., Beverly, N.J.).

The imaging system may further include a backing layer (not shown) in accordance with conventional backing layers. The backing layers can generally be coupled to the rear face of the transducers 1462-1 through 1462-23 (FIGS. 14A and 14B) and function to attenuate acoustic energy that emerges from the rear face of the transducer elements. Generally, such backing layers can have a front face and a rear face, and can be fabricated of acoustic damping material that possesses high acoustic losses.

Transducers can be of a size and composition in accordance with conventional transducers. For example, in some embodiments, the transducer elements can comprise natural piezoelectric materials such as quartz, topaz, or tourmaline group minerals or can comprise man-made materials such as PZT ceramics or piezoelectric polymers such as Polyvinylidene fluoride (PVDF). In other embodiments and for high resolution and all-optic ultrasound transducer is useful. Transducer elements can also be of any suitable size, with such size being limited by the desired size of the housings used and the use which is being made of the ultrasound, i.e., for imaging or therapeutic purposes.

In currently preferred embodiments, as many as 20-96 channels (twenty-three by way of example) may be provided from the ultrasound transducer array to the display output device through the ultrasound transducer and cable assembly. However, further embodiments of the transducer assembly may contain anywhere from one to 2000 ultrasound imaging channels, with a greater number of parallel channels possible as ultrasound imaging technology progresses toward smaller elements such as, for example, fiber optics. Moreover, known contrast agents may be introduced through a hollow needle or sheath lumen through a blood vessel and may be known to adhere to, for example, human muscle tissue or a heart valve or other organ of interest to improve echogenicity just as the needle, sheath or a tool may have an echogenic surface such as a spirally wrapped wire round the needle or syringe.

Figure 1B:
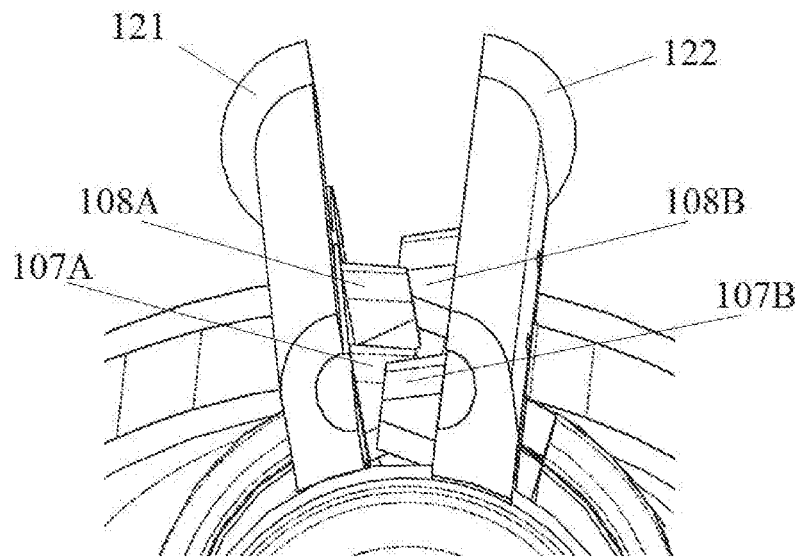
FIG. 1B depicts a top view of a needle guide 103 of FIG. 1A to show how guides 121 and 122 guide a needle or tool into a needle channel and can rest on needle buttons 107A and 108A of one side of the needle guide 103 and also rest on needle buttons 108A and 108B of the other side of the needle guide.

FIG. 1B depicts a top view of a needle guide 103 of FIG. 1A to show how guides 121 and 122 guide a needle or tool into a needle channel and can rest on needle buttons 107A and 108A of one side of the needle guide 103 and also rest on needle buttons 108A and 108B of the other side of the needle guide. FIG. 1A disposable housing and needle guide is operated by tab 106 to rotate one half of a needle guide to match with the other half.

Figure 1C:
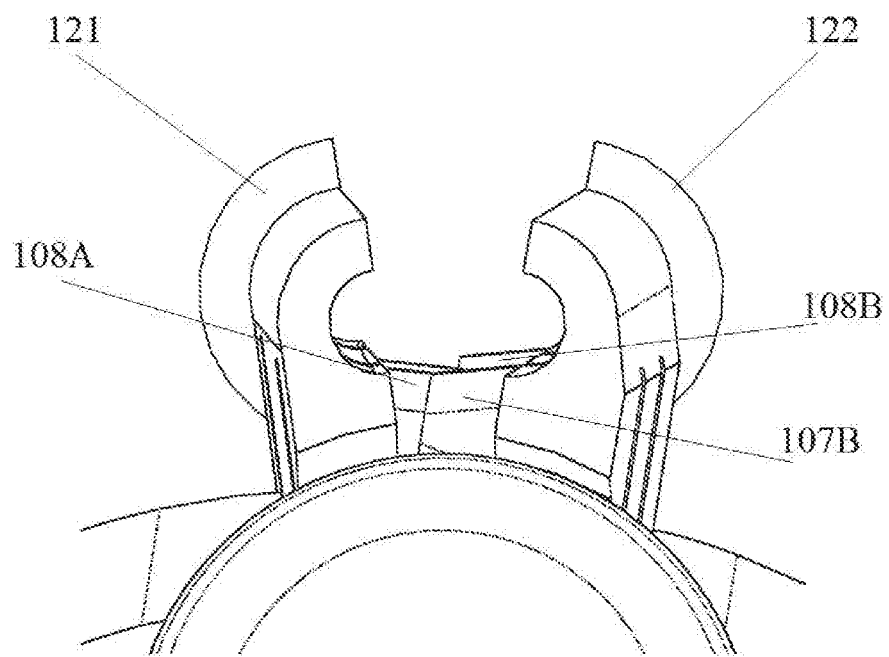
FIG. 1C depicts an open front view of the needle guide 103. A needle (syringe or tool) may be moved out of the guide sides shown due to opening guides 121 and 122. Button tabs 107A and 107B along with button tabs 108A and 108B help extricate the needle from the needle guide 103 from above.

FIG. 1C depicts an open front view of the needle guide 103. A needle (syringe or tool) may be moved out of the needle guide 103 due to opening guides 121 and 122. Button tabs 107A and 107B along with button tabs 108A and 108B help extricate the needle from the needle guide 103 from above. Such an open needle guide precludes the collection of material which may adhere to a needle or syringe or other bodily material at the needle guide end 104 when the needle is removed through a closed needle guide.

Figure 2A:
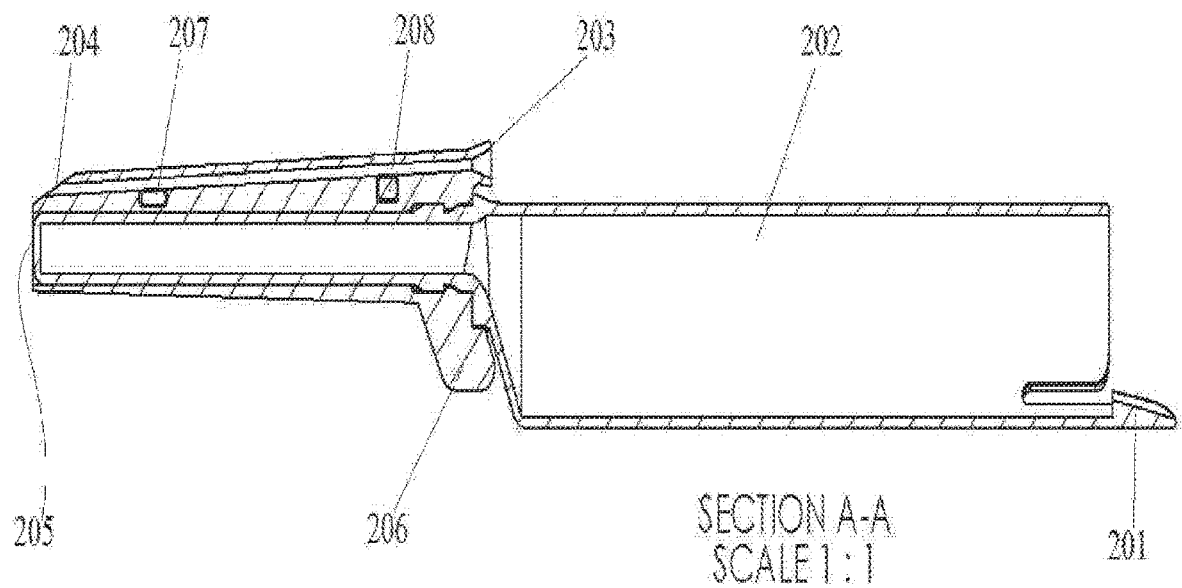
FIGS. 2A and 2B depict different cross-sectional views of the patient or distal end of the embodiment of FIG. 1 where tab 106 for closing the needle channel is now referenced as tab 206 for opening the needle channel 203 of an imaging device in accordance with one or more aspects described herein. When tab 206 is manipulated in a clockwise direction round the elongated housing's cylindrical body, the needle channel is closed around a needle/syringe/tool (not shown).
Figure 2B:
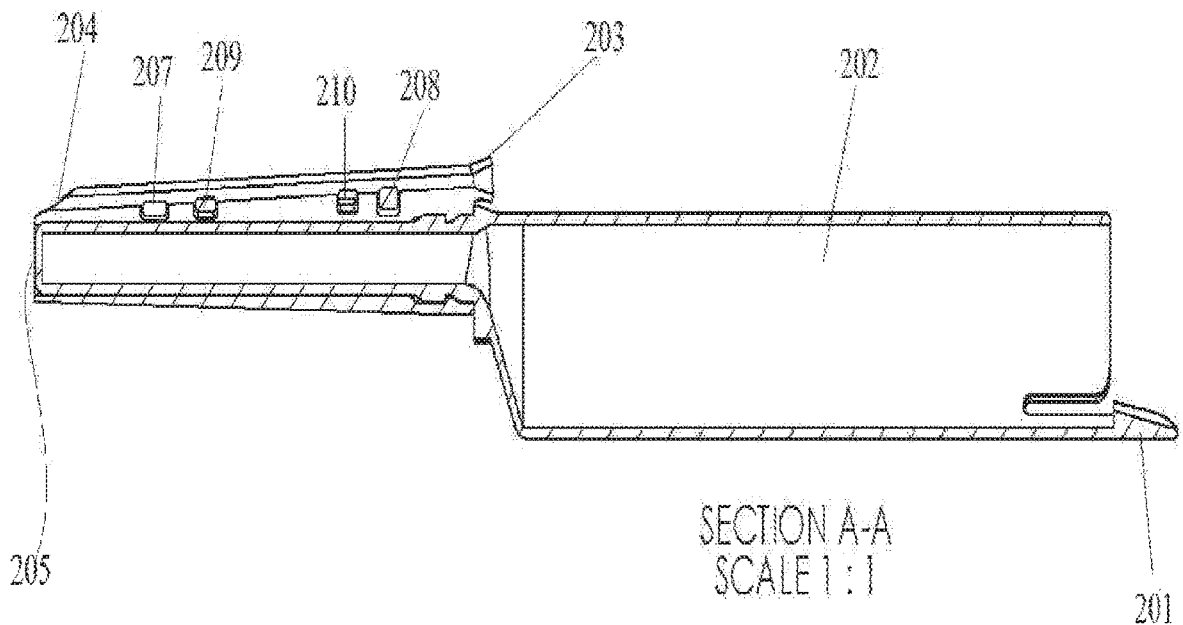

FIGS. 2A and 2B depict different cross-sectional views of the patient or distal end of the embodiment of FIG. 1A where tab 106 for closing the needle channel is now referenced as tab 206 for opening the needle channel 203 of an imaging device in accordance with one or more aspects described herein. When tab 206 is manipulated in a clockwise direction, the needle channel is closed around a needle/syringe/ tool not shown or opened to allow vertical removal. FIG. 2B shows additional button tabs 209, 210 which may be used or not used in a given embodiment to further serve to support a needle/syringe/tool in needle channel button tabs; (see FIGS. 1B and 1C). Needle channel tip 204 may be tapered and may receive and permit a tapered tip hollow needle (possibly of a syringe) to exit the needle guide at tip 204. Sensor channel tip 205 may indicate the location of an ultrasound sensor not seen which may be directed forward and provide forward-imaging of a needle/syringe/tool in the needle channel 203 as it extends into a forward imaging zone of a transducer array (such as array 1362 of FIG. 13). In either figure, a rear tab 101, 201 may lock a sensor and cable section assembly in place within the body 202 comprising a sensor channel (transducer assembly and cabling). Needle 1010 and sensor and cable assembly 1006 are first seen in FIG. 10 locked in place by tab 1001.

Figure 3A:
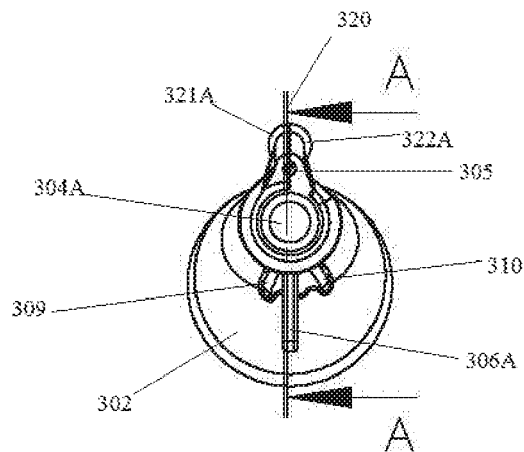
FIG. 3A provides an enlarged front-end view of the tab 106 now seen as tab 306A which may move between positions 309 and 310 to open or close the needle channel.

FIG. 3A provides an enlarged front-end view of the tab 106 now seen as tab 306A which may move between positions 309 and 310 to open or close the needle channel. In FIG. 3A, the needle channel tip 304A is shown closed.

Figure 3B:
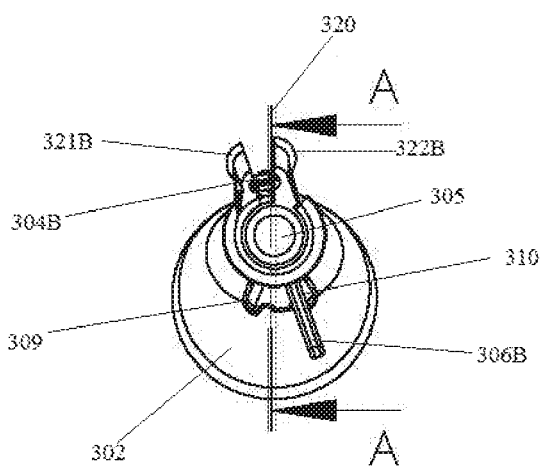
In FIG. 3B, the needle channel tip 304B is shown open. Similarly, a first part of the needle channel 321A is shown closed in FIG. 3A, and the same part of the needle channel 322B is shown open in FIG. 3B. Sensor channel 302 of either FIGS. 3A and 3B carries the sensor and cable to the sensor channel tip 305. A second part of the needle channel 322A or 322B remain stationary where line 320 represents the line along which the needle channel opens. Section A-A extends from the top of the needle channel through the sensor body 302.

In FIG. 3B, the needle channel tip 304B is shown open. Similarly, a first part of the needle channel 321A is shown closed in FIG. 3A and the same part of the needle channel 321B is shown open in FIG. 3B. Sensor channel 302 of either of FIGS. 3A and 3B carries the sensor and cable to the sensor channel tip 305. A second part of the needle channel 322A or 322B remain stationary where line 320 represents the line along which the needle channel opens. Section A-A extends from the top of the needle channel through the sensor body 302.

Figure 4A:
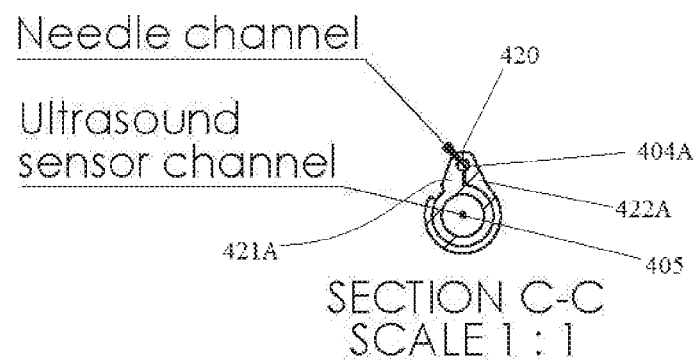
FIGS. 4A and 4B depict details of the opening and closing of a needle channel using tabs 106 where
Figure 4B:
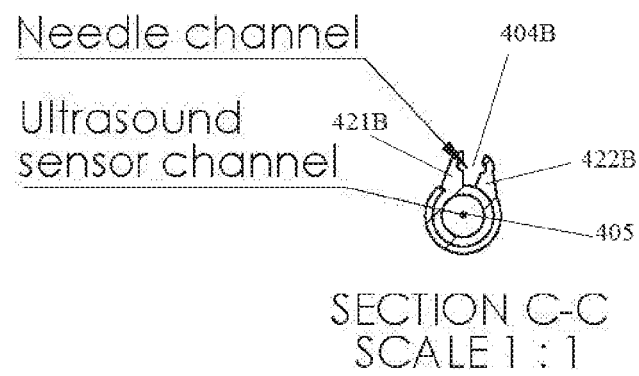

FIGS. 4A and 4B depict details of the opening and closing of a needle channel using circularly moveable tab 106 where FIG. 4A represents a closed needle channel and FIG. 4B represents an open needle channel, for example, where partial circular sections connected to tab 106 comprise line 420 along which the needle channel opens. FIG. 4A comprises closed needle channel tip 404A, the first part 421A of the closed needle channel, the second part 422A of the closed needle channel, and the sensor channel tip 405 of the ultrasound sensor channel. Referring to FIG. 4B, sensor channel tip 405 is in the center. Surrounding this center 405 are open needle channel tip 404B, open second part 422B of the needle channel and open first part 421B of the needle channel. Section C-C is taken just of the probe housing as seen in FIG. 1A.

Figure 5A:
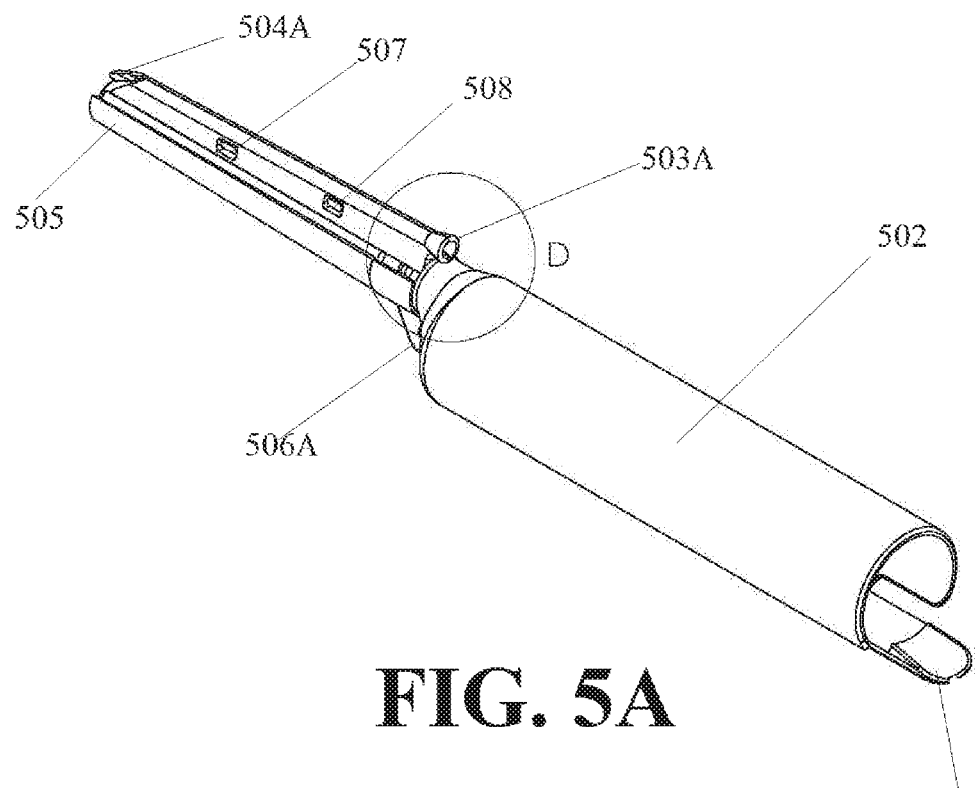
FIGS. 5A and 5B depict in rear perspective view a closed needle channel 504A (FIG. 5A), button tabs 507, 508, and closed needle entry 503A (FIG. 5A) leading to distal closed tip 504A (FIG. 5A) of the needle channel sensor channel tip 505 (seen in both FIGS. 5A and 5B). The sensor body 502 in both figures has a tab 501 for allowing a sensor probe and cable to be placed within the housing per FIG. 10. Closing tab 506A in FIG. 5A shows a close position for the needle guide while closing tab 506B in FIG. 5B shows an open position for the needle guide as per open needle guide 503B. Distal tip 504A is shown closed in FIG. 5A and open tip 504B is shown in FIG. 5B. Circle D shows the difference between closed needle guide 503A (FIG. 5A) and open needle guide 503B (FIG. 5B) where opening and closing uses tabs 506A (closed) and the same tab 506B in an open position.
Figure 5B:
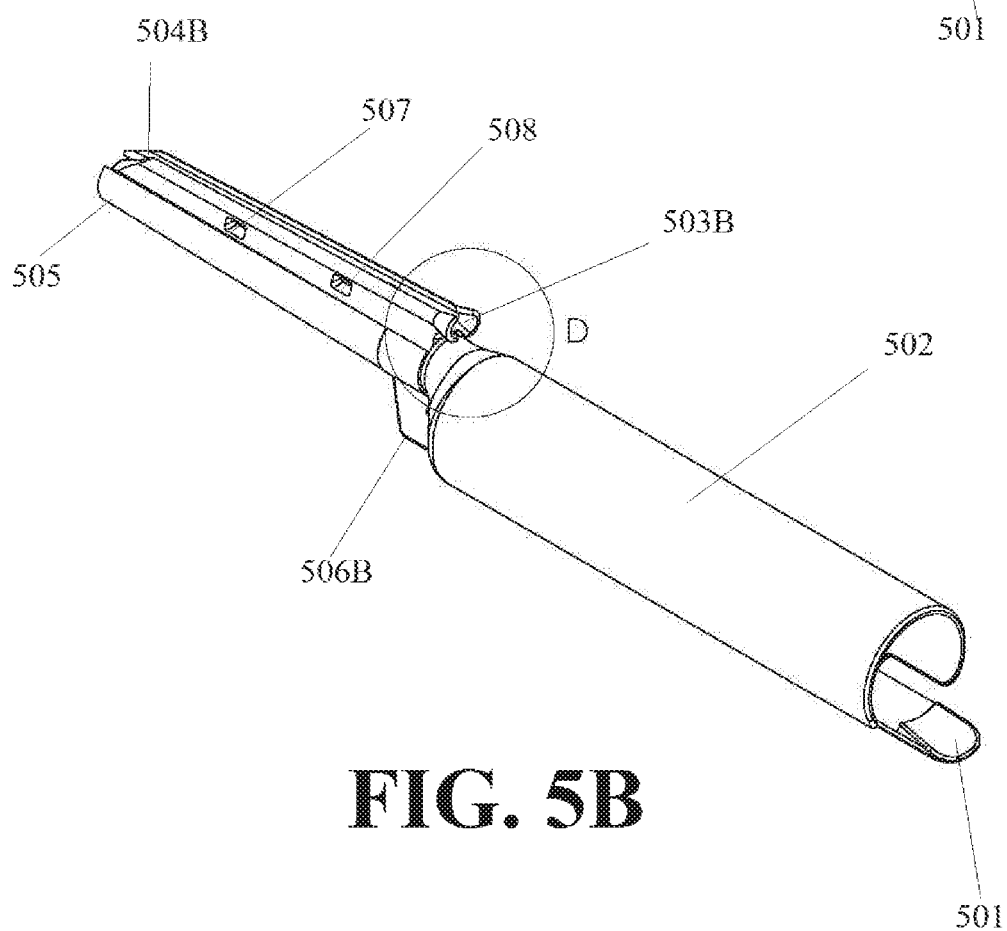

FIGS. 5A and 5B depict in rear perspective view a closed needle channel 504A (FIG. 5A), button tabs 507, 508, and closed needle entry 503A (FIG. 5A) leading to distal closed tip 504A (FIG. 5A) of the needle channel sensor channel tip 505 (seen in both FIGS. 5A and 5B). The sensor body 502 in both FIGS. 5A and 5B has a flexible locking tab 501 for allowing a sensor probe and cable assembly to be placed within the housing per FIG. 10. Closing tab 506A in FIG. 5A shows a close position for the needle guide while closing tab 506B in FIG. 5B shows an open position for the needle guide as per open needle guide 503B. Distal tip 504A is shown closed in FIG. 5A and open tip 504B is shown in FIG. 5B. Circle D shows the difference between closed needle guide 503A (FIG. 5A) and open needle guide 503B (FIG. 5B) where opening and closing uses tabs 506A (closed) and the same tab 506B in an open position.

FIGS. 6A through 12I show an embodiment similar to the previously discussed embodiment whereby a sleeve lock is used to lock two halves of a needle channel of a needle guide together around an inserted tool: needle, syringe or other tool. Normally, the needle guide is open but may be closed by a sleeve lock as discussed herein.

Figure 6A:
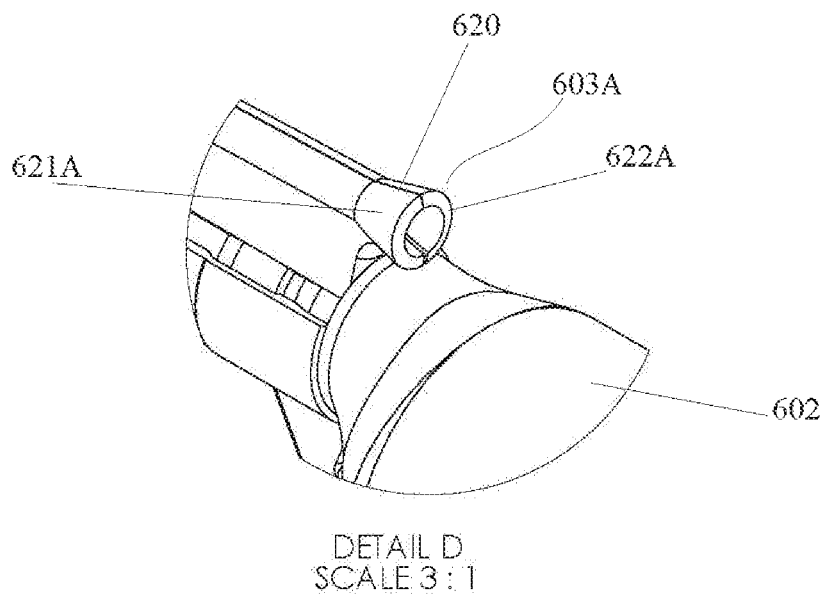
Figure 6B:
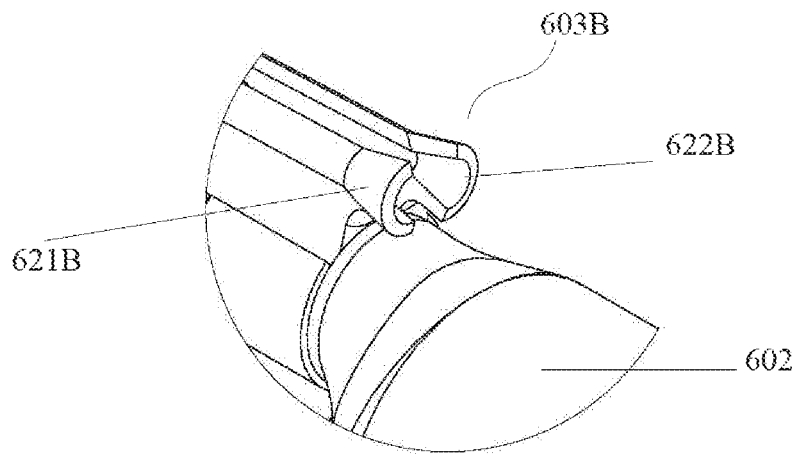

FIGS. 6A and 6B depict front perspective views of the line 620 along which the needle channel 603 opens along with a portion of the sensor housing or body 602. Referring to FIG. 6A, needle channel 603A is in a closed position, the first part of the needle channel 621A is closed as is the second part (for example, half) of the needle channel 622A. Referring now to FIG. 6B, the needle guide is in an open position 603B and the first and second parts 621B and 622B (for example, halves) of the needle channel are opened to their normally open position.

Thus far, we have discussed how a tab 106 may open and close a needle channel. In FIGS. 7A through 8H and in FIG. 9A an alternative to a tab closure is shown that comprises a sliding groove 724 moved by a surgeon via a circular or partially circular tab or sleeve lock 723 with unnumbered finger grips seen as rounded gripping ridges on the sides of the sleeve lock 723.

Figure 7A:
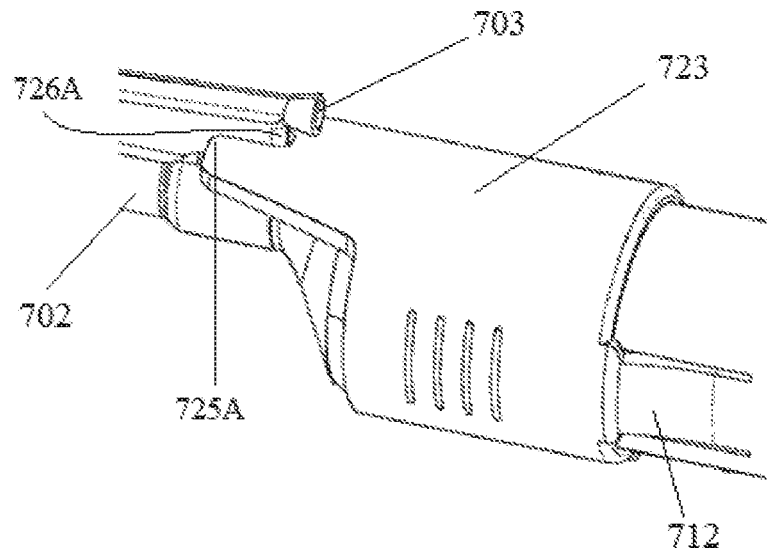

FIG. 7A shows sensor housing channel 702 and the needle channel 703 in a closed position where the circular tab or sleeve lock 723 and groove 725A have been slid forward to clasp the two halves of a needle guide 703 together. The groove may have parallel sides shown or have V-shaped clasping sides (not shown). The parallel sides 721 and 722 (FIG. 7B) of groove 724 may have a corresponding quarter-circular portion 725A which gathers the two sides 721, 722 of the needle guide together, and the groove 724 holds the needle guide together. A retaining spring tab 712 retains the sleeve lock so as to close the needle channel 703. Any circular arc 725A may mate with a similar arc to close the normally open needle channel 703 in groove 704. Another example is an approximately forty-five degree angle on each of the groove 724 as 725A and the halves of the needle guide 703.

Figure 7B:
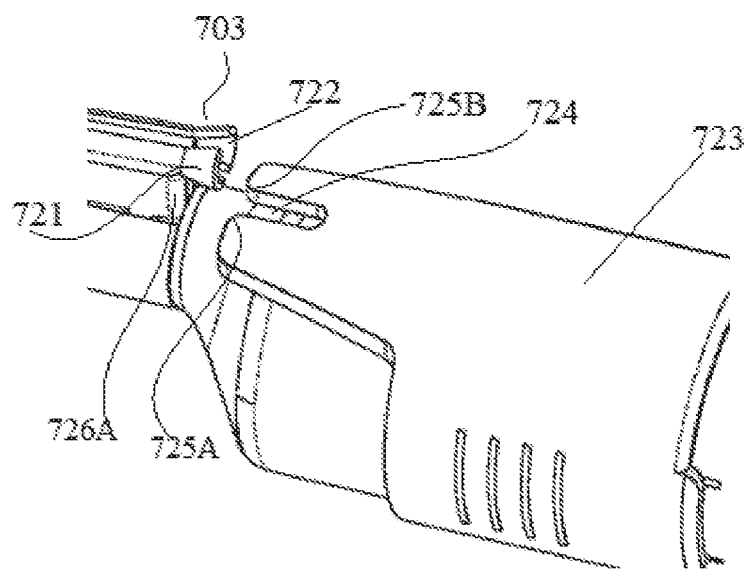
In FIG. 7B, it may be seen that a matching quarter-circular portion 725B matches portion 725A and so, when they meet as the tab 723 is closed, the two sides 721, 722 of the needle guide 703 are caused to collapse and be held by together by the groove 724 via sleeve lock 723 as seen in FIG. 7A.

In FIG. 7B, it may be seen that a matching quarter-circular portion 725B matches portion 725A and so, when they meet as the tab 723 is closed, the two sides 721, 722 of the needle guide 703 are caused to collapse and be held by together by the groove 724 via sleeve lock 723 as seen in FIG. 7A. As already discussed, a quarter circle is shown but may be another arc of a circle or a cut at, for example, a forty-five degree angle.

Figure 8A:
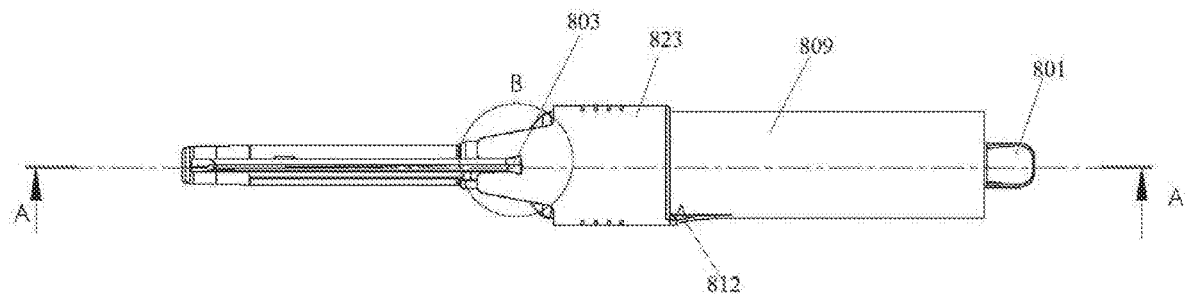
FIG. 8A depicts a top down view of the groove closure of FIGS. 7A and 7B. As already seen, sensor housing 809 has a locking tab 801 for linking with a sensor and cable assembly seen in FIG. 10. Needle guide 803 is seen held closed in a groove and is so held in a closed position as long as the groove grips the halves of the needle guide 803 together. Retaining tab 812 holds sleeve lock 823 closed also closing needle channel 803.

FIG. 8A depicts a top down view of the groove closure of FIGS. 7A and 7B. As already seen, sensor housing 809 has a locking tab 801 for linking with a sensor and cable assembly seen in FIG. 10. Needle guide 803 is seen held closed in a groove and is so held in a closed position as long as the groove grips the halves of the needle guide 803 together. Flexible retaining tab 812 holds sleeve lock 823 closed also closing needle channel 803.

Figure 8B:
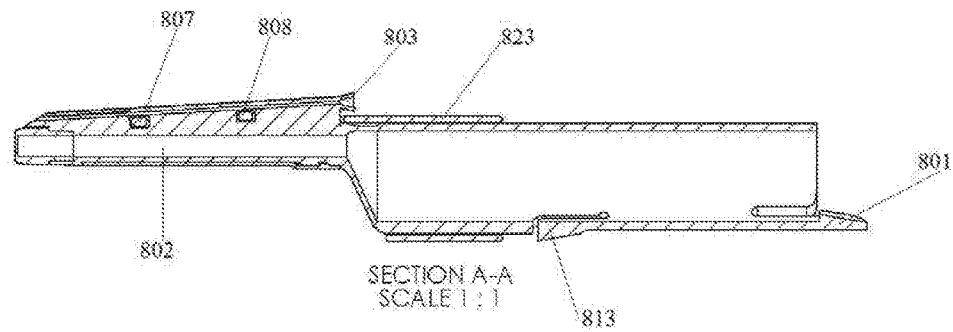
FIG. 8B provides a side cross-sectional view of the sensor and needle guide assembly shown in top view in FIG. 8A. Sensor 802 has a locking tab 801 for linking to an internal transducer and cable assembly per FIG. 10 as seen in FIG. 8A in top view. Needle guide 803 is shown closed with button tabs 807 and 808. Retaining tab 813 prevents a sleeve lock 823 from opening any further than its raised edge.

FIG. 8B provides a side cross-sectional view of the sensor and needle guide assembly shown in top view in FIG. 8A. Sensor 802 has a flexible locking tab 801 for linking to an internal transducer and cable assembly per FIG. 10 as seen in FIG. 8A in top view. Needle guide 803 is shown closed with button tabs 807 and 808 for supporting a needle, syringe or other tool. A flexible retaining tab 813 prevents a sleeve lock 823 from opening any further than its raised edge.

Figure 8C:
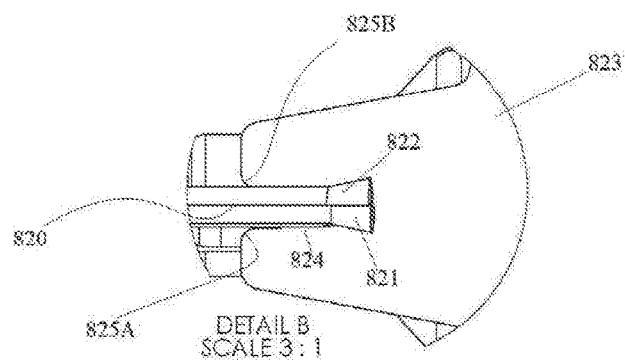
FIG. 8C depicts an expanded view of the closing groove mechanism (Detail B) for closing the needle guide first and second parts 821 and 822 along line 820 via quarter-circular groove portions 825A and 825B so that sleeve lock 823 in a forward position closes the needle guide within the depicted groove 824.

FIG. 8C depicts an expanded view of the closing groove mechanism (Detail B) for closing the needle guide first and second parts 821 and 822 along line 820 via quarter-circular groove portions 825A and 825B (or other circular arcs or forty-five degree cuts) so that sleeve lock 823 in a forward position closes the normally open needle guide halves within the depicted groove 824.

Figure 8D:
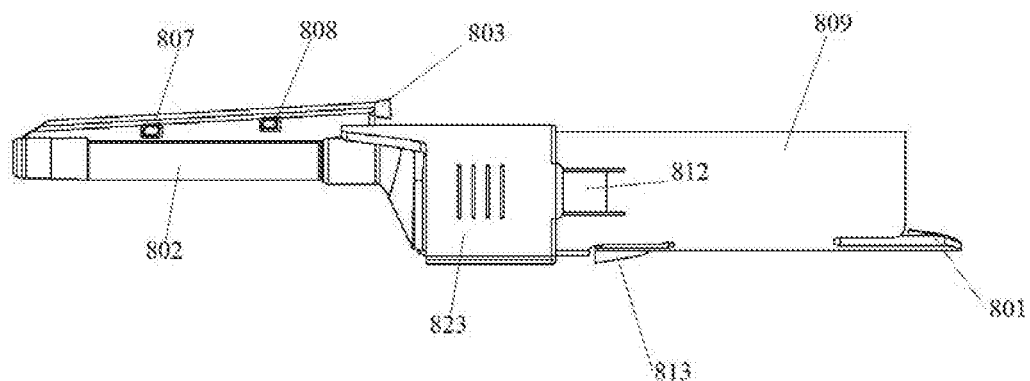
FIG. 8D shows a side view similar to the side cross-sectional view of FIG. 8B. The sensor channel 802 is seen at the distal end and the tab 801 at the proximal end. The finger grip 823 is shown extended so as to force the needle channel 803 closed with button tabs 807 and 808.

FIG. 8D shows a side view similar to the side cross-sectional view of FIG. 8B. The sensor channel 802 is seen at the distal end and the tab 801 at the proximal end. The finger grip 823 is shown extended so as to force the needle channel 803 closed with button tabs 807 and 808.

Figure 8E:
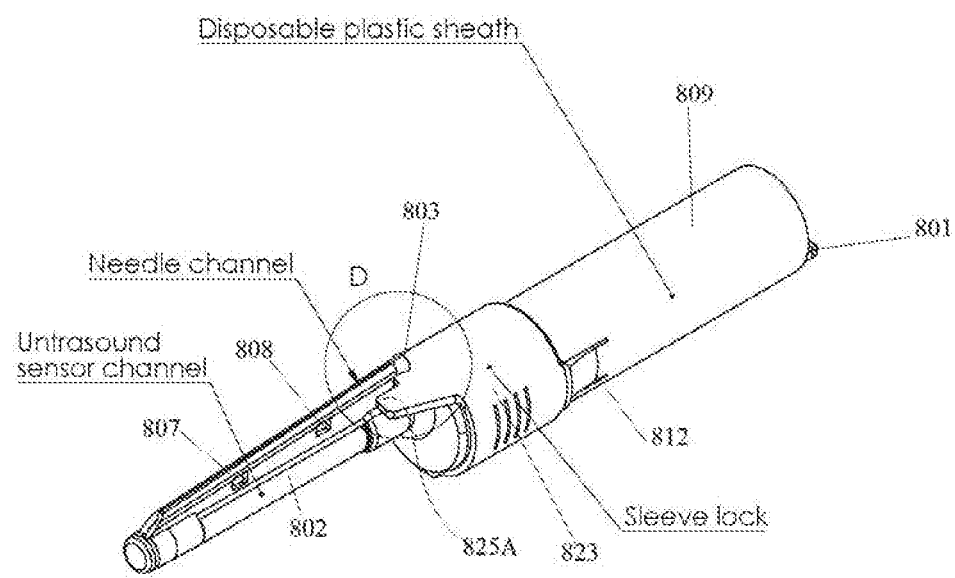
FIG. 8E is a front perspective view of the sensor housing of FIG. 8D. An ultrasound sensor channel 802 is located below the needle channel indicated by button tabs 807 and 808 and needle guide opening 803. The needle channel 803 is closed by a sleeve lock 823 and retained in a closed position by retaining tab 812, the sleeve lock 823 having finger grips as seen and a groove (not visible) which holds the halves of the needle guide 803 together. Also shown are a disposable plastic sheath 809 and locking tab 801 for locking together with a sensor and cable assembly seen in FIG. 10. Circle D will be described in FIG. 8F.

FIG. 8E is a front perspective view of the sensor housing of FIG. 8D. An ultrasound sensor channel 802 is located below the needle channel indicated by button tabs 807 and 808 and needle guide opening 803. The needle channel 803 is closed by sleeve lock 823 and retained in a closed position by flexible retaining tab 812, the sleeve lock 823 having finger grips as seen and a groove (not visible) which holds the halves of the needle guide 803 together. Also shown are a disposable plastic sheath 809 and flexible locking tab 801 for locking together with a sensor and cable assembly seen in FIG. 10. Circle D will be described in FIG. 8F.

Figure 8F:
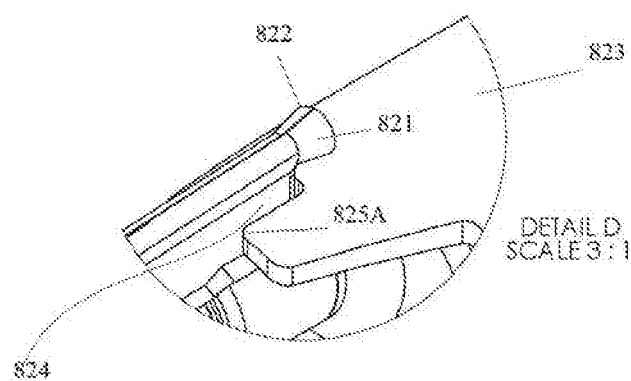
FIG. 8F provides an expanded view (Detail D) of the sleeve lock 823 showing needle guide halves 821, 822 held together in a groove 824 facilitated by quarter-circular section 825A.

FIG. 8F provides an expanded view (Detail D) of the sleeve lock 823 showing needle guide halves 821, 822 held together in a groove 824 facilitated by quarter-circular section 825A (or other arcs of a circle may be used or a straight cut of the groove 824 and needle guide halves such as at a forty-five degree angle.

Figure 8G:
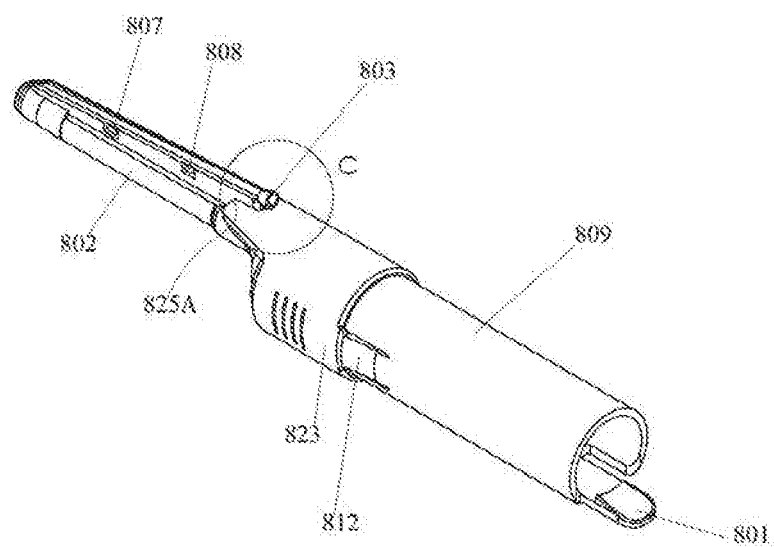
FIG. 8G shows a rear perspective view of the needle guide and sensor housing with locking tab 801, needle guide 803, button tabs 807, 808, sensor housing 803, quarter-circular section 825A of a gripping groove of sleeve lock 823 held in closed position by retaining tab 812 and disposable plastic sheath 809. Circle C will be described with reference to FIG. 8H.

FIG. 8G shows a rear perspective view of the needle guide and sensor housing with flexible locking tab 801, needle guide 803, button tabs 807, 808, sensor housing 803, quarter-circular section 825A of a gripping groove of sleeve lock 823 held in closed position by flexible retaining tab 812 and disposable plastic sheath 809. Circle C will be described with reference to FIG. 8H.

Figure 8H:
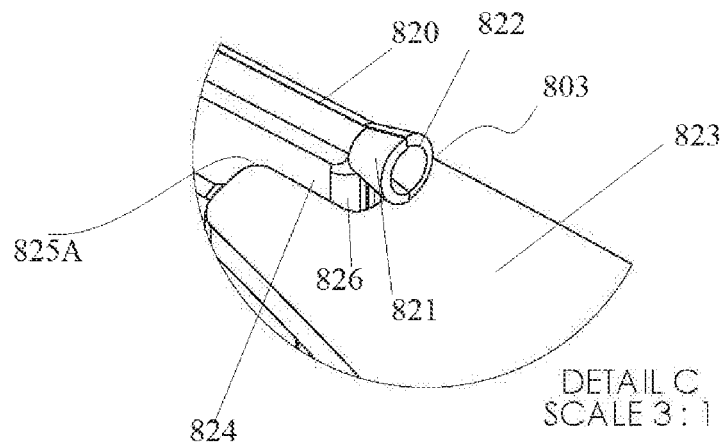

FIG. 8H provides a rear expanded perspective view of the closure of needle guide 803 (Detail C) having flexible halves 821 and 822 within a groove 824 of sleeve lock 823 showing a quarter-circular section 825A for matching with a needle guide quarter-circular section 825 along closure line 820. As explained above, other arcuate cuts of groove 824 may match with arcuate cuts of needle guide halves or a line cut at an angle of approximately forty-five degrees may be applied to close normally open halves 821 and 822

Figure 8I:
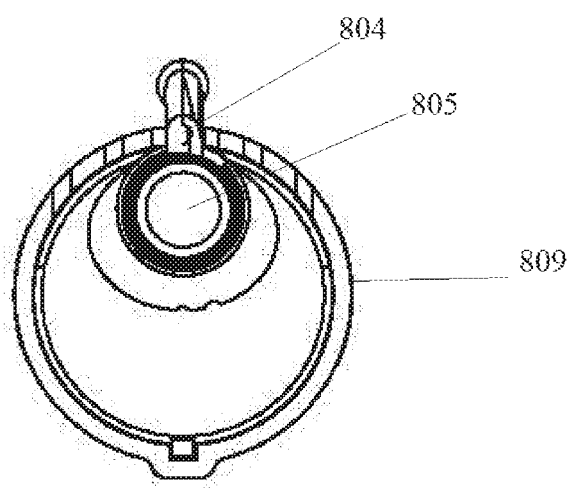
FIG. 8I provides a cross-section of the disposable plastic sheath portion including sheath 809, the needle channel distal tip 804 and the sensor channel tip 805 which may comprise a window for an internal ultrasound transducer assembly (not shown).

FIG. 8I provides a cross-section of the disposable plastic sheath portion including sheath 809, the needle channel distal tip 804 and the sensor channel tip 805 which may comprise a window for an internal ultrasound transducer assembly (not shown).

Figure 9A:
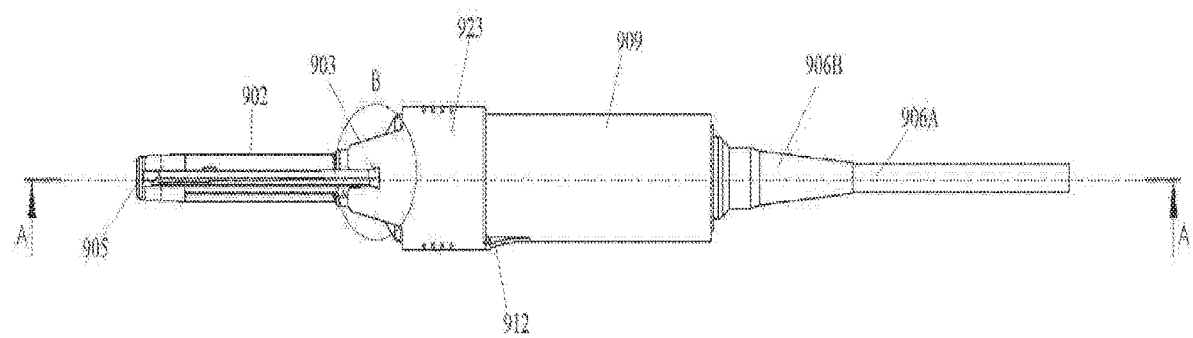
FIG. 9A is discussed, comprises the ultrasound transducer assembly, a probe housing, a sheath and a cable narrowing section and the exiting cable which connects to a processor and display not shown. The ultrasound transducer assembly provides an imaging plane (referred to in earlier patents as an imaging zone) capturing a region of interest originating from the transducer array.
Figure 9B:
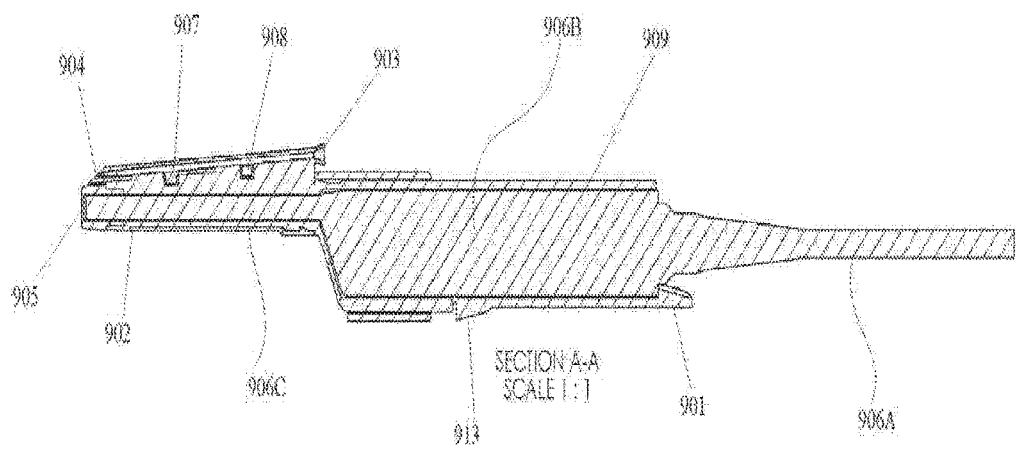
Figure 9C:
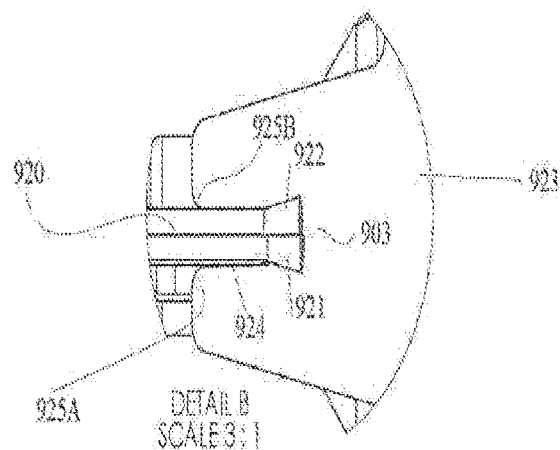
Figure 9D:
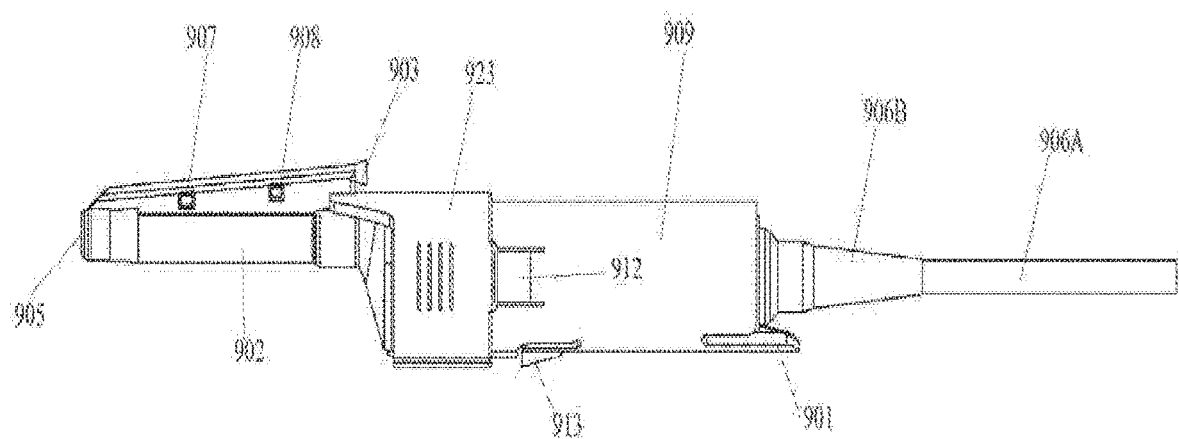
Figure 9E:
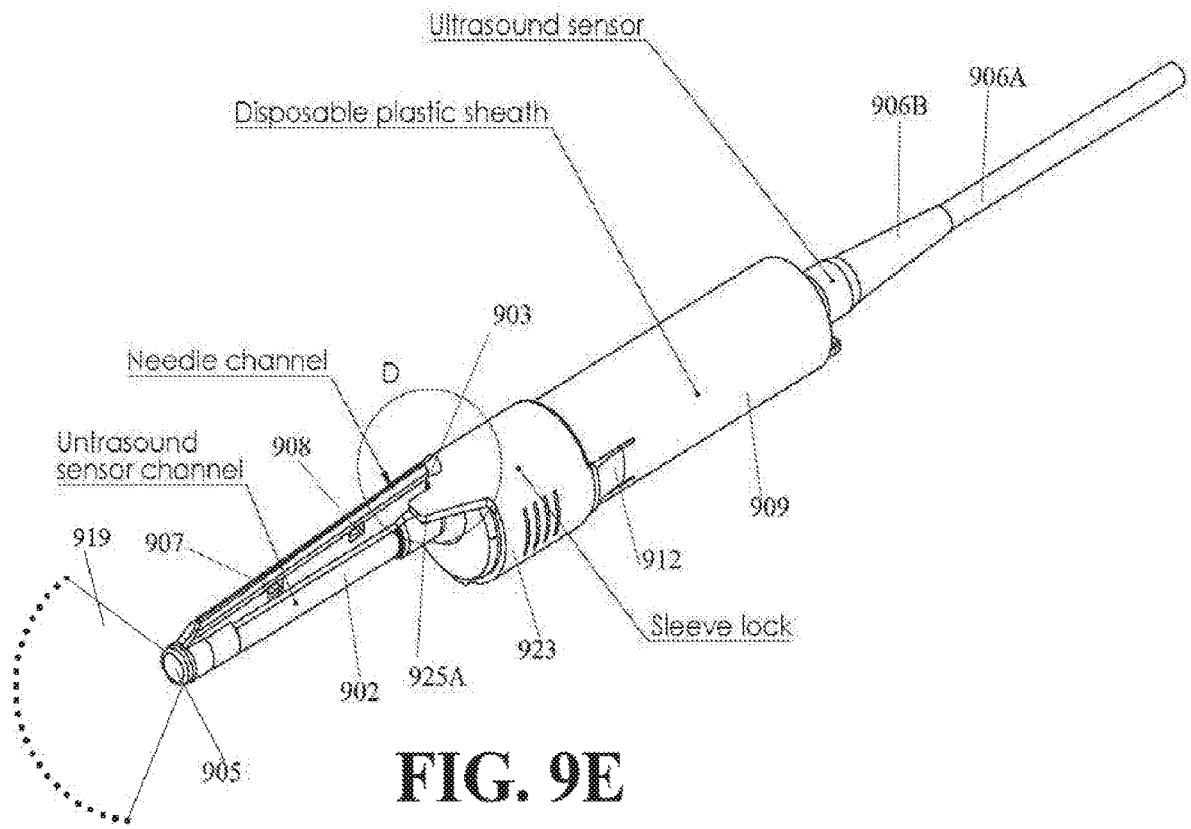
Figure 9F:
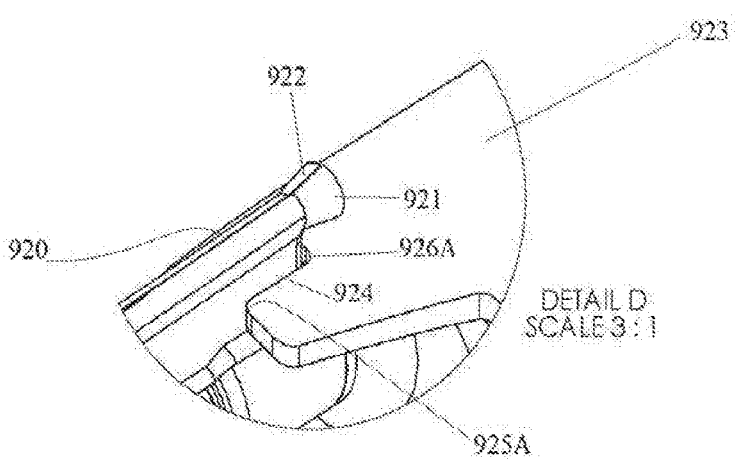
Figure 9G:
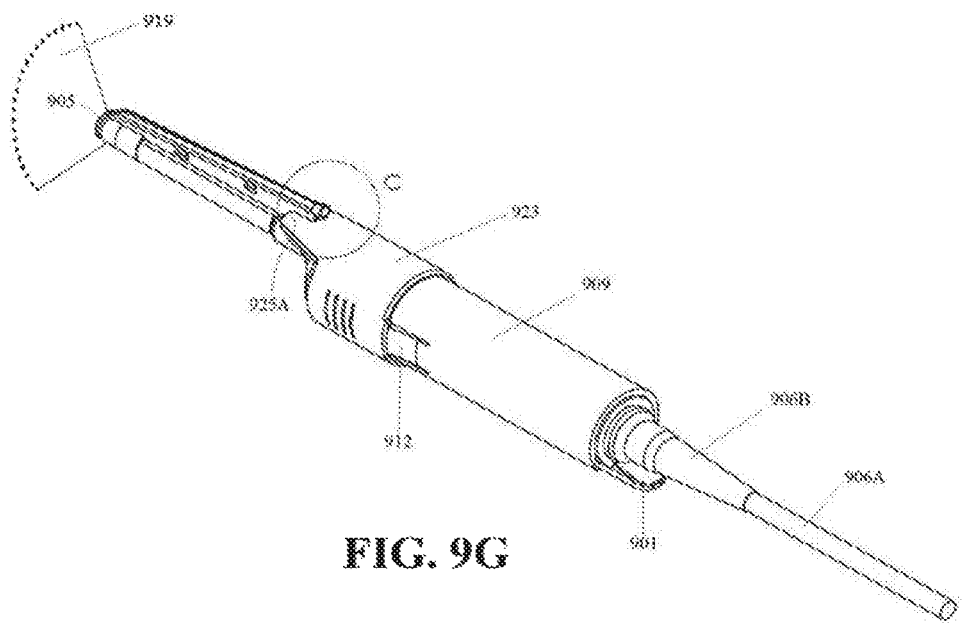
Figure 9H:
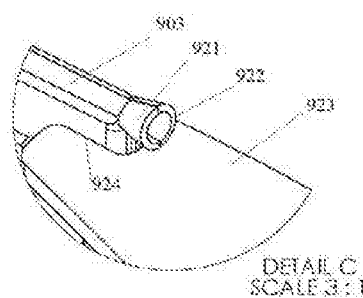
Figure 9I:
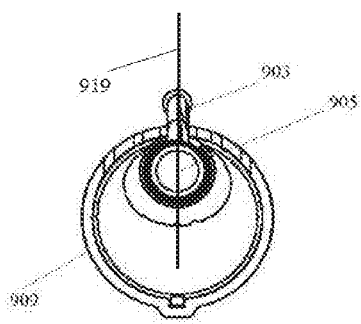

FIGS. 9A through 9I provide views of a combination assembly of the sensor housing and needle guide section (distal or patient end) with the sensor and cabling section (proximal end) using the groove needle guide locking mechanism or sleeve lock 923 as discussed above. Referring to FIGS. 9E and 9I, for example, an imaging plane of a transducer array is aligned with a needle/syringe delivery port so that the imaging plane captures images of the tool as it emerges into the imaging plane and a surgeon need not optimize the delivery of the tool to be seen by reflected ultrasound.

FIG. 9A provides a top view of the combination assembly comprising from left to right sensor channel tip 905 with a needle guide tip directly above but not easily discernable. Sensor channel or probe housing 902 holds, for example, a probe comprising a linear phased array with each element connected to leads of a cable (not seen) until the cable exits at right as cable 906A. Flexible needle guide 903 in flexible halves is shown closed within a groove of circle B. Gripping tab or sleeve lock 923 that may slide back is shown closed and retained by retaining tab 912 so that a groove closes needle guide 903 having flexible halves that close together around a needle, syringe or other tool. Next to the right is disposable sheath 909 and a cable joining section 906B of a probe, probe housing and cable assembly locked together as will be discussed with reference to FIG. 9B.

FIG. 9B is a cross-section along line A-A of FIG. 9A so as to see the internal components of the combination assembly. A right-side cross-section of the assembly comprises from right, cable 906A which merges with cable joining section 906B and the individual piezoelectric element leads pass through sections 906B and 906C (a probe section) to, for example, a linear phased array of elements facing forward at sensor tip 905. A flexible locking tab 901 locks needle guide section 902, 903, 904, 907, 908, along with cable section disposable housing 909 to the internal cable and sensor sections 906A, 906B and 906C.

FIG. 9C is a further exploded top view (Detail B) of the needle guide locking mechanism comprising along closing line 920 a first quarter-circular groove section 925A and an opposite quarter-circular grove section 925B of groove 924 of sleeve lock 923 which close around needle guide halves 921 and 922 to close the needle guide 903. As already discussed, a quarter-circle cut is one of many cuts of the groove 924 and of the halves of the normally open flexible needle guide 903.

FIG. 9D is a complete assembly side view comprising from left to right a sensor tip 905, a sensor probe housing 902, needle guide button tabs 907 and 908 and needle guide 903. The sleeve lock 923 is seen in a closed position so that normally open flexible needle guide 903 would be closed. Disposable plastic sheath 909 is seen next with flexible locking tab 901 holding sensor and cable assembly 906A and 906B in place, mostly internally within the housings/sheaths 902 and 909.

FIG. 9E provides a front perspective view of the entire assembly. Starting from left is seen the sensor housing tip 905, the probe housing 902, needle guide button tabs 907, 908, the flexible, normally open needle channel 903 with sleeve lock 923 having quarter-circular section 925A for locking the needle guide 903 in a groove of sleeve lock 923 in a closed position (Circle D discussed in FIG. 9F) held by flexible retaining tab 912, disposable plastic sheath section 909 (covering cable, not visible and, for example, containing an accelerometer and/or at least one gyroscope for alignment of images with gravity) and ultrasound sensor and cable sections 906B and cable 906A may be seen. When sleeve lock 923 is moved to the rear opening the normally open needle channel 903 via the sleeve lock 923, the sleeve lock 923 is retained by a flexible retaining tab on the bottom of sheath 909. A forward-directed linear phased array may be located just behind sensor tip 905 as will be discussed later herein. An approximately two-dimensional ultrasound imaging plane 919 is shown to be oriented perpendicular to the face of the ultrasound array to the center of the needle port delivery port portion of the sheath; (see also FIG. 9I). This ensures that during a procedure the needle or other tool emerging from the needle guide 903 at its distal port is automatically visible in the ultrasound image without the physician needing to adjust the relative orientation of a sheath or ultrasound probe.

FIG. 9F provides a front perspective view of the needle guide locking mechanism in a closed position along line 920 (Detail D). Sleeve lock 923 locks normally open, flexible needle guide halves 921 and 922 together in a groove 924 having a quarter-circular section 925A and a rear groove face 926A and is retained in closed position by flexible retaining tab 912 (FIG. 9E). As already discussed, other arcuate cuts of the groove 924 and halves 921, 922 will also close the needle guide channel as will an approximately forty-five degree angle cut.

FIG. 9G provides a rear perspective view of the combination assembly from left to right comprising the sensor housing tip 905, the probe housing 902, needle guide button tabs 907, 908, the normally open needle channel 903 with sleeve lock 923 having quarter-circular section 925A for locking the needle guide 903 (in circle C) in a groove of sleeve lock 923, disposable plastic sheath section 909 (covering cable) and ultrasound sensor and cable sections 906B and cable 906A may be seen along with flexible locking tab 901 for holding the outer housing together with the probe and cable assembly inner housing. A forward-directed linear phased array may be located just behind sensor tip 905 as will be discussed herein.

FIG. 9H is an exploded view of Detail C where needle guide halves 921, 922 of needle guide 903 are held together by a groove 924 of sleeve lock 923.

FIG. 9I is very similar to FIG. 8I and shows a cross-section of the disposable plastic sheath portion 909, the needle channel tip and the sensor channel tip 905, the needle channel tip being the end portion of the needle guide 903. The exact orientation of the ultrasound image plane 919 is shown to intersect the center of the imaging array and needle delivery port, thereby ensuring that the needle or other tool being delivered will be visible in a processed ultrasound image (not shown) without the physician having to adjust the relative position of the sheath or ultrasound probe.

FIGS. 10A through 10I depict several views of the above-described needle guide embodiment and probe and cable assembly also including an exemplary needle having a handle 1010 and a tip 1011. The needle 1011 and handle 1010 are shown in the needle channel 1003 having flexible halves. The needle 1010, 1011 may be a biopsy needle and be hollow for collecting tissue at a site of interest or a syringe for removing fluids (for example, during a cardiocentesis) located by forward-imaging of a transducer array located behind sensor tip 1005. Flexible retainer tab 1012 retains sleeve lock 1023 in a closed position and normally open needle guide 1003 is locked closed.

Figure 10B:
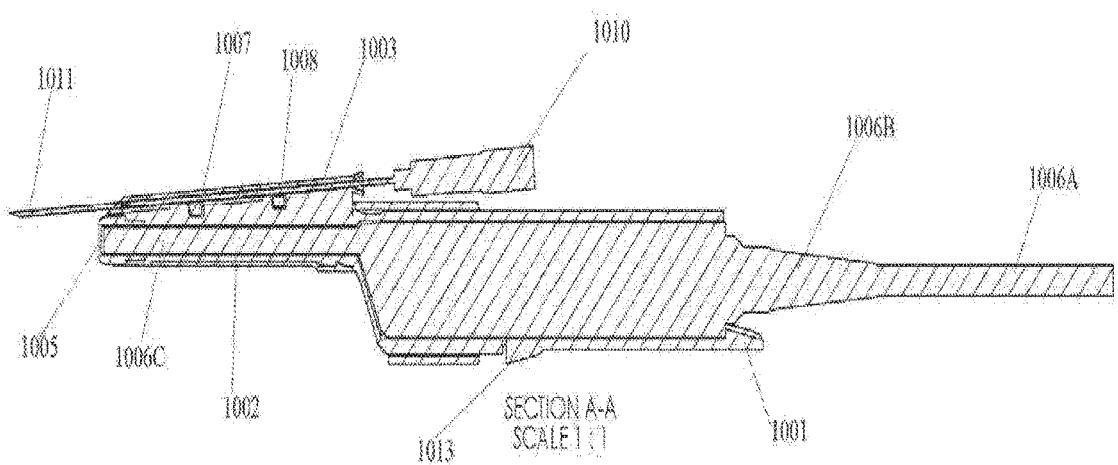

FIG. 10A shows section A-A seen in FIG. 10B. FIG. 10A from left to right includes but is not limited to showing needle tip 1011, closed but normally open needle guide 1003, sleeve lock 1023, needle handle 1010, circle B for explaining the locking mechanism, disposable plastic sheath section 1009; letter A where the locking tab 1001 would be located on the underside and is not visible, locking the entire assembly including cable narrowing section 1006B and cable section 1006A. Needle handle 1010 may comprise a syringe.

FIG. 10B shows section A-A comprising from left to right a needle tip 1011, button tabs 1007 and 1008 which assist in lifting needle 1011 out of the needle channel 1003, sensor tip 1005, probe and cable housing 1006C, piezoelectric element leads 1002, needle handle 1010, flexible locking tab 1001 in the vicinity of A of FIG. 10A, cable narrowing section 1006B and cable section 1006A.

Figure 10C:
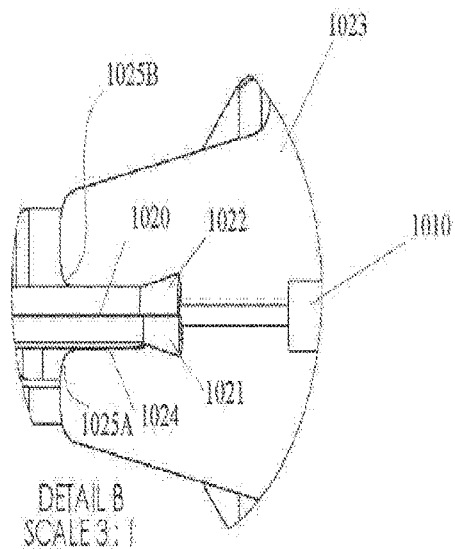

FIG. 10C provides an expanded view of detail B (circle B of FIG. 10A) showing the normally open, flexible needle channel halves 1021, 1022 in a locked and closed position in groove 1024 having been guided into groove 1024 by quarter-circular edges 1025A, 1025B of the distal end of groove 1024 (also other arcs or linear cuts may be used). FIG. 10C also shows needle handle 1010 and a top viewable portion of sleeve lock 1023.

Figure 10D:
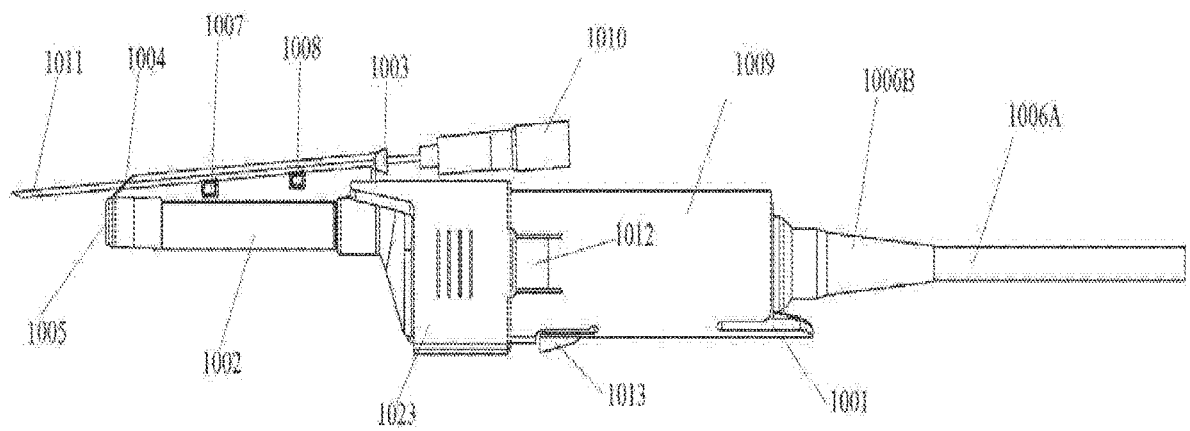

FIG. 10D is a side view of a complete assembly including both a probe and cable housing portion 1005, 1002, 1009, a locking sleeve 1023 held in a closed position by retaining tab 1012, a needle 1011 and handle 1010 held in needle channel 1003 by button tabs 1007, 1008 and a disposable sheath 1009 having a flexible retaining tab 1001 for securing (or releasing) a cable and probe section 1006A, 1006B, 1006C. Retaining tab 1013 stops sleeve lock 1023 from moving rearwards along sheath 1009 but is used during assembly as will be described herein for installing sleeve lock 1023.

Figure 10E:
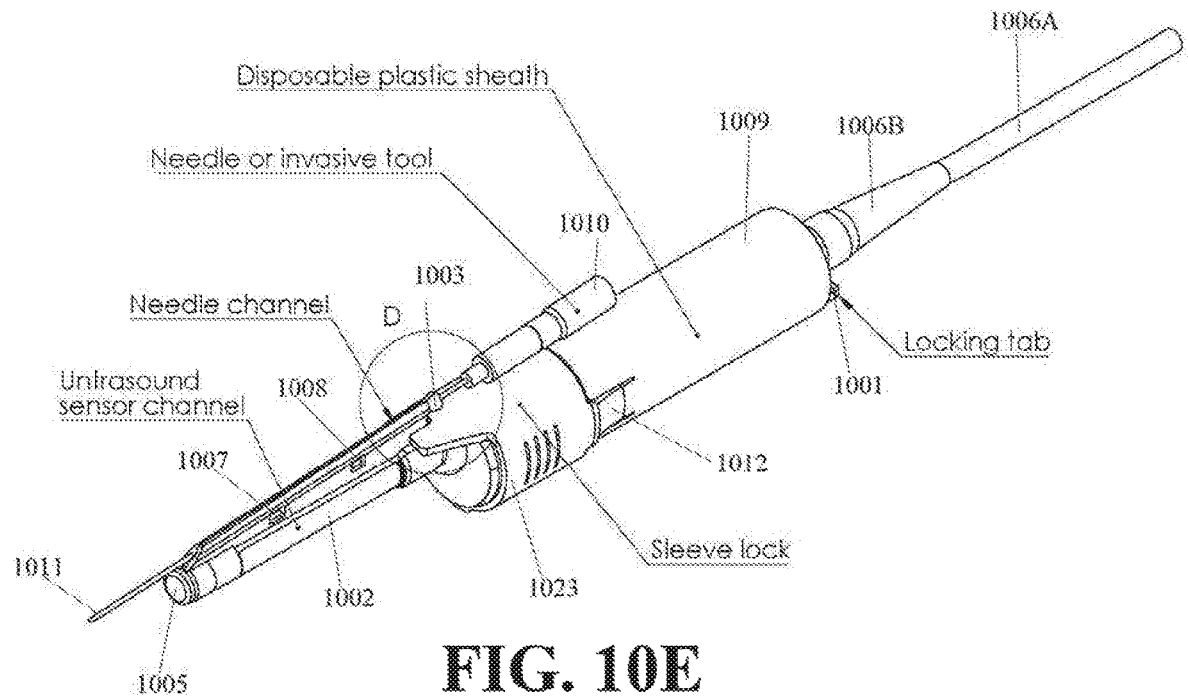

FIG. 10E provides a front perspective view of a complete assembly as seen in FIG. 10D comprising four components, a needle 1011 and needle handle 1010, the needle residing in a needle channel 1003 of a needle guide, the needle 1011 supported by button tabs 1007 and 1008 of the needle guide portion of a probe and cable housing comprising the needle guide, a distal probe tip window 1005, a probe housing 1002 and a disposable sheath 1009 having a flexible locking tab 1001 for locking, for example, a probe containing a linear phased transducer array located behind the window 1005, and element leads to a cable exiting the sheath 1009 via cable narrowing section 1006B while cable 1006A leads to a processor and display (not shown) and the sleeve lock 1023 which is slid down sheath 1009 and over retaining tab 1012 to close needle channel 1003 over needle 1011. Circle D will be discussed with reference to FIG. 10F.

Figure 10F:
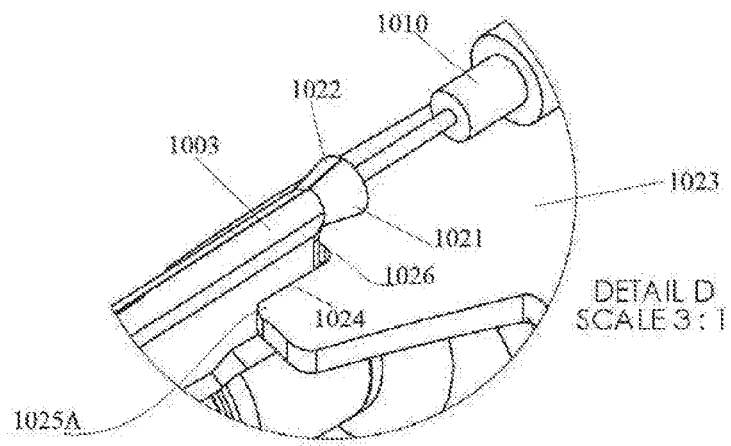

FIG. 10F provides an expanded view of detail D (circle D of FIG. 10E) showing the normally open, flexible needle channel halves 1021, 1022 in a locked position in groove 1024 having been guided into groove 1024 by quarter-circular edges 1025A, 1025B (not visible) of the distal end of groove 1024 joining the two halves 1021, 1022 of needle channel 1003. (A discussion of alternative edges will not be discussed again.) FIG. 10F also shows needle handle 1010 and a top viewable portion of locking sleeve 1023.

Figure 10G:
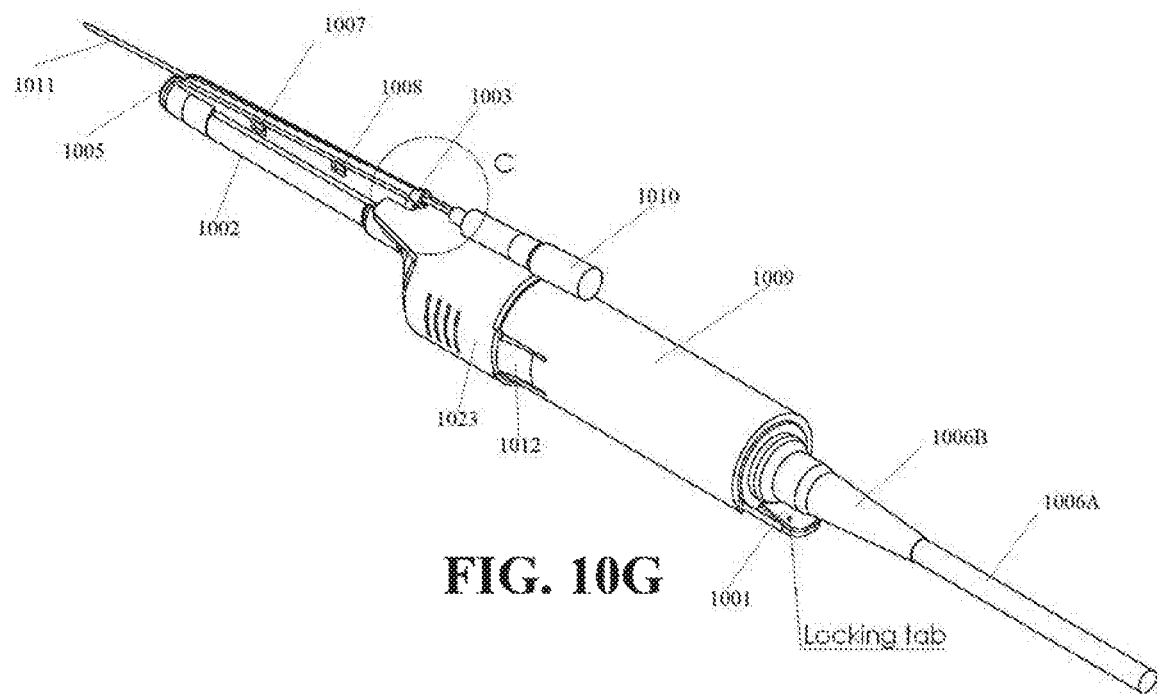

FIG. 10G provides a rear perspective view of a complete assembly as seen in FIG. 10D comprising four components, a needle 1011 and needle handle 1010; the needle 1011 residing in a needle channel 1003 of a needle guide, the needle 1011 supported by button tabs 1007 and 1008 of the needle guide portion of a probe and cable housing comprising the needle guide, a distal probe tip window 1005, a probe housing 1002 and a disposable sheath 1009 having a flexible locking tab 1001 for locking, for example, a probe containing a linear phased transducer array (not shown) located behind the window 1005, and element leads to a cable exiting the sheath 1009 via cable narrowing section 1006B while cable 1006A leads to a processor and display (not shown) and the sleeve lock 1023 which is slid down sheath 1009 during assembly and over retaining tab 1012 to close needle channel 1003 over needle 1011. As already discussed, an accelerometer and/or at least one gyroscope may be located in sheath 1009 for maintaining an image on a display (not shown) in alignment with the gravitational field of the earth. Circle C will be discussed with reference to FIG. 10H.

Figure 10H:
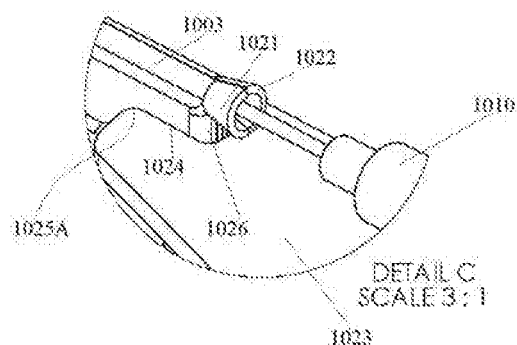

FIG. 10H provides an expanded view of detail C (circle C of FIG. 10G) showing the normally open needle channel halves 1021, 1022 in a locked, closed position in groove 1024 having been guided into groove 1024 by quarter-circular edges 1025A, 1025B (not visible) of the distal end of groove 1024 joining the two halves 1021, 1022 of needle channel 1003 to form a closed needle channel. FIG. 10H also shows needle handle 1010 and a top viewable portion of locking sleeve 1023.

Figure 10I:
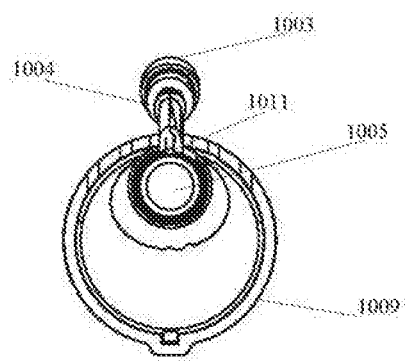

FIG. 10I is very similar to FIGS. 8I and 9I but differs in showing needle tip 1011 emerging from needle guide 1003 and shows a cross-section of the disposable sheath portion 1009, the needle channel tip 1004 and the sensor channel tip 1005 with the end portion of the needle guide 1003.

Figure 11A:
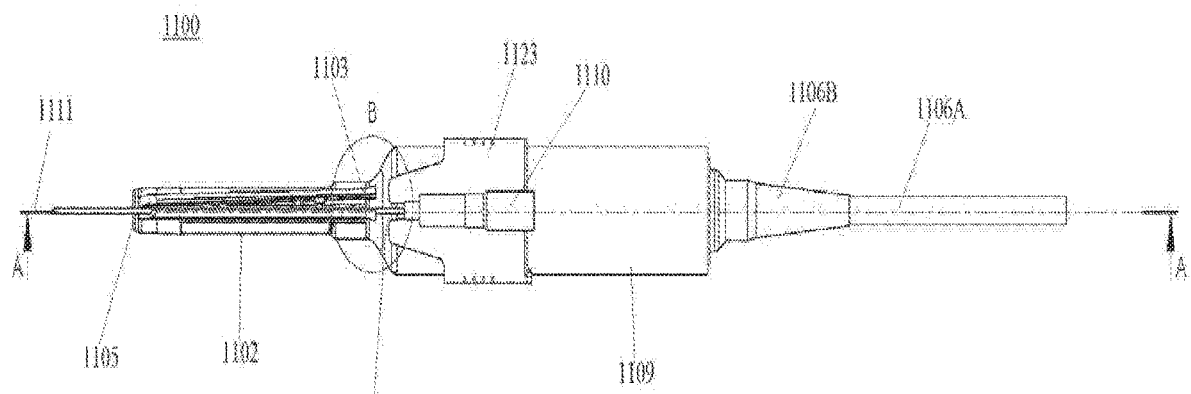
FIG. 11A provides a top view of a complete assembly of an image guided catheter or probe 1100 as seen also in FIG. 10E with sleeve lock 1123 open comprising four components, a needle 1111 and needle handle 1110, the needle still residing in a needle channel 1103 of a needle guide, the needle 1111 supported by button tabs (not visible) of the needle guide portion of a probe and cable housing comprising the needle guide, a distal probe tip window 1105, a probe housing 1102 and a disposable sheath 1109 having a locking tab (not visible) for locking, for example, a probe containing a linear phased transducer array located behind the window 1105, and element leads to a cable exiting the sheath 1109 via cable narrowing section 1106B while cable 1106A leads to a processor and display (not shown) and the sleeve lock 1123 which is slid down sheath 1109 and over retaining tab (not visible) to close needle channel 1103 over needle 1111 via groove 1124. Circle B will be discussed with reference to FIG. 11C. Cross-section A-A will be discussed with reference to FIG. 11B.

FIG. 11A provides a top view of a complete assembly of an image guided catheter or probe 1100 as seen also in FIG.

10E with sleeve lock 1123 open comprising four components, a needle 1111 and needle handle 1110, the needle still residing in a needle channel 1103 of a needle guide, the needle 1111 supported by button tabs (not visible) of the needle guide portion of a probe and cable housing comprising the needle guide, a distal probe tip window 1105, a probe housing 1102 and a disposable sheath 1109 having a flexible locking tab (not visible) for locking, for example, a probe containing a linear phased transducer array located behind the window 1105, and element leads to a cable exiting the sheath 1109 via cable narrowing section 1106B while cable 1106A leads to a processor and display (not shown) and the sleeve lock 1123 which is slid down sheath 1109 and over retaining tab (not visible) to close needle channel 1103 over needle 1111 via groove 1124. Circle B will be discussed with reference to FIG. 11C. Cross-section A-A will be discussed with reference to FIG. 11B.

Figure 11B:
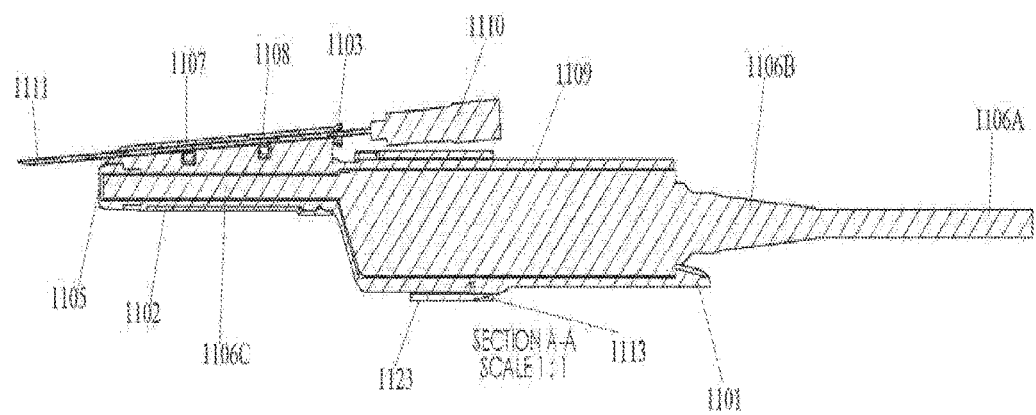
FIG. 11B provides a cross-section view of a complete assembly along A-A of FIG. 11A and comprises four components, a needle 1111 and needle handle 1110, the needle 1111 residing in a needle channel 1103 of a needle guide, the needle 1111 supported by button tabs 1107, 1108 of the needle guide portion of a probe and cable housing comprising the needle guide located at the top, a distal probe tip window 1105, a probe housing 1102 and a disposable sheath 1109 having a locking tab 1101 for locking, for example, a probe containing a linear phased transducer array located behind the window 1105 seen as section 1106C, and element leads (not shown) to a cable section 106A exiting the sheath 1109 via cable narrowing section 1106B while cable 1106A leads to a processor and display (not shown) and the sleeve lock 1123 which is slid down sheath 1109 and over retaining tab 1113 to close needle channel 1103 over needle 1111 via groove 1124. The needle channel 1103 is open and sheath 1123 has not been moved toward the distal tip 1105 to close the needle channel 1103.

FIG. 11B provides a cross-section view of a complete assembly along A-A of FIG. 11A and comprises four components, a needle 1111 and needle handle 1110, the needle 1111 residing in a needle channel 1103 of a needle guide, the needle 1111 supported by button tabs 1107, 1108 of the needle guide portion of a probe and cable housing comprising the needle guide located at the top, a distal probe tip window 1105, a probe housing 1102 and a disposable sheath 1109 having a flexible locking tab 1101 for locking, for example, a probe containing a linear phased transducer array located behind the window 1105 seen as section 1106C, and element leads (not shown) to a cable section 1106A exiting the sheath 1109 via cable narrowing section 1106B while cable 1106A leads to a processor and display (not shown) and the sleeve lock 1123 which is slid down sheath 1109 and over retaining tab 1113 to close needle channel 1103 over needle 1111 via groove 1124. The needle channel 1103 is normally open and sheath 1123 has not been moved toward the distal tip 1105 to close the normally open needle channel 1103.

Figure 11C:
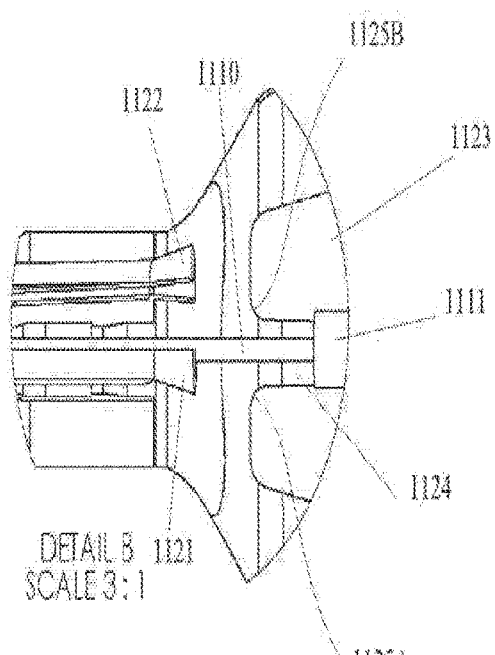
FIG. 11C provides an expanded view of Detail B of FIG. 11A showing the needle channel open and comprises the needle channel halves 1121, 1122 in an open, unlocked position outside groove 1124 having been released from groove 1124 and quarter-circular edges 1125A, 1125B of the distal end of groove 1124 releasing the two halves 1121, 1122 of needle channel 1003 to expose to view needle 1110 with its handle 1111 also visible.

FIG. 11C provides an expanded view of Detail B of FIG. 11A showing the needle channel open and comprises the flexible needle channel halves 1121, 1122 in a normally open, unlocked position outside groove 1124 having been released from groove 1124 and quarter-circular edges 1125A, 1125B of the distal end of groove 1124 releasing the normally open two halves 1121, 1122 of needle channel 1003 to their open state to expose to view needle 1110 with its handle 1111 also visible. FIG. 11C also shows needle handle 1111 and a top viewable portion of locking sleeve 1123.

Figure 11D:
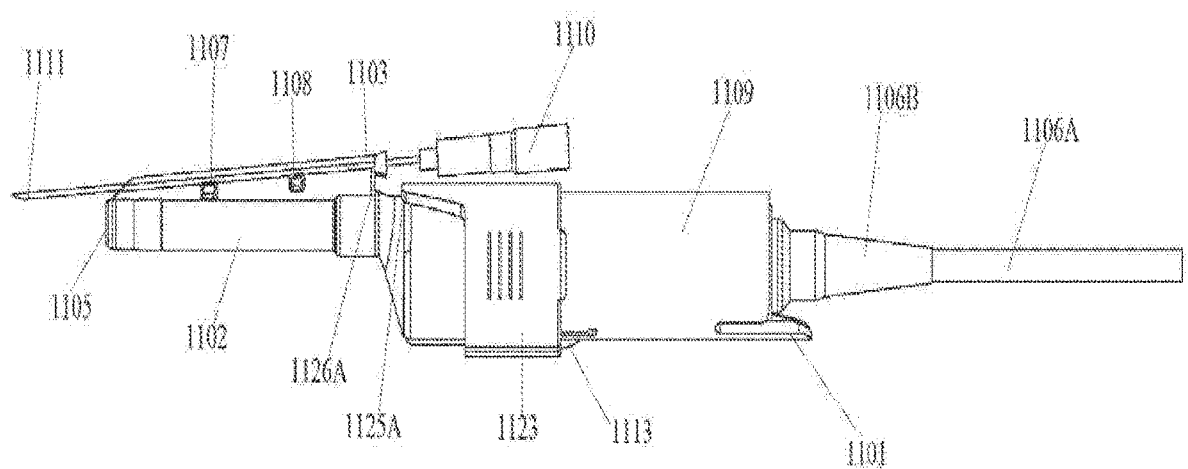
FIG. 11D provides a side view of the complete assembly of four parts with the needle channel 1103 open but the needle 1111 and needle handle 1110 still residing in the needle channel. Locking sheath 1123 has been moved toward the proximal end to be stopped by retaining tab 1113. From left to right, imaging window 1105 of probe housing 1102 has mounted thereon a needle guide comprising button tabs 1107, 1108 supporting needle 1111 in needle channel 1103. At the end of needle channel 1103 is seen a quarter-circular edge of the channel which mates with quarter-circular edge 1125A of groove of open sheath 1123 when closed but, when open, locking sheath 1123 rests against retaining tab 1113 and surrounds sheath 1109. Locking tab 1101 locks in probe and cable assembly comprising a cable narrowing section 1106B leading to cable 1106A.

FIG. 11D provides a side view of the complete assembly of four parts with the needle channel 1103 open but the needle 1111 and needle handle 1110 still residing in the open needle channel 1103. Locking sheath 1123 has been moved toward the proximal end to be stopped by retaining tab 1113. From left to right, imaging window 1105 of probe housing 1102 has mounted thereon a needle guide comprising button tabs 1107, 1108 supporting needle 1111 in open needle channel 1103. At the end of needle channel 1103 is seen a quarter-circular edge of the channel which mates with quarter-circular edge 1125A of groove of open sheath/sleeve 1123 when closed but, when open, sleeve lock 1123 rests against retaining tab 1113 and surrounds sheath 1109. Locking tab 1101 locks in probe and cable assembly comprising a cable narrowing section 1106B leading to cable 1106A.

Figure 11E:
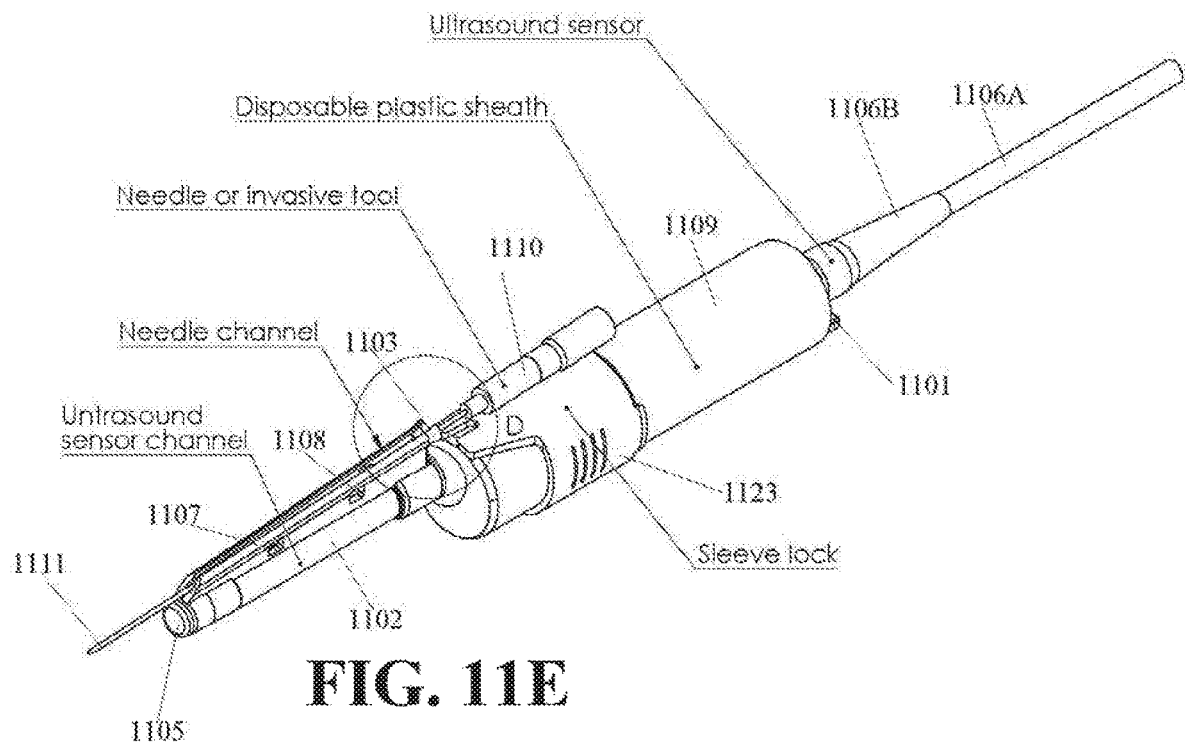
FIG. 11E is a front perspective view of a complete assembly with the needle channel 1103 open and the needle 1111 and needle handle 1110 are exposed and are supported on button tabs 1107 and 1108 of the needle guide. From left, the probe housing tip or window 1105 is seen on probe housing 1102 while sleeve lock 1123 is shown open on disposable sheath 1109. Locking tab 1101 locks probe and cable section within comprising visible cable narrowing section 1106B and cable 1106A. Circle D will be described with reference to FIG. 11F. Needle handle 1110 may comprise a syringe having two cylindrical sections.

FIG. 11E is a front perspective view of a complete assembly with the needle channel 1103 open and the needle 1111 and needle handle 1110 are exposed and are supported on button tabs 1107 and 1108 of the normally open needle guide. From left, the probe housing tip or window 1105 is seen on probe housing 1102 while sleeve lock 1123 is shown open (moved proximally) on disposable sheath 1109. Flexible locking tab 1101 locks probe and cable section within comprising visible cable narrowing section 1106B and cable 1106A. Circle D will be described with reference to FIG. 11F. Needle handle 1110 may comprise a syringe having two cylindrical sections.

Figure 11F:
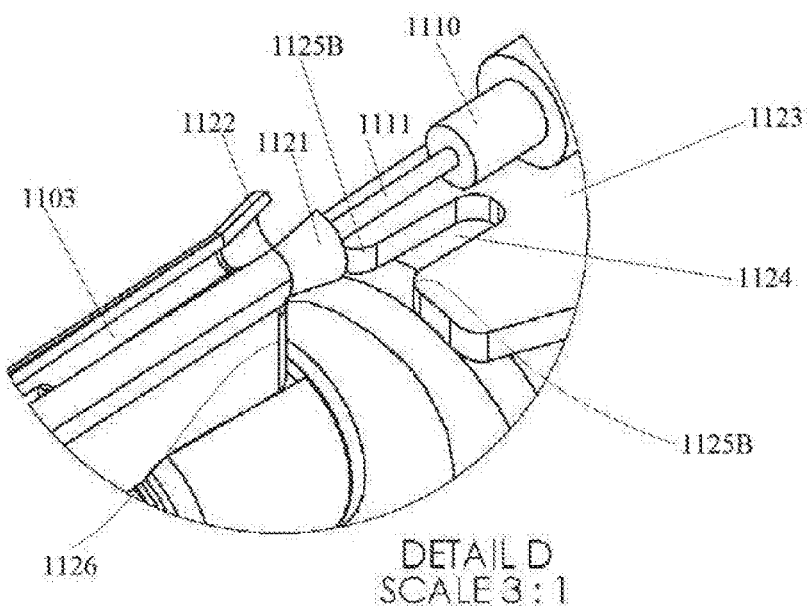
FIG. 11F is an expanded view of detail D of FIG. 11E showing the needle channel halves 1121, 1122 open exposing to view needle 1111 and needle handle 1110 and comprises the needle channel halves 1121, 1122 in an open, unlocked position outside groove 1124 having been having been released from groove 1124 and quarter-circular edges 1125A, 1125B of the distal end of groove 1124 releasing the two halves 1121, 1122 of needle channel 1103 to expose to view needle 1111 with its handle 1110 (which may comprise a syringe) also visible.

FIG. 11F is an expanded view of detail D of FIG. 11E showing the normally open needle channel halves 1121, 1122 open exposing to view needle 1111 and needle handle 1110 and comprises the needle channel halves 1121, 1122 in an open, unlocked position outside groove 1124 having been released from groove 1124 and quarter-circular edges 1125A, 1125B of the distal end of groove 1124 releasing the two halves 1121, 1122 of needle channel 1103 to expose to view needle 1111 with its handle 1110 (which may comprise a syringe) also visible. FIG. 11F also shows needle handle 1110 and a top viewable portion of locking sleeve 1123.

Figure 11G:
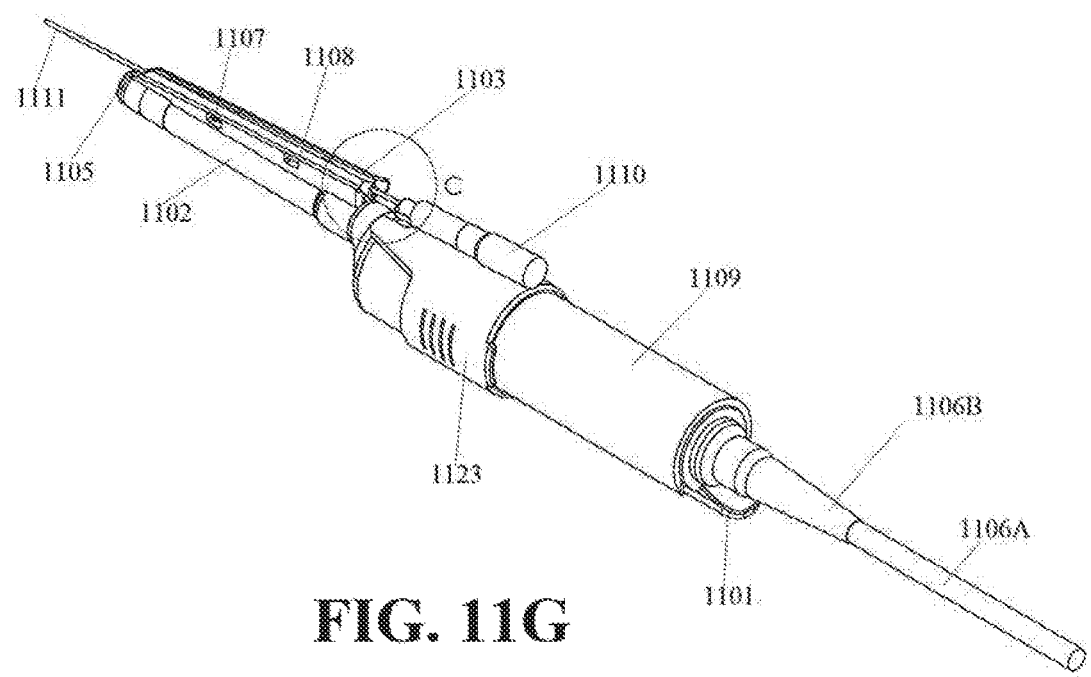
FIG. 11G is a rear perspective view of the complete assembly with the needle channel 1103 open and the needle 1111 and needle handle 1110 are exposed and are supported on button tabs 1107 and 1108 of the needle guide. From left, the probe housing tip or window 1105 is seen on probe housing 1102 while sleeve lock 1123 is shown open on disposable sheath 1109. Locking tab 1101 locks probe and cable section within, the section comprising visible cable narrowing section 1106B and cable 1106A. Circle C will be described with reference to FIG. 11H. Needle handle 1110 may comprise a syringe having two cylindrical sections, one for holding fluid and a pull handle for withdrawn fluid through needle 1111.

FIG. 11G is a rear perspective view of the complete assembly with the normally open, flexible needle channel 1103 open and the needle 1111 and needle handle 1110 are exposed and are supported on button tabs 1107 and 1108 of the open needle guide. From left, the probe housing tip or window 1105 is seen on probe housing 1102 while sleeve lock 1123 is shown open (slid proximally) on disposable sheath 1109. Flexible locking tab 1101 locks probe and cable section within, the section comprising visible cable narrowing section 1106B and cable 1106A. Circle C will be described with reference to FIG. 11H. Needle handle 1110 may comprise a syringe having two cylindrical sections, one for holding fluid and a pull handle for withdrawn fluid through a hollow needle 1111.

Figure 11H:
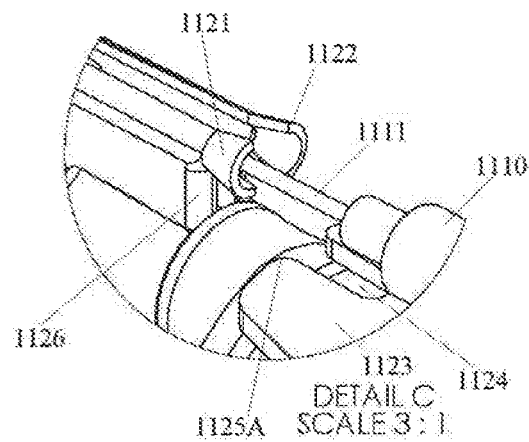
FIG. 11H is an expanded view of detail C of FIG. 11G showing the needle channel halves 1121, 1122 open exposing to view needle 1111 and needle handle 1110 and comprises the needle channel halves 1121, 1122 in an open, unlocked position outside groove 1124 having been having been released from groove 1124 and quarter-circular edges 1125A, 1125B of the distal end of groove 1124 releasing the two halves 1121, 1122 of needle channel 1103 to expose to view needle 1111 with its handle 1110 (which may comprise a syringe) also visible.

FIG. 11H is an expanded view of detail C of FIG. 11G showing the needle channel halves 1121, 1122 open exposing to view needle 1111 and needle handle 1110 and comprises the normally open, flexible needle channel halves 1121, 1122 in an open, unlocked position outside groove 1124 having been having been released from groove 1124 and quarter-circular edges 1125A, 1125B of the distal end of groove 1124 releasing the normally open two halves 1121, 1122 of needle channel 1103 to expose to view needle 1111 with its handle 1110 (which may comprise a syringe) also visible. FIG. 11H also shows needle handle 1110 and a top viewable portion of locking sleeve 1123.

Figure 11I:
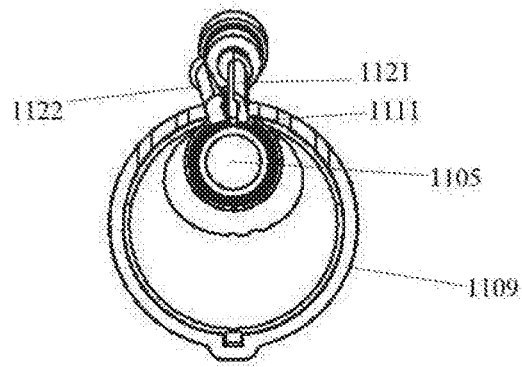
FIG. 11I is a top perspective expanded cross-sectional view showing open needle channel 1103 comprising needle channel halves 1121 and 1122 in an open position. Needle 1111 has handle 1110 shown still inside the needle open channel 1103 comprising halves 1121 and 1122.

FIG. 11I is a top perspective expanded cross-sectional view showing open needle channel 1103 comprising normally open needle channel halves 1121 and 1122 in an open position. Needle 1111 has handle 1110 shown still inside the open needle channel 1103 comprising halves 1121 and 1122 also open. FIG. 11I further shows cross-section 1109 of disposable sheath 1109 and the probe window or distal probe housing end 1105.

FIGS. 12A through 12I are identical to FIGS. 11A through 11I but for the movement of needle 1211 and handle 1210 vertically out of the needle channel 1203 and will not be described in any detail to avoid redundancy. However, FIG. 12I will be briefly explained as it shows the needle 1111 and handle 1110 removed from the open needle channel vertically.

Figure 12A:
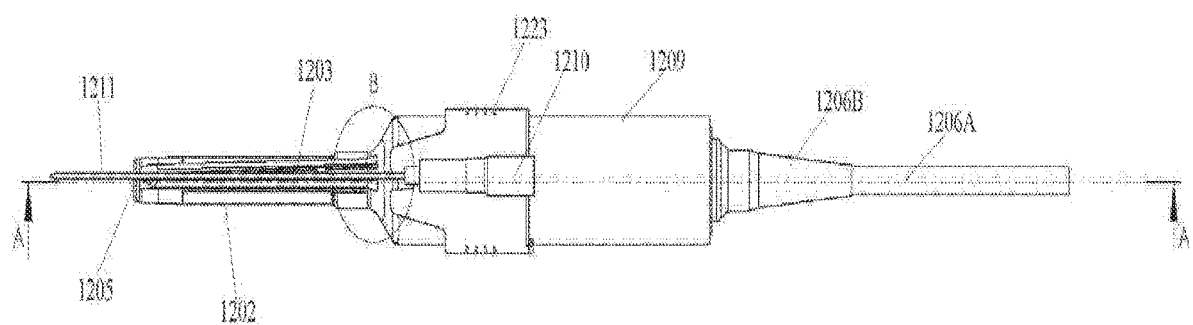
Figure 12B:
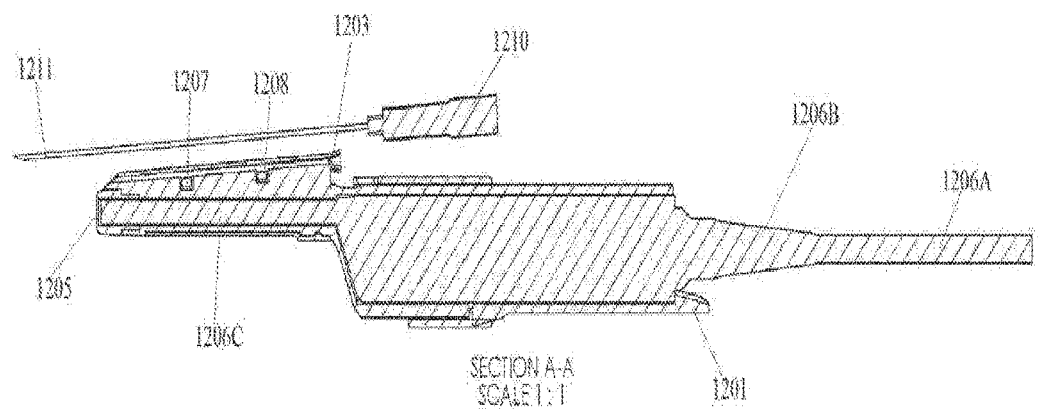
Figure 12C:
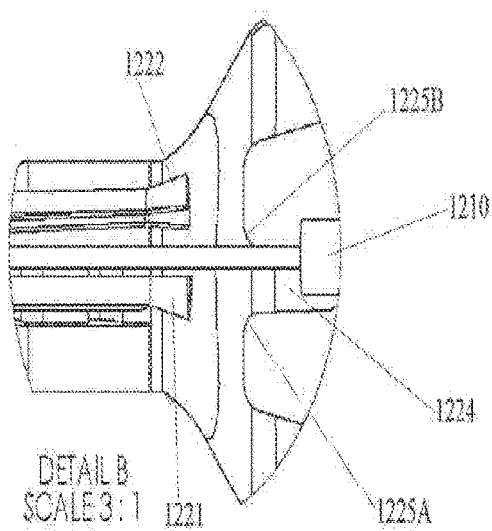
Figure 12D:
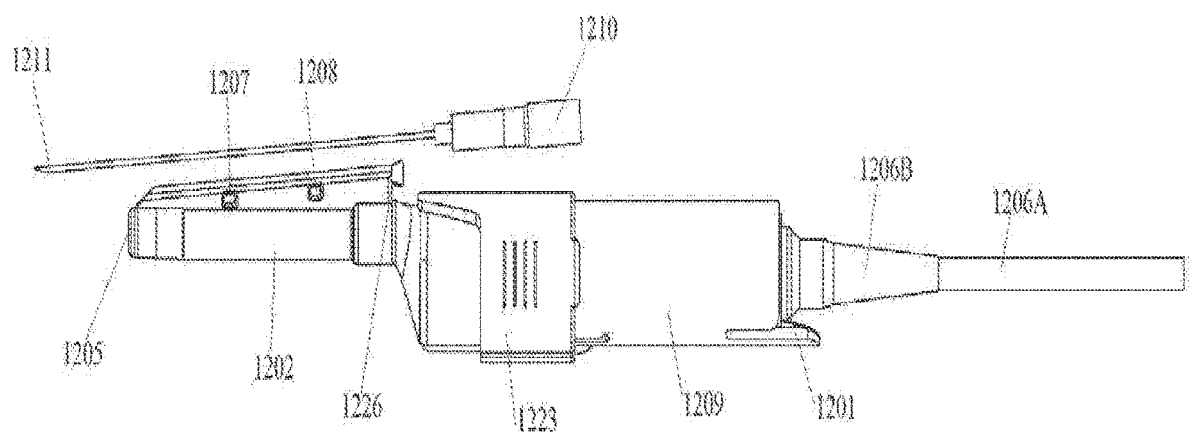
Figure 12E:
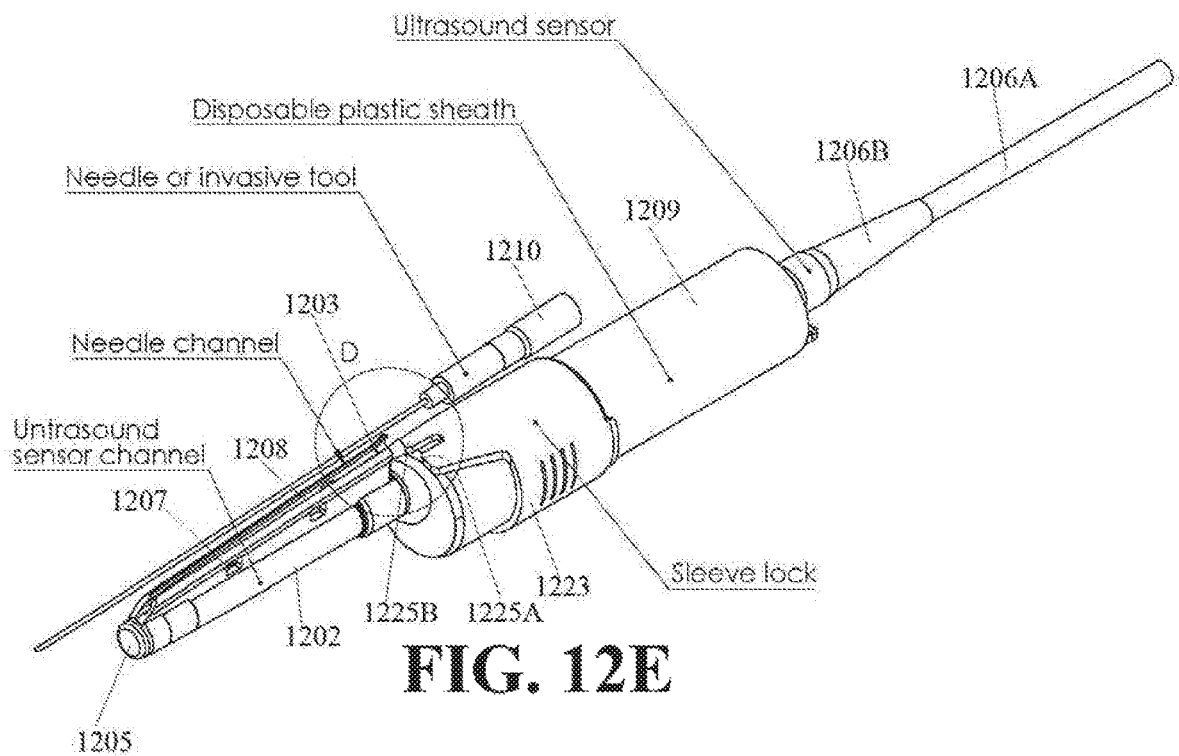
Figure 12F:
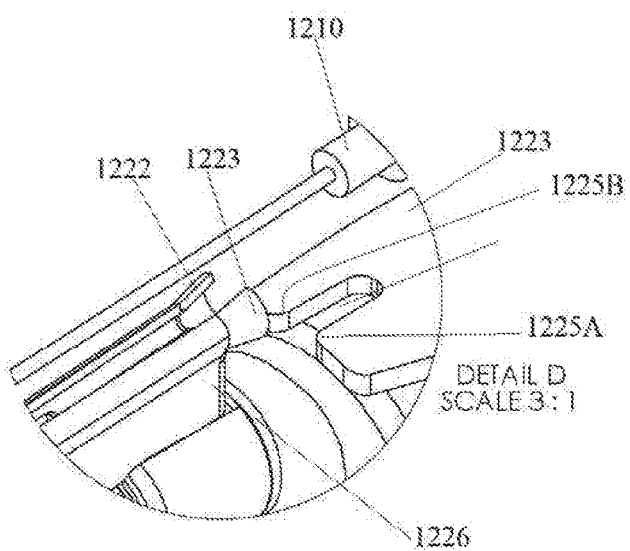
Figure 12G:
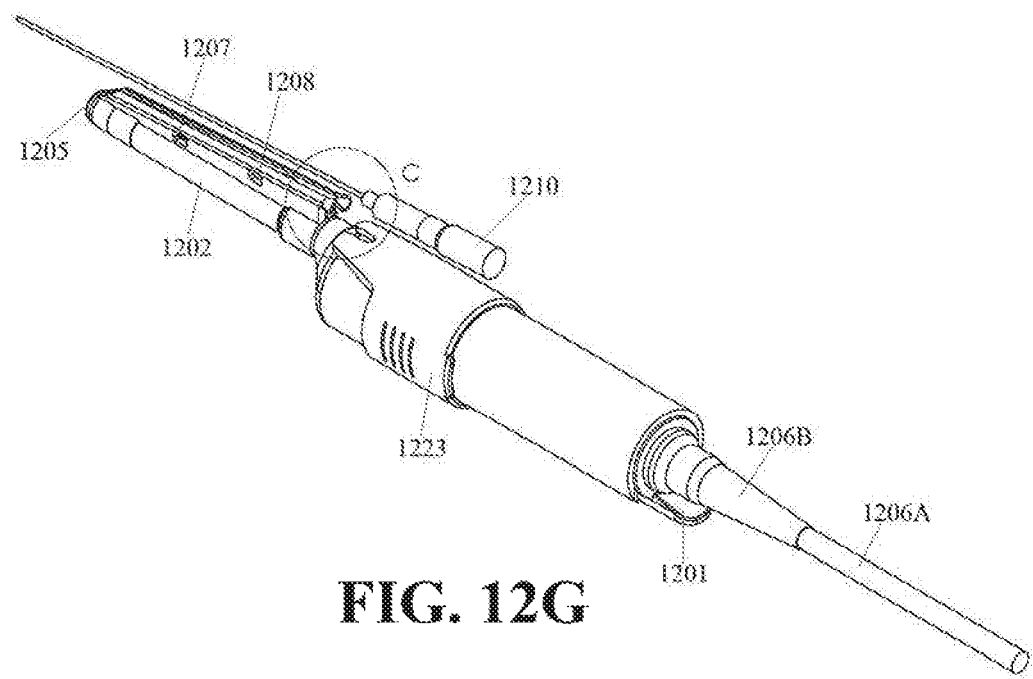
Figure 12H:
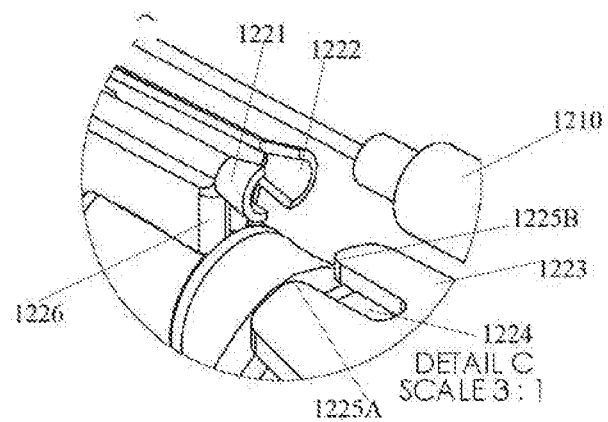
Figure 12I:
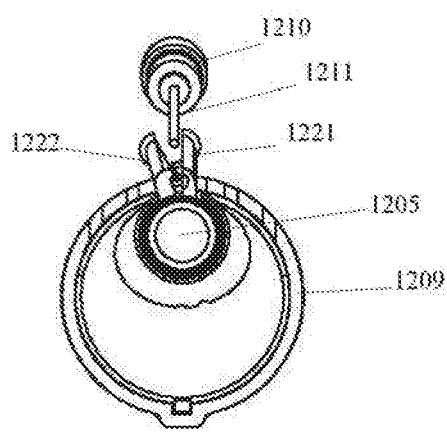

FIG. 12I shows needle handle 1210 and needle 1211 removed vertically and outside the open needle channel comprising open needle channel halves 1221 and 1222. Probe distal end 1205 is seen as is the sheath section 1209 in cross-section.

FIGS. 13 through 17B provide an overview of the insertable probe, cable and linear phased array transducer assembly 1006A, 1006B, 106C, that is locked by a flexible locking tabs 101, 201, 501, 801, 901, 1001, for example, inside disposable sheaths 102, 202, 502, 909, 1009, for example.

Figure 13:
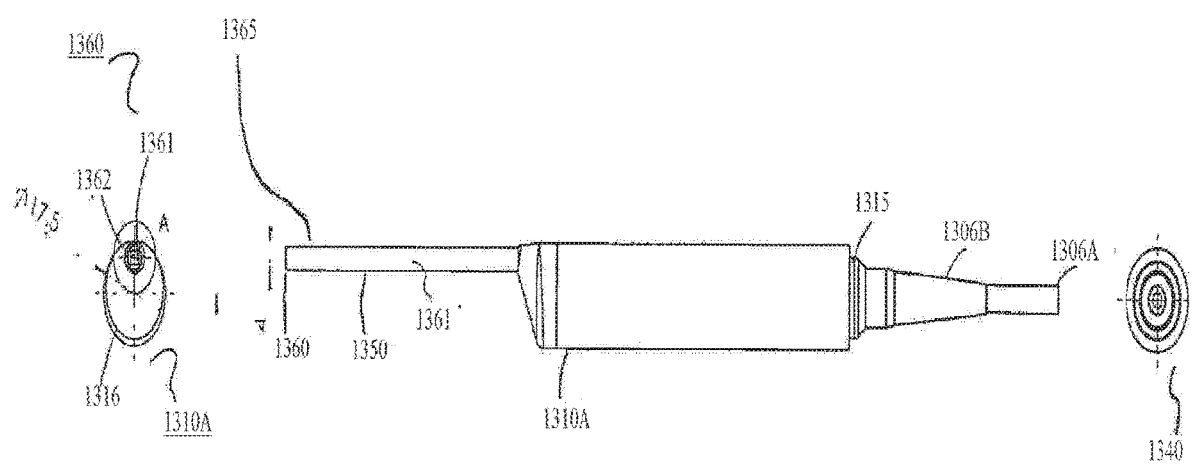

FIG. 13 provides a side view at its center of a plurality ultrasonic elements (not visible) of a transducer probe according to the present invention which may have a protective sheath (for example, sheath or probe housing 702 of FIG. 7) disposed between the probe 1361 located toward the distal tip 1360. All distances if any are shown are approximate and may be changed for different applications such as reaching the heart pericardial sac (also known as the pericardial space) versus reaching a melanoma close to the skin or a kidney with an anterior approach with optimized resolution and are shown in millimeters. A convention used in the brief and detailed description is that a reference numeral YXX may be used wherein the Y provides the Figure number where an element first appears and the XX (which may be any two-digit number) may represent the reference numeral of the element (used consistently for a similar component), for example, transducer array 1362 comprises Y for FIG. 13 and XX for numeral 62 which represents the transducer array while element 1310A represents the cylindrical housing 1310A shown in FIG. 13 held within disposable sheath, for example, 1109 by a surgeon (not shown in this figure series). To the left of FIG. 13, is seen a cross-section of a plane of housing 1310A including both the probe 1361 and the cylindrical housing 1310A. At the right of FIG. 13 is shown a cross-section 1340 intended to show the radially placed elements of the outer cylindrical housing 1310A, cable transition portion 1206B, the strain relief feature and the cable 1206A including, for example, the twenty-three leads to the transducer linear phased array, shown by way of example, which in turn leads to a display processor and display. Views 1361, 1362, 1316 are shown enlarged as FIGS. 14A (end view) and 14B (cross-sectional top view) of exemplary linear phased array elements 1462-1 through 1462-23.

Figure 14A:
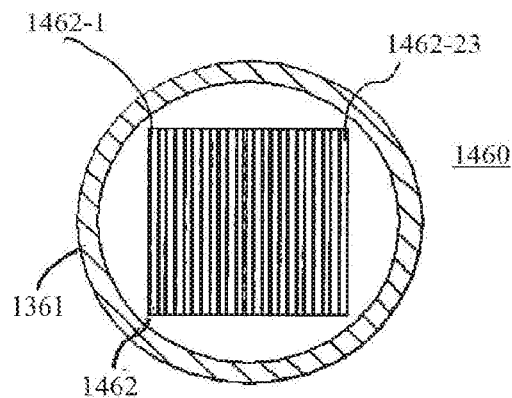
FIG. 14A shows a first exemplary embodiment of a front view of an exemplary ultrasound linear phased array having, for example, twenty-three linear elements 1462-1 through 1462-23 of, for example, 0.1 millimeters pitch (approximately one lambda wavelength of an exemplary center frequency of fifteen megahertz) making a total array 1362, 1462 of about 2.3 millimeters by 2.3 millimeters. A ½ λ embodiment may also be used as is known in the art with the complication that the number of elements of the array may increase the size of a cable to a processor and display (not shown). Not shown in FIG. 14A or distal tip 1360 of FIG. 13 is that the linear phased array may be protected within a dome, flat window, no window, or tapered window of the housing including the needle guide and when actuated generates an image plane discussed above with intersects with a needle delivery port of a needle guide so as to capture an image of any needle/syringe/sheath/tool emerging into the imaging plane. A probe shaft cylindrical housing 1410A (FIG. 14B) is seen that may have a circular cross-sectional shape that is approximately four millimeters in diameter as seen in FIG. 13. Not shown, the probe shaft cylindrical housing 1410A may contain electrical leads to the linear phased array transducer array 1362 and an accelerometer and/or one or more gyroscopes having signal leads which will align any image on a display with the gravitational field of the earth. One transducer array may be replaced with another transducer array having a different center frequency and similar one lambda pitch and still fit within the outer probe housing diameter, for example, four millimeters. A more conventional ½ λ pitch may be used in alternative embodiments, a possible problem being the number of diameter of leads forming a cable from the distal to the proximal end of the catheter. The array 1362 may comprise individual linear phased array transducer elements comprising a one by twenty-three linear array shown as elements individually numbered 1462-1 through 1462-23. The white area between the linear phased transducer array 1362 and the housing 1361 is un-numbered and comprises a potting material 1464 seen best in top-down cut-away view FIG. 14B. As described above these array elements 1462-1 through 1462-23 for different center frequency may be contained within a probe insertable into a disposable outer housing, FIGS. 1 through 12I so that transducer arrays may be exchanged for different applications of the probe.
Figure 14B:
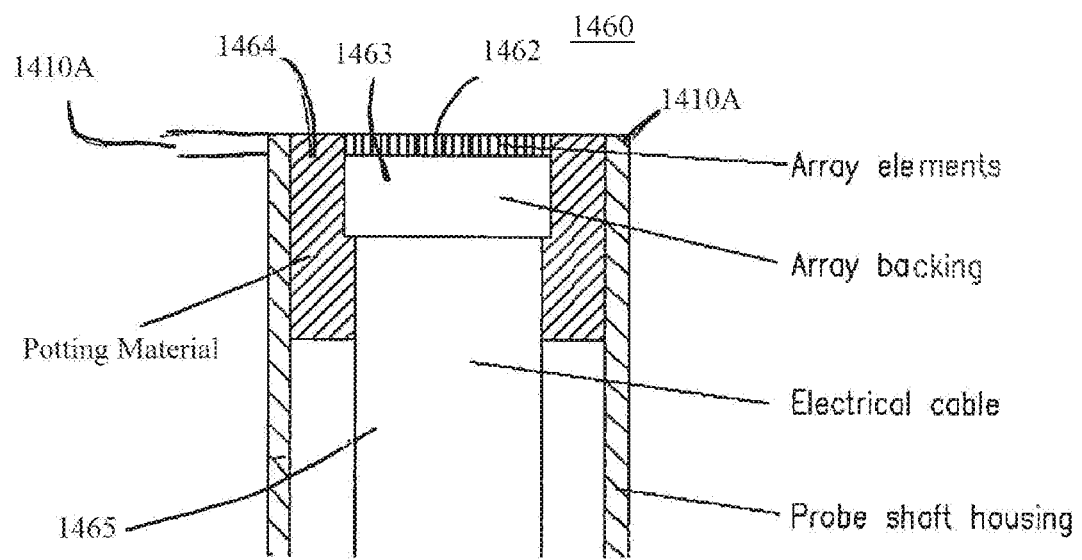
FIG. 14B shows a top sectional 1460 comprising the distal tip and, in particular, comprises from left to right a cross-hatched probe shaft housing 1410A, an array potting material 1464 to firmly grasp the linear phased array elements 1462-1 through 1462-23 (FIG. 14A). Below the section 1460, there is seen at the center of the probe shaft housing 1460, an aperture for conducting an electrical signal cable 1465, narrowing the signal cable 1465 from the diameter of cable channels to piezoelectric elements 1462, the leads carrying signals to/from the linear phased array elements 1462-1 through 1462-23 via the array backing 1463. The aperture is preferably walled as shown and extends the entire length of the probe shaft housing, carrying the electrical cable 1465.

FIG. 14A shows a first exemplary embodiment of a front view of an exemplary ultrasound linear phased array having, for example, twenty-three linear elements 1462-1 through 1462-23 of, for example, 0.1 millimeters pitch (approximately one lambda wavelength of the center frequency of fifteen megahertz) making a total array 1362, 1462 of about 2.3 millimeters by 2.3 millimeters for a center frequency of approximately fifteen megahertz. The center frequency for a probe linear phased array may be selected within a range of ten to forty megahertz, and each piezoelectric element may have a pitch of between 0.85 to 1.15 times the wavelength of the selected center frequency. A more conventional pitch or 0.5 to 0.6λ may also be used but will increase the number of cable leads to the array and may impact subcutaneous use due to need for a larger diameter probe. Not shown in FIG. 14A or distal tip 1360 of FIG. 13 is that the linear phased array may be protected within a dome, flat window, no window, or tapered window of the housing including the needle guide. On the other hand, a window at distal tip 105 of a probe housing per FIG. 1A, for example, may comprise a dome or window protecting the transducer array. A probe shaft cylindrical housing 1410A (FIG. 14B) is seen that may have a circular cross-sectional shape that is approximately four millimeters in diameter as seen in FIG. 13. Not shown, the probe shaft cylindrical housing 1410A may contain electrical signal leads to the linear phased transducer array 1362 for transmitted and reflected ultrasound signals and an accelerometer and/or at least one gyroscope having leads which produce signals which when processed may be used to align any image on a display (not shown) with the gravitational field of the earth. One transducer array may be replaced with another transducer array having a different center frequency and similar one lambda or a conventional half lambda pitch (but more linear elements) and still fit within the outer probe housing diameter, for example, four millimeters. The array 1362 may comprise individual linear phased array transducer elements comprising a one by twenty-three linear array shown as elements individually numbered 1462-1 through 1462-23. More elements would be needed for a conventional array of linear elements at one half lambda pitch. The white area between the linear phased transducer array 1362 and the housing 1361 is un-numbered and comprises a potting material 1464 seen best in top-down cut-away view FIG. 14B. As described above these array elements 1462-1 through 1462-23 for different center frequency may be contained within a probe insertable into a disposable outer housing, FIGS. 1 through 12I so that transducer arrays may be exchanged for different applications of the probe.

FIG. 14B shows a top sectional 1460 comprising the distal tip and, in particular, comprises from left to right a cross-hatched probe shaft housing 1410A, an array potting material 1464 to firmly grasp the linear phased array elements 1462-1 through 1462-23 (FIG. 14A). Below the section 1460, there is seen at the center of the probe shaft housing 1410A, an aperture for conducting an electrical signal cable 1465, narrowing the signal cable 1465 from the diameter of cable channels to piezoelectric elements 1462, the leads carrying signals to/from the linear phased array elements 1462-1 through 1462-23 via the array backing 1463. The aperture is preferably walled as shown and extends the entire length of the probe shaft housing, carrying the electrical cable 1465.

Figure 15A:
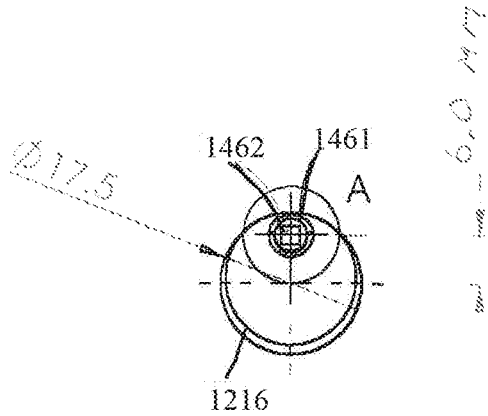
FIG. 15A is a blow-up of the left side cross-section of FIG. 13. There is a section labeled 1216 intended to represent a thicker portion of the hollow cylindrical housing 1310A of FIG. 13. A pair of broken lines, perpendicular to one another signifies the center of the cylindrical housing 1310A. Similarly, a pair of solid lines perpendicular to one another signifies the center of the probe shaft housing in circle A such that the distance between the two centers may be approximately six millimeters and the diameter (shown as a single line and arrow tip) of the cylindrical housing 1310A may be approximately 17.5 millimeters.

FIG. 15A is a blow-up of the left side cross-section of FIG. 13. There is a section labeled 1316 intended to represent a thicker portion of the hollow cylindrical housing 1310A of FIG. 13. A pair of broken lines, perpendicular to one another signifies the center of the cylindrical housing 1310A. Similarly, a pair of solid lines perpendicular to one another signifies the center of the probe shaft housing in circle A such that the distance between the two centers may be approximately six millimeters and the diameter (shown as a single line and arrow tip) of the cylindrical housing 1310A may be approximately 17.5 millimeters (within a range of, for example, twelve to twenty-five millimeters).

Figure 15B:
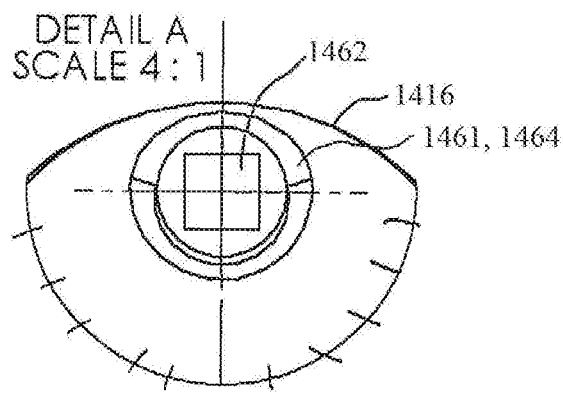
FIG. 15B is a blow-up of detail A of FIG. 15A showing the relationship between the linear phased transducer array 1462, its probe shaft 1461 which may comprise potting material 1464 and the outer wall 1416 of the cylindrical housing 1310A. The partial circular line is intended to show that wall 1416 only represents a portion of cylindrical housing 1310A and should not be considered a part of the image guided probe which may be reusable and removable from the outer sheaths depicted in Figures described above.

FIG. 15B is a blow-up of detail A of FIG. 15A showing the relationship between the linear phased transducer array 1462, its probe shaft 1461 which may comprise potting material 1464 and the outer wall 1416 of the cylindrical housing 1310A. The partial circular line is intended to show that wall 1416 only represents a portion of cylindrical housing 1310A and should not be considered a part of the image guided probe which may be reusable and removable from the outer sheaths depicted in Figures described above.

Figure 16:
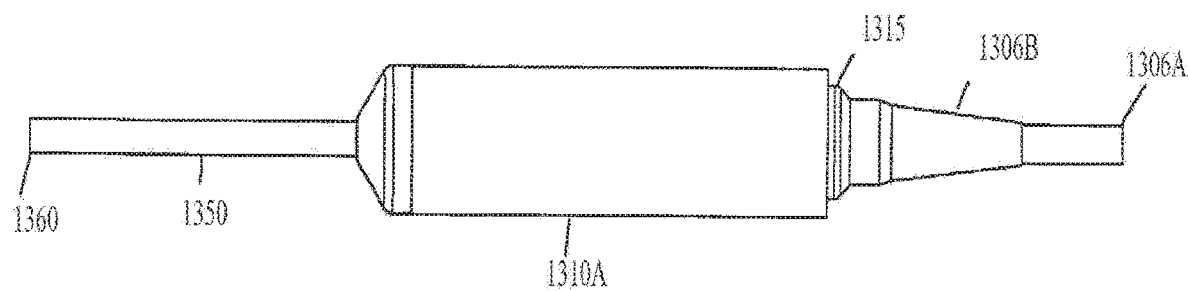

FIG. 16 provides either a top-down view or a bottom-up view of the image guided probe at the center of FIG. 13 (without showing details of any sheath for protecting the probe so that the probe housing is reusable). The view shows the probe 1350's distal end 1360 where would be located the linear phased transducer array 1462 of the present invention. The center section is the cylindrical housing 1310A that is covered by a disposable sheath that may be grasped and utilized by a surgeon. The section transition feature 1315 provides a side view of an example transition between the probe's cylindrical cable housing 1310A and the cable strain relief feature 1306B which provides the exit of cable 1306A from the imaging probe for image processing and display.

Figures 17A, 17B:
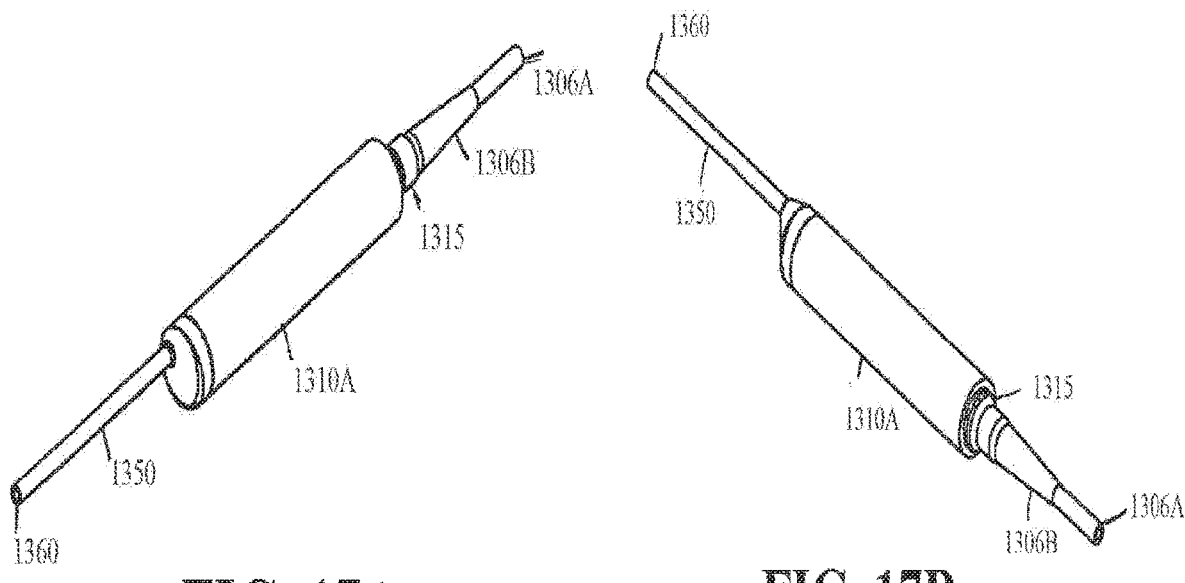

FIG. 17A is a left front perspective view of an image guided probe comprising distal probe end 1360, probe shaft 1350, cylindrical housing 1310A, transition feature 1315, flexible cable section 1306B and cable 1306A from left to right.

FIG. 17B is a right rear perspective view of an image guided probe showing the same components in the same order as is seen in FIG. 17A from upper left to lower right.

Assembly of a device 1000 will now be described with reference to FIGS. 10A and 10B starting with section 1009, 1002, 1005. The sleeve lock 1023 is introduced from the right (proximal end or surgeon end) by passing sleeve lock 1023 over sheath 1009 via flexible locking tab 1001. The sleeve lock is moved toward the distal end and passes over flexible retaining tab 1013 where it is locked between an open and a closed (distal) position. With the sleeve lock proximate to tab 1013, the normally open needle channel is open so that needle 1011 and handle 1010 may simply be lain vertically unto button tabs 1007 and 1008 within the channel. Then, the sleeve lock 1023 may be moved forward over flexible retaining tab 1012 to lock the needle channel and secure the needle 1011 within the normally open needle channel 1003, now closed around the needle. The needle and handle may be moved forward and back.

The cable and probe section assembly 1006A, 1006B and 1006C may then be slid in from the proximal (surgeon side) and locked in place by the flexible locking tab 1001. The surgeon may adjust the needle 1011 and handle 1010 within the needle guide. The surgeon may start with a solid introducer needle to puncture skin tissue. A sheath may be slid over the solid introducer needle if its tip is at a medical procedure site via external or internal imaging. If subcutaneous entry of the probe is desired, the probe may follow the introducer needle into the skin tissue puncture made by the introducer needle. The introducer needle, depending on the procedure may be followed by replacing the introducer needle with a hollow biopsy needle or a syringe via the sheath. Any viewed needle, syringe or sheath may be rendered echogenic following the methods and procedures described in U.S. Provisional Application 62/526,170, filed Jun. 28, 2017. A pacer placement procedure for installing and securing a pacer through the heart pericardium is described in U.S. provisional patent application Ser. No. 62/527,865, filed Jun. 30, 2017, incorporated by reference as to its entire contents. This is one example of the use of an embodiment of the present device 1000. In a similar manner, and without subcutaneous use of the probe housing 105 (only use of the needle of the needle guide), cardiocentesis may be performed by first creating a path with a needle 1011 via the needle guide to inside a pericardial space having excess fluid. The needle is covered with a sheath under ultrasound vision and a syringe is used and its needle inserted within the pericardial space for removal of excess fluid under vision. Further U.S. provisional patent application Ser. No. 62/527,905 filed Jun. 30, 2017, incorporated by reference as to its entire contents may be referred to for replacement of a heart valve using the present device 1000. Similarly, a needle is used to place a sheath and an expanding umbrella and tools for defective heart valve removal or applied through the sheath under vision and a replacement heart valve inserted replacing the defective heart valve. Other procedures have and will be discussed herein using an embodiment of device 1000 using different components of different dimensions and different medical procedure capabilities.

In some embodiments, device 1000 (with or without an optional handle) can be steerable and externally controlled by the operator. In some embodiments, one or more Micro-Electro-Mechanical Systems (MEMS) devices can be incorporated into the use of the device 1000 to allow an operator to control aspects of the device. MEMS systems can include, for example, mechanical elements (beams, cantilevers, diaphragms, valves, plates, and switches), sensors, actuators, and electronics. Referring to FIG. 7A of U.S. patent application Ser. No. 13/847,902, (now U.S. Pat. No. 9,149,257), a MEMS position manipulator 701 can be mounted on device 100 at a distal portion of device 100 to control a position of transducer 210 to, for example, standard position 702, Position A 702a or Position B 702b. In other embodiments, one or more MEMS devices can be provided to function as tiny sensors and actuators. For example, MEMS can be incorporated in the device for measuring and monitoring pressure in the stomach or other organs in which the catheter is inserted, and for measuring and monitoring blood pressure when performing cardiac catheterization. According to the present invention, the tool may be provided with an echogenic surface to improve visibility (see U.S. provisional patent application Ser. No. 62/526,170 filed Jun. 28, 2017 for use of echogenicity) and a contrast agent used if appropriate for the procedure to improve ultrasound visibility of blood vessels.

In another embodiment, for example, as shown in FIG. 7B of U.S. patent application Ser. No. 13/847,902, (now U.S. Pat. No. 9,149,257) a MEMS manipulator lead fixation device 703 can be provided to permit an operator to remotely access a portion of a device within a patient's body. For example, MEMS manipulator 703 can be used to screw in a lead for a pacemaker implanted in a patient or directly mount a pacemaker to the pericardium without the use of electrical stimulation leads which are typically planted in the pericardium according to known procedures. Alternatively, MEMS manipulator 703 can be used to operate a biopsy needle, syringe, sheath or other tool or to manipulate a suture-application device within a patient. It should be noted that these uses are exemplary only and that a device 1000 capable of using a MEMS manipulator as described herein can be used to access or manipulate any device in a body or for any other suitable purpose.

In accordance with aspects described herein, a device 1000 may have a biopsy instrument such as, for example, the biopsy device depicted in FIGS. 8A-8D of U.S. patent application Ser. No. 13/847,902, (now U.S. Pat. No. 9,149,257). In such an embodiment, device 1000 can be adapted for use in biopsy procedures including but not limited to myocardial biopsy, brain biopsy (nasal cavity or ear canal entry to the brain is possible without probe entry), muscle biopsy, lung biopsy, liver biopsy, kidney biopsy, uterine and ovarian biopsy, esophageal biopsy, stomach biopsy, intestinal biopsy, tumor biopsy (anywhere), targeted biopsy of potentially abnormal zones in any of the above items (e.g., ultrasound or OCT guided biopsy of an abnormal area in the liver or kidney with the present catheter will allow access to the abnormal area, identification of abnormal zones by deploying the ultrasound and biopsy instrument to the specific area of interest) As such, device 1000 can, in some cases, be used in the form of a catheter or probe for delivery of a sheath-like device that is insertable through small incisions in the body. A biopsy tool could be inserted through the needle channel of the device 1000 as could a syringe needle. As used herein, device 1000 generally refers to any embodiment of an image catheter device or probe of the present invention, for example, with or without a handle, with a tapered or flat end, with a tab or a sleeve lock to close the needle channel around a tool, the device 1000 having, for example, an imaging channel 1003 and a needle/instrument channel mounted with the needle guide on top of the ultrasound probe or the probe mounted side by side or with the needle/instrument needle guide assembly being fixable to the device 1000 or removable and replaceably attached to the probe housing and with varying size or diameter of barrel or probe housing depending on the application.

In another embodiment, such as is shown in FIGS. 9A and 9B of U.S. patent application Ser. No. 13/847,902, (now U.S. Pat. No. 9,149,257), device 1000 can include a retrieval instrument in combination with a bioptome or another custom instrument. As is known in the art, a bioptome can comprise a specialized biopsy catheter/probe for use in cardiac applications, particularly a catheter/probe with a special end designed for obtaining endomyocardial biopsy samples. In use, a bioptome can be threaded through the needle lumen of the device 1000 to the right ventricle, where it can snip small tissue samples from the septal wall for pathologic examination. In other uses, a bioptome tip device can be used to monitor heart transplantation patients for early signs of tissue rejection. In use, as seen in FIGS. 9A and 9B of U.S. patent application Ser. No. 13/847,902, (now U.S. Pat. No. 9,149,257), a retrieval instrument having a bioptome 903 can be in closed position 901 at a distal end and closed position 904 at a proximal end to assist in inserting the instrument into the area of interest, and then can be placed into an open position 902 at the distal (patient) end so that the desired tissue can be retrieved for examination or testing. A tissue sample collected by either a retrieval instrument, a biopsy tool, or a bioptome may be removed for analysis either by threading the instrument out of the body through the needle or sheath lumen, or by removing the entire device from the patient's body along with the tissue sample.

Device 1000 in accordance with one or more aspects described herein can have many different embodiments for many different uses within the scope and spirit of the present disclosure. Device 1000 can be in the form of a catheter and a placed needle can carry a small diameter, minimally invasive sheath to a medical procedure site that provides entry into various body spaces, thus allowing therapy delivery, intervention, placement of devices and diagnostics. Device 1000 can also be in the form of interventional devices for use in procedures within these spaces. Such catheters, probes, sheaths, and devices are known, and, thus, the general features of device 1000 for these embodiments can be in accordance with conventional devices.

In addition, when provided with one or more integrated transducers (such as linear phased arrays) and other components required to provide ultrasound imaging as described herein, device 1000 can be used in a wide variety of procedures which can be made substantially safer and easier through the combination of ultrasound imaging aspects with therapeutic aspects of the ultrasound probe of device 1000.

In some embodiments, device 1000 can be used to provide access to vascular structures including arteries, veins, lymphatics, and to other hollow structures or body orifices such as the gastrointestinal tract, genitourinary tract, and the respiratory system. As such, the device 1000 can be used with, for example, a vascular sheath (not shown, but shown in priority applications and patents). Such sheaths are well known, and, thus, the general features of device 1000 for these embodiments can be in accordance with conventional devices.

In other embodiments, device 1000 can be used in procedures in various body spaces such as the pleural peritoneal space, pericardial space, perisphinal space, pelvis, and cerebrospinal space. For example, the device can be adapted for use in paracentesis, biopsy of any intraabdominal or intrapelvic organ, prostate biopsy, biopsy of tumors or otherwise suspected abnormal structures within the pelvis and abdomen, diagnosis of endometriosis, treatment by chemicals, cells, bio-agents, physical energy (e.g., cryo, radiofrequency, heat, laser) of any pathology within the pelvis and abdomen, visualization and application of therapy within the genitourinary tract, and drainage of abnormal or normal collection of fluid in actual or potential space in the abdomen, pelvis or genitourinary tract. In other embodiments, device 1000 can be in the form of a catheter/probe which can be used with a syringe to drain fluid from a patient's gall bladder or any other hollow or solid organ in the abdomen.

Other procedures that can be performed using device 1000 include procedures relating to diagnosis and treatment of infertility, including following a woman's ovum to determine an appropriate time for harvest, harvesting the ovum, and assisting in or performing the delivery of the fertilized egg to the uterus (with or without use of a contrast agent or echogenicity).

In some embodiments, device 1000 can be designed for use in cardiac or vascular procedures and for accessing various targets. For example, device 1000 can be designed to provide access to various structures such as the coronary sinus and other cardiac venous structures. Exemplary procedures that can be performed using device 1000 can include: epicardial biopsy; electronic mapping (endocardial or epicardial); electromechanical mapping (endocardial or epicardial); endocardial or epicardial ablation using any form of energy; cannulation or delivery of catheters, heart rhythm pacing leads or pacemaker devices, and other interventional devices (medicinal pumps for calming tremors in Parkinson's disease patients; and mapping and access to the fossa ovalis and patent foramen ovale to enable crossing the atrial septum and allowing transvenous access to the left side of the heart; pericardiocentesis; left ventricular lead placement; delivery of therapy (e.g., drugs, stem cells, laser therapy, or ultrasound energy); epicardial coronary artery bypass; valve repair and placement, delivery of cardiac shape modifying devices (e.g., ACORN® or MYOSPLINT® devices); myocardial scar reconstruction; ventricular reconstruction; ventricular assist device placement; and the treatment by chemicals, cells, bio-agents, physical energy (e.g., cryo, radiofrequency, heat, laser) of any pathology within the pericardial space or myocardium or intracardiac. As such, device 1000 can, in some cases, be used with a sheath-like device introduced via an image-guided needle that is insertable through, for example, a needle puncture in the patient's upper thigh and through a blood vessel all the way up to the heart. In such embodiments, guidewire can be used with the device 1000 to guide the device 1000 to the target area for guidewire introduction through the vein. In other embodiments, the device 1000 can be inserted through the pericardial space through the use of an introducer needle or sheath integrated therein.

In other embodiments, device 1000 can be in the form of a device that is used in performing a cardiac procedure such as a biopsy instrument or an instrument for heart valve repair or replacement. In this case, device 1000 can be provided with one or more transducer imaging systems or used with auxiliary imaging systems such as OCT, along with the other components required to provide ultrasound imaging using the transducers as discussed herein and tools to implement the repair or replacement, for example, of a heart valve with or without contrast or using echogenicity (for the tool or use of the contrast agent in proximate heart tissue).

In other embodiments, device 1000 can be in the form of devices for use in performing procedures on the musculo-skeletal system and for accessing the musculoskeletal system. For example, device 1000 can be used for treatment by chemicals, cells, bio-agents, or physical energy (cryo, radiofrequency, heat, laser) of any pathology within the joint cavity, joint components, or muscle and bone; visualization and application of therapy involving muscle, bone, and joint components, including a joint cavity; and drainage of abnormal or normal collection of fluid in actual or potential space in the muscle, bone, or joint components. In these embodiments, device 1000 can be in the form of a catheter or sheath that provides access to the musculo-skeletal system, thus allowing therapy delivery, intervention, placement of devices and diagnostics. Device 1000 can also be in the form of interventional devices for use in procedures on the musculo-skeletal system. Such catheters, sheaths, and devices are well known, and, thus, the general features of device 1000 for these embodiments can be in accordance with conventional devices. Device 1000 would further include one or more transducer assemblies such as linear phased arrays, along with the other components required to provide ultrasound imaging using the transducer assemblies as discussed herein.

In some embodiments, device 1000 can be in the form of devices for use in procedures on the brain and nervous system and for accessing the brain and nervous system. For example, such devices can be used for the treatment by chemicals, cells, bioagents, or physical energy (cryo, radiofrequency, heat, laser) of any pathology within the cranium and spinal and peri-spinal space including the vasculature contained within; visualization and application of therapy within the cranium, spinal, and peri-spinal space and all contained vasculature; drainage of abnormal or normal collection of fluid in actual or potential space in the cranium, spinal, and peri-spinal space and all contained vasculature; and for transcatheter delivery of interventional devices such as aneurysm clips, hematologic treatments, and any other drug or non drug therapy, either directly or via the vasculature or via any other hollow structure within the cranium, spinal, and peri-spinal space and all contained vasculature. In these embodiments, device 1000 can be in the form of a catheter or sheath that provides access to the brain and system, thus allowing therapy delivery, intervention, placement of devices and diagnostics. Ultrasound visualization need not be subcutaneous but external or via a body orifice such as the nasal passages and ear canal.

Device 1000 can further be adapted for use in procedures on the nasal passages, sinuses, ear canals and pharynx and other orifices and for accessing these orifices to reach organs such as the brain and the throat and such as via the esophagus for accessing the heart. In these embodiments, device 1000 can be in the form of a catheter and use a sheath that provides access to a desired site of the nasal passages, sinuses, pharynx and heart, thus allowing therapy delivery, intervention, placement/replacement of devices and defective heart valves and diagnostics. Device 1000 can also be in the form of interventional devices for use in procedures on the nasal passages, sinuses, and pharynx (e.g., devices for therapy delivery, intervention, placement of devices and diagnostics). Such catheters, sheaths, and devices are well known, and, thus, the general features of device 1000 for these embodiments can be in accordance with conventional devices. Device 1000 would further include one or more transducers, along with the other components required to provide ultrasound imaging using the transducers as discussed herein. Device 1000 can further be in the form of devices used to treat and address chronic problems and, as such, can be delivered and lodged in body cavities, organs, or other anatomic locations for long term monitoring or anatomy or function or dynamics including hemodynamics. In these examples, the device 1000 can be in the form of a catheter or probe and introduce a sheath or other conventional chronic treatment or monitoring device that can be lodged at a desired site. Device 1000 may further include one or more transducer probes, along with the other components required to provide ultrasound imaging using the transducer assemblies as discussed herein. Device 1000 can also be used for implanting a monitoring or drug delivery device at a specific site in the body using its imaging capabilities to assist the user in finding a precise target site. In some embodiments, the present device 1000 can further be integrated with other non-ultrasound imaging modalities including infrared, laser, CT scan, X-ray, optical coherence tomography, fiber optic instruments including, but not limited to endoscopic mapping. For example, the imaging lumen or probe can further be provided with a fiber optic lumen through which an optical fiber is insertable in place or proximate to the linear phased array.

The devices 1000 can be used to perform any variety of medical procedures including those set forth herein. The general features of these procedures are in accordance with conventional procedures and further make use of the integrated imaging system to provide visualization while accessing and performing procedures at the target site. Access to other organs, structures, and spaces can be performed in similar fashion with appropriate procedural modifications specific for the particular organs, structures or spaces.

All documents mentioned herein are incorporated by reference herein as to any description which may be deemed essential to an understanding of illustrated and discussed aspects and embodiments of devices and methods herein.

Although the devices and methods discussed above and primarily illustrated and described herein provide instruments that also can be adapted for performing minimally invasive diagnostic or therapeutic procedures on humans, it will be appreciated by those skilled in the art that such instruments and methods also are adaptable for use in other surgical procedures as well as in performing various veterinary surgeries. Further, while several preferred embodiments have been described using specific terms, such description is for illustrative purposes only, and it is to be understood that changes and variations may be made without departing from the spirit or scope of the following claims.

What is claimed is:
1. A sheath body comprising:
 a first lumen comprising a closed distal end and an open proximal end, the first lumen being configured to receive a forward looking imaging device;
 a locking mechanism comprising a tab that protrudes from a proximal portion of the first lumen to, the locking mechanism being operably coupled to the proximal end of the first lumen and configured to lock the forward looking imaging device into the first lumen in a manner that a cable of the forward looking imaging device can extend from the forward looking imaging device and out of the open proximal end of the first lumen; and
 a second lumen comprising:
  first and second movable guides that contact each other when the first lumen is in a closed configuration and do not contact each other when the first lumen is in an open configuration, and open distal and proximal ends when the second lumen is in the closed configuration, the second lumen being configured to receive a medical tool, wherein the second lumen is oriented with respect to the first lumen such that when the medical tool is loaded into the second lumen, a portion of the medical tool that protrudes from the second lumen is within a forward imaging field of view of the forward looking imaging device.

2. The sheath body of claim 1, wherein the second lumen is further oriented with respect to the first lumen such that a forward-imaging orientation of the medical tool is produced by the forward looking imaging device.

3. The sheath body of claim 1, wherein the closed distal end of the first lumen is a blunt end.

4. The sheath body of claim 1, wherein the second lumen is configured to transition between the open configuration and the closed configuration such that the medical tool is insertable and removable from the sheath body when the second lumen is in the open configuration.

5. The sheath body of claim 4, wherein the second lumen is configured to open and close along an entire length of the second lumen.

6. The sheath body of claim 5, wherein the second lumen is configured to open and close along an entire top length of the second lumen.

7. The sheath body of claim 4, wherein the second lumen comprises one or more tabs to facilitate ejection of the medical tool from the second lumen when the second lumen is in the open configuration.

8. The sheath body of claim 4, wherein the second lumen comprises an actuation mechanism coupled to the second lumen to control opening and closing of the second lumen.

9. The sheath body of claim 8, wherein the second lumen comprises a locking mechanism that locks the second lumen in the closed configuration.

10. A method of performing an image guided medical procedure on a subject, the method comprising:
providing a sheath body comprising a first lumen comprising a closed distal end and an open proximal end, the first lumen being configured to receive a forward looking imaging device, a locking mechanism comprising a tab that protrudes from a proximal portion of the first lumen, the locking mechanism operably coupled to the proximal end of the first lumen and configured to lock the forward looking imaging device into the first lumen in a manner that a cable of the forward looking imaging device can extend from the forward looking imaging device and out of the open proximal end of the first lumen, and a second lumen comprising first and second movable guides that contact each other when the first lumen is in a closed configuration and do not contact each other when the first lumen is in an open configuration and open distal and proximal ends when the second lumen is in the closed configuration, the second lumen being configured to receive a medical tool, wherein the second lumen is oriented with respect to the first lumen such that when the medical tool is loaded into the second lumen, a portion of the medical tool that protrudes from the second lumen is within a forward imaging field of view of the forward looking imaging device;

loading a forward looking imaging device into the first lumen such that the forward looking imaging device is locked into the first lumen by the locking mechanism;

loading a medical tool into the second lumen; and performing at least a portion of a medical procedure on a subject using the medical tool loaded in the second lumen while viewing the medical tool through the forward imaging field of view of the forward looking imaging device.

11. The method of claim 10, wherein the second lumen is configured to transition between the open configuration and the closed configuration such that the medical tool is insertable and removable from the sheath body when the second lumen is in the open configuration, and the method further comprises opening the second lumen to remove the medical tool from the sheath body while performing the medical procedure.

12. The method of claim 11, further comprising:
loading a second medical tool into the second lumen while the second lumen is in the open configuration;

closing the second lumen; and continuing to perform the medical procedure on the subject using the second medical tool loaded in the second lumen while viewing the second medical tool through the forward imaging field of view of the forward looking imaging device.

13. The method of claim 10, wherein the sheath body is positioned on a surface of the subject while the medical tool is positioned within the subject.

14. The method of claim 10, wherein a portion of the sheath body is positioned in the subject.

15. The method of claim 11, wherein the second lumen is configured to open and close along an entire length of the second lumen.

16. The method of claim 15, wherein the second lumen is configured to open and close along an entire top length of the second lumen.

17. The method of claim 11, wherein the second lumen comprises one or more tabs to facilitate ejection of the medical tool from the second lumen when the second lumen is in the open configuration.

18. The method of claim 11, wherein the second lumen comprises an actuation mechanism coupled to the second lumen to control opening and closing of the second lumen.

19. The method of claim 11, wherein the second lumen comprises a locking mechanism that locks the second lumen in the closed configuration.

* * * * *